United States Patent
Kawashima et al.

(10) Patent No.: US 8,134,004 B2
(45) Date of Patent: Mar. 13, 2012

(54) SUBSTITUTED N-BICYCLICALKYL BICYCLICCARBOXYAMIDE COMPOUNDS

(75) Inventors: Tadashi Kawashima, Chita-gun (JP); Satoshi Nagayama, Chita-gun (JP); Kazunari Nakao, Chita-gun (JP); Hirotaka Tanaka, Chita-gun (JP)

(73) Assignee: Pfizer Inc., New York, NY (US)

( * ) Notice: Subject to any disclaimer, the term of this patent is extended or adjusted under 35 U.S.C. 154(b) by 527 days.

(21) Appl. No.: 12/305,440

(22) PCT Filed: Jul. 2, 2007

(86) PCT No.: PCT/IB2007/001984
§ 371 (c)(1),
(2), (4) Date: Dec. 18, 2008

(87) PCT Pub. No.: WO2008/007211
PCT Pub. Date: Jan. 17, 2008

(65) Prior Publication Data
US 2009/0253740 A1 Oct. 8, 2009

Related U.S. Application Data

(60) Provisional application No. 60/806,993, filed on Jul. 11, 2006, provisional application No. 60/883,196, filed on Jan. 3, 2007.

(51) Int. Cl.
*C07D 215/38* (2006.01)
*C07D 215/12* (2006.01)
(52) U.S. Cl. ........................ 546/169; 546/176
(58) Field of Classification Search .................. 546/169, 546/176
See application file for complete search history.

(56) References Cited

U.S. PATENT DOCUMENTS

2007/0232620 A1  10/2007  Dorsch et al. ............ 514/225.05

FOREIGN PATENT DOCUMENTS

| WO | WO 9701539 | 1/1997 |
|---|---|---|
| WO | WO 00/73283 | * 12/2000 |
| WO | WO 0073283 | 12/2000 |
| WO | WO 0230426 | 4/2002 |
| WO | WO 03068749 | 8/2003 |
| WO | WO 2004014377 | 2/2004 |
| WO | WO 2004069792 | 8/2004 |
| WO | WO 2005014533 | 2/2005 |
| WO | WO 2005070885 | 8/2005 |
| WO | WO 2005070929 | 8/2005 |
| WO | WO 2005095329 | 10/2005 |
| WO | WO 2005123688 | 12/2005 |
| WO | WO 2006051378 | 5/2006 |

OTHER PUBLICATIONS

West, Solid State Chemistry and Its Applications, John Wiley & Sons, 1984.*
Planells-Cases, et al., Eur. J. Physiol., vol. 451, pp. 151-159 (2005).
Deal, et al., Clinical Therapeutics, vol. 13(3), pp. 338-395 (1991).
Honore, et al., J. Pharmacology and Experimental Therapeutics, vol. 314(1), pp. 410-421 (2005).
Femihough, et al., Neuroscience Letters, vol. 388, pp. 75-80 (2005).

* cited by examiner

*Primary Examiner* — Nizal Chandrakumar
(74) *Attorney, Agent, or Firm* — A. Dean Olson

(57) ABSTRACT

This invention provides a compound of the formula (I): And their use for the treatment of disease conditions caused by overactivation of the VR1 receptor such as pain, or the like in mammal. This invention also provides a pharmaceutical composition comprising the above compound.

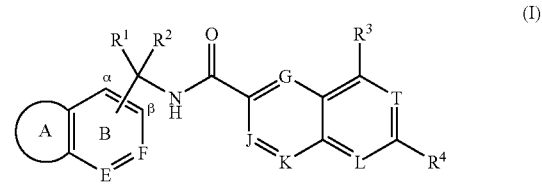

12 Claims, No Drawings

SUBSTITUTED N-BICYCLICALKYL BICYCLICCARBOXAMIDE COMPOUNDS

This application claims priority from International Application Number PCT/IB2007/001984 filed Jul. 2, 2007 which claims priority from U.S. Provisional Application 60/806,993 filed Jul. 11, 2006 and U.S. Provisional Application 60/883,196 filed Jan. 3, 2007.

TECHNICAL FIELD

This invention relates to novel substituted N-bicyclic alkyl bicyclic-carboxamide compounds and to their use in therapy. These compounds are particularly useful as antagonists of the VR1 (Type I Vanilloid) receptor, and are thus useful for the treatment of pain, neuralgia, neuropathies, nerve injury, burns, migraine, carpal tunnel syndrome, fibromyalgia, neuritis, sciatica, pelvic hypersensitivity, bladder disease, inflammation, or the like in mammals, especially humans. The present invention also relates to a pharmaceutical composition comprising the above compounds.

BACKGROUND ART

The Vanilloid receptor 1 (VR1) is a ligand gated non-selective cation channel. It is believed to be a member of the transient receptor potential super family. VR1 is recognized as a polymodal nociceptor that integrates multiple pain stimuli, e.g., noxious heat, protons, and vanifloids (European Journal of Physiology 451:151-159, 2005). A major distribution of VR1 is in the sensory (Aδ- and C-) fibers, which are bipolar neurons having somata in sensory ganglia. The peripheral fibers of these neurons innervate the skin, the mucosal membranes, and almost all internal organs. It is also recognized that VR1 exists in bladder, kidney, brain, pancreas, and various kinds of organs. A body of studies using VR1 agonists, e.g., capsaicin or resiniferatoxin, have suggested that VR1 positive nerves are thought to participate in a variety of physiological responses, including nociception (Clinical Therapeutics. 13(3): 338-395, 1991, Journal of Pharmacology and Experimental Therapeutics 314:410-421, 2005, and Neuroscience Letter 388: 75-80, 2005). Based on both the tissue distribution and the roles of VR1, VR1 antagonists would have good therapeutic potential.

WO2005070929 discloses heterocyclic amine derivatives as vanilloid receptor ligands. WO2005070885 discloses amide derivatives useful as vanilloid receptor ligands. WO 2004069792 discloses quinoline-derived amide derivatives useful for prevention or treatment of e.g. inflammatory pain, burning pain, chronic obstructive pulmonary disease and osteoarthritis, are vanilloid receptor 1 modulators. WO 2003068749 discloses quinoline or isoquinoline carboxamide derivatives useful as antagonist of the vanilloid receptor (VR1). WO2005123688 discloses a variety of 3-aminoindazole derivatives as SGK-inhibitors for use in treatment of SGK-related diseases and illness such as diabetes, obesity and metabolic syndrome etc. WO2006051378 discloses a variety of N-sulfonylaminobenzyl-2-phenoxy amide derivatives as a modulator for vanilloid receptor. WO97/01539 discloses quinoline deridatives as melatonin conditions. WO2002/30426 discloses heteroaryl compounds as HIV integrase inhibitors. WO 2000073283 discloses heteroaryl compounds as metabotropic glutamate receptor antagonists. WO 2004014377 discloses heteroaryl compounds as matrix metalloproteinase inhibitors. WO 2005014533 discloses heteroaryl compounds as factor IX antagonists.

It would be desirable if there were provided improved VR1 selective antagonist with enhanced binding activity with the VR1 receptor by systemic administration and with a good half-life. Other potential advantages include less toxicity, good absorption, good solubility, low protein binding affinity, less drug-drug interaction, a reduced inhibitory activity at HERG channel, reduced QT prolongation and good metabolic stability.

BRIEF DISCLOSURE OF THE INVENTION

It has now been found that certain substituted carboxamide derivatives are potent VR1 antagonists with analgesic activity by systemic administration.

The present invention provides a compound of the following formula (I):

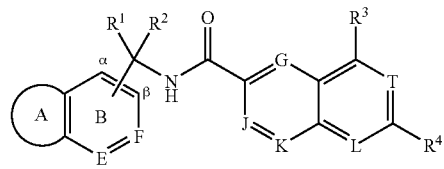

wherein
ring A is

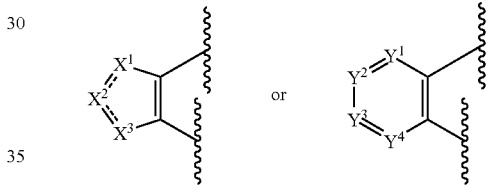

wherein
one of $X^1$ and $X^3$ is N, another of $X^1$ and $X^3$ is NH or S, and $X^2$ is N or $CR^5$,
one of $X^1$ and $X^3$ is $CH_2$, another of $X^1$ and $X^3$ is NH or N, and $X^2$ is C=O or N,
one of $X^1$ and $X^3$ is $CR^6$, another of $X^1$ and $X^3$ is NH, and $X^2$ is N or $CR^5$,
$X^1$ and $X^3$ are NH and $X^2$ is C=O, or
$Y^1$ is N or $CR^7$, $Y^2$ is N or $CR^8$, $Y^3$ is N or $CR^9$ and $Y^4$ is N or $CR^{10}$;
the substitution site of ring B is the alpha- or beta-position;
E, G, J and K are each independently CH or N; F is CH or C—$CH_3$;
L and T are each independently CH or N; $R^1$ and $R^2$ are each independently hydrogen, ($C_1$-$C_6$)alkyl, or hydroxy($C_1$-$C_6$)alkyl; $R^3$ is hydrogen; $R^4$ is ($C_1$-$C_6$)alkyl, hydroxy($C_1$-$C_6$)alkyl, ($C_3$-$C_6$)cycloalkyl, ($C_1$-$C_4$)alkyl($C_3$-$C_6$)cycloalkyl, ($C_1$-$C_4$)alkoxy($C_1$-$C_6$)alkyl optionally substituted with halo or halo($C_2$-$C_6$)alkyl optionally substituted with hydroxy, $R^5$ and $R^6$ are each independently hydrogen, ($C_1$-$C_6$)alkyl, hydroxy($C_1$-$C_6$)alkyl or hydroxy($C_1$-$C_6$)alkoxy-($C_1$-$C_6$)alkyl; $R^7$, $R^8$, $R^9$ and $R^{10}$ are each independently hydrogen, halo, ($C_1$-$C_6$)alkyl, hydroxy($C_1$-$C_6$)alkyl or hydroxy($C_1$-$C_6$)alkoxy-($C_1$-$C_6$)alkyl; and each dotted bond is a single or a double bond; or a pharmaceutically acceptable salt or solvate thereof.

DETAILED DESCRIPTION OF THE INVENTION

As used herein, the term "halogen" or "halo" means fluoro, chloro, bromo or iodo, preferably fluoro or chloro.

As used herein, the terms "(C₁-C₆)alkyl" and "(C₁-C₄)alkyl" mean straight or branched chain saturated radicals having the required number of carbon atoms, including, but not limited to methyl, ethyl, n-propyl, iso-propyl, n-butyl, iso-butyl, secondary-butyl, tert-butyl and 2-methylbutyl groups. Preferred groups are methyl, ethyl, n-propyl, n-butyl, tert-butyl and 2-methylbutyl groups.

As used herein, the terms "(C₃-C₆)cycloalkyl" means non-aromatic saturated or unsaturated hydrocarbon ring, having the required number of carbon atoms, including, but not limited to cyclopropyl, cyclobutyl, cyclopentyl and cyclohexyl groups.

As used herein, the term "(C₁-C₆)alkoxy" means (C₁-C₆)alkyl-O— wherein (C₁-C₆)alkyl radical is as defined above, including, but not limited to methoxy, ethoxy, n-propoxy, iso-propoxy, n-butoxy, iso-butoxy, sec-butoxy and tert-butoxy. Preferred groups are methoxy, ethoxy, n-propoxy, n-butoxy and tert-butoxy.

As used herein, the term "hydroxy(C₁-C₆)alkyl" and "hydroxy(C₁-C₄)alkyl" means (C₁-C₆)alkyl or (C₁-C₄)alkyl radical as defined above which is substituted by at least one hydroxy group including, but not limited to, hydroxymethyl, hydroxyethyl, hydroxy n-propyl, hydroxy iso-propyl (e.g. 1-hydroxy-1,1-dimethylmethyl), hydroxy n-butyl, hydroxy iso-butyl, hydroxy secondary-butyl and hydroxy tert-butyl. Preferred groups are hydroxymethyl, hydroxyethyl, hydroxy n-propyl, hydroxy iso-propyl (e.g. 1-hydroxy-1,1-dimethylmethyl), hydroxy n-butyl and hydroxy tert-butyl.

As used herein, the term "hydroxy(C₁-C₆)alkoxy" and "hydroxy(C₁-C₄)alkoxy" means (C₁-C₆)alkoxy or (C₁-C₄)alkoxy radical as defined above which is substituted by hydroxy group including, but not limited to, hydroxymethoxy, hydroxyethoxy, hydroxy n-propoxy, hydroxy iso-propoxy, hydroxy n-butoxy, hydroxy iso-butoxy, hydroxy sec-butoxy and hydroxy tert-butoxy. Preferred hydroxyalkoxy groups are hydroxymethoxy, hydroxyethoxy, hydroxy n-propoxy and hydroxy n-butoxy.

As used herein, the term "(C₁-C₆)alkoxy-(C₁-C₆)alkyl" means (C₁-C₆)alkyl radical as defined above which is substituted by (C₁-C₆)alkoxy group as defined above.

As used herein, the term "(C₁-C₆)alkoxy-(C₁-C₆)alkoxy" means (C₁-C₆)alkoxy radical as defined above which is substituted by (C₁-C₆)alkoxy as defined above. Preferred groups are methoxy methoxy, methoxy ethoxy or ethoxy ethoxy groups.

hydroxy n-propyl, hydroxy iso-propyl (e.g. 2-hydroxy-1,1-dimethylethyl) and hydroxy n-butyl.

As used herein, the term "hydroxy(C₁-C₆)alkoxy-(C₁-C₆)alkyl" and "hydroxy(C₁-C₄)alkoxy-(C₁-C₄)alkyl" means (C₁-C₆)alkyl radical as defined above which is substituted by hydroxy(C₁-C₆)alkoxy group or (C₁-C₄)alkyl radical as defined above which is substituted by hydroxy(C₁-C₄)alkoxy group as defined above.

As used herein the term "halo(C₁-C₆)alkyl" and "halo(C₁-C₄)alkyl" mean (C₁-C₆)alkyl or (C₁-C₄)alkyl radical which is substituted by one or more halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trifluoro-1,1-dimethylethyl, 2,2,2-trichloroethyl, 3-fluoropropyl, 4-fluorobutyl, chloromethyl, trichloromethyl, iodomethyl, bromomethyl and 4,4,4-trifluoro-3-methylbutyl groups. Preferred groups are fluoromethyl, difluoromethyl, trifluoromethyl, 2-fluoroethyl, 2,2-difluoroethyl, 2,2,2-trifluoroethyl and 2,2,2-trifluoro-1,1-dimethylethyl groups.

As used herein the terms "halo(C₁-C₆)alkoxy" mean (C₁-C₆)alkyl-O—, which is substituted by one or more halogen atoms as defined above including, but not limited to, fluoromethoxy, difluoromethoxy, trifluoromethoxy, 2-fluoroethoxy, 2,2-difluoroethoxy, 2,2,2-trifluoroethoxy, 2,2,2-trifluoro-1,1-dimethylethoxy, 2,2,2-trichloroethoxy, 3-fluoropropoxy, 4-fluorobutoxy, chloromethoxy, trichloromethoxy, iodomethoxy, bromomethoxy and 4,4,4-trifluoro-3-methylbutoxy groups. Preferred halo(C₁-C₆)alkyl-O— or halo(C₁-C₃)alkyl-O— groups are fluoromethoxy, difluoromethoxy, trifluoromethoxy, 2-fluoroethoxy, 2,2-difluoroethoxy, 2,2,2-trifluoroethoxy and 2,2,2-trifluoro-1,1-dimethylethoxy groups.

The dotted line of the ring A can be a single bond or a double bond. It depends on the atom of the ring A, such as $X^1$, $X^2$ or $X^3$. The ring A includes, but not limited to, the rings below.

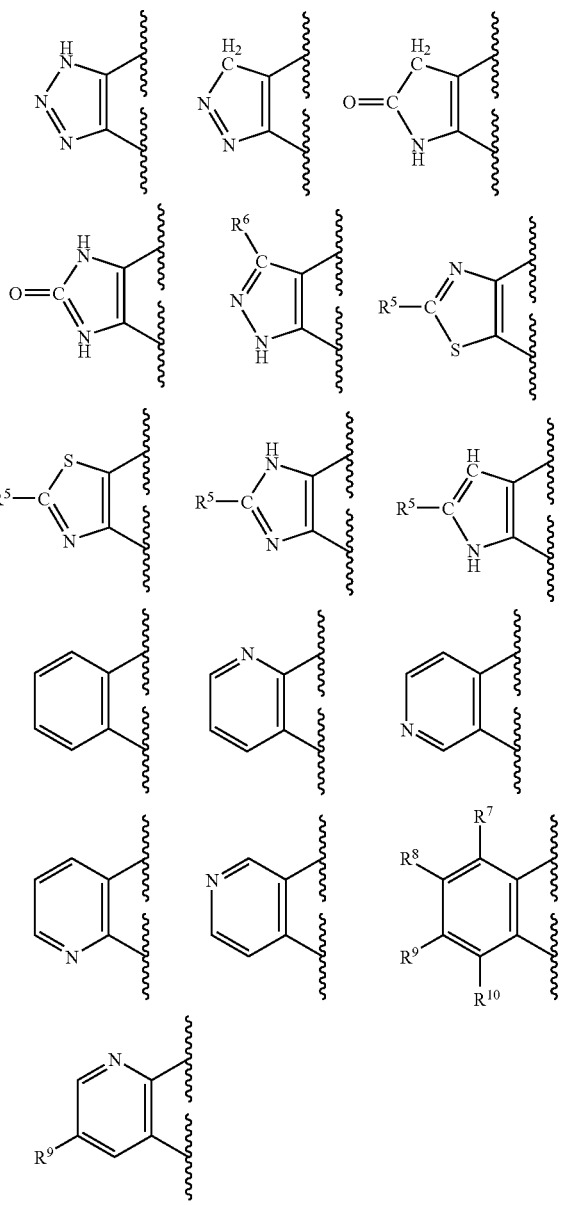

$R^5$ and $R^6$ are each independently hydrogen, (C₁-C₆)alkyl, hydroxy(C₁-C₆)alkyl or hydroxy(C₁-C₆)alkoxy-(C₁-C₆)

alkyl. Preferably, $R^5$ or $R^6$ is H or hydroxy($C_1$-$C_4$)alkyl. More preferably, $R^5$ or $R^6$ is hydroxymethyl or H. Most preferably, $R^5$ or $R^6$ are H.

$R^7$, $R^8$, $R^9$ and $R^{10}$ are each independently hydrogen, halo, ($C_1$-$C_6$)alkyl, hydroxy($C_1$-$C_6$)alkyl or hydroxy($C_1$-$C_6$)alkoxy-($C_1$-$C_6$)alkyl. Preferably $R^7$, $R^8$, $R^9$ or $R^{10}$ is H, halo, ($C_1$-$C_4$)alkyl or hydroxy($C_1$-$C_4$)alkyl. More preferably, $R^7$, $R^8$, $R^9$ or $R^{10}$ is selected from H, fluoro, methyl or hydroxymethyl.

More preferred A rings are:

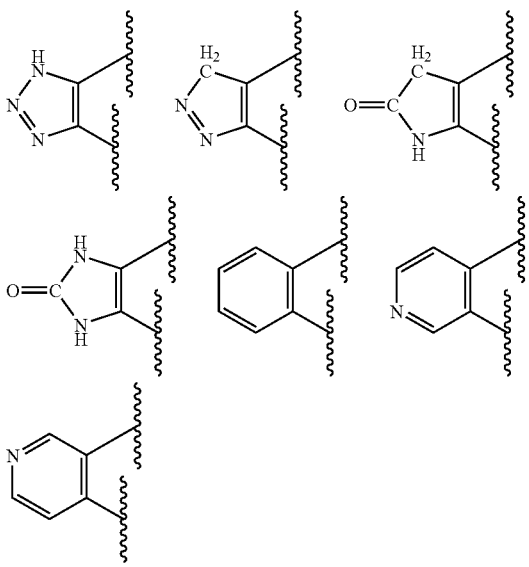

Preferably $R^1$ is hydrogen or ($C_1$-$C_4$)alkyl; more preferably; hydrogen, methyl, ethyl or propyl; still more preferably hydrogen or methyl.

Preferably $R^2$ is hydrogen or ($C_1$-$C_4$)alkyl; more preferably; hydrogen, methyl, ethyl or propyl; still more preferably hydrogen.

Preferred compounds of formula (I) are those where $R^1$ and $R^2$ are both hydrogen.

Other preferred compounds of formula (I) are those where $R^1$ is other than H, preferably methyl or ethyl, more preferably methyl, and $R^2$ is hydrogen and where the carbon atom bearing $R^1$ and $R^2$ is in the (R) configuration as described in formula (Ia), or racemic mixture containing such (R) enantiomer.

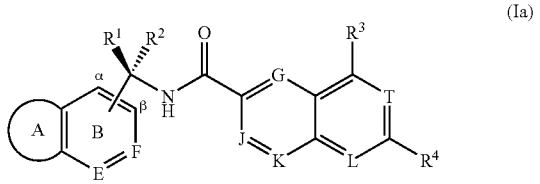
(Ia)

Preferably $R^4$ is ($C_1$-$C_4$)alkyl, hydroxy($C_1$-$C_4$)alkyl, cyclopropyl, ($C_3$-$C_6$)cycloalkyl-($C_1$-$C_4$)alkyl or halo($C_2$-$C_4$)alkyl optionally substituted with hydroxy. More preferably $R^4$ is cyclopropyl, 1-methyl-cylopropyl, tert-butyl, 2,2,2-trifluoro-1-hydroxy-1-methylethyl, 2,2,2-trifluoro-1-methoxy-1-methylethyl or 2,2,2-trifluoro-1,1-dimethylethyl. Still more preferably $R^4$ is tert-butyl or 2,2,2-trifluoro-1,1-dimethyl-ethyl.

Preferably
$X^1$ is N, $X^3$ is NH and $X^2$ is $CR^5$,
$X^1$ is $CH_2$, $X^3$ is NH or N, and $X^2$ is C=O or N,
$X^1$ is NH, $X^3$ is N, and $X^2$ is N
$X^1$ is $CR^6$, $X^3$ is NH, and $X^2$ is N or $CR^5$, or
$X^1$ and $X^3$ are NH and $X^2$ is C=O;
most preferably $X^1$ is N, $X^3$ is NH and $X^2$ is N, $X^1$ is $CH_2$, $X^3$ is N or NH and $X^2$ is N or CO, or X is NH, $X^3$ is NH and $X^2$ is CO.

Preferably, E is N and $Y^1$, $Y^2$, $Y^3$ and $Y^4$ are $CR^7$, $CR^8$, $CR^9$ and $CR^{10}$, respectively.

Preferably, E and F are CH and one of $Y^1$, $Y^2$, $Y^3$ and $Y^4$ is N and the others are independently CH.

Preferably G, J, K, L and T are CH.

Preferably one of G, J, K, L and T is N, and the others are CH.

Preferably J and T are CH and one of G, K and L is N, and the others are CH.

Preferred structures of ring system A and B and linker (—$CR^1R^2$—NH—) include as follows.

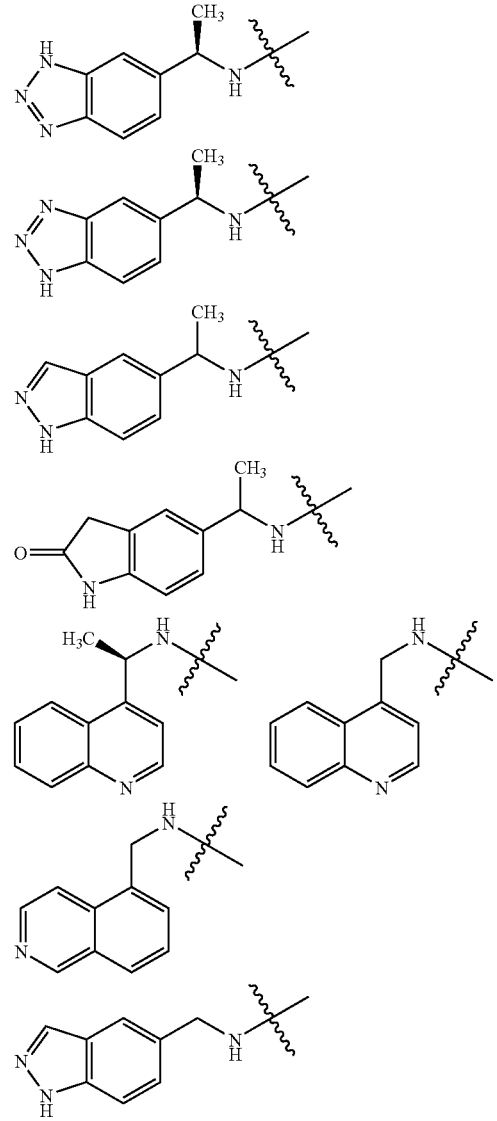

Preferred rings system structures of opposite side of ring system A and B include as follows.

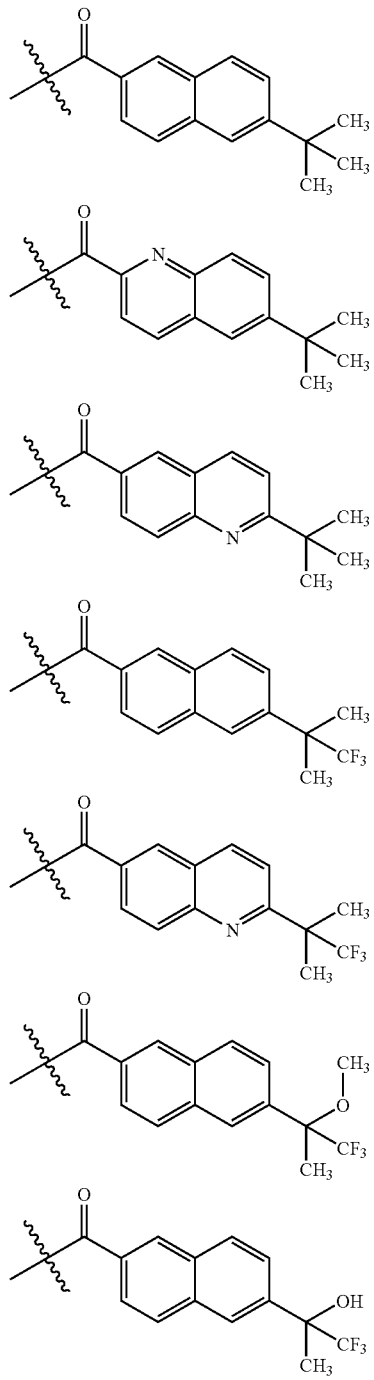

Preferred compounds of the invention include those in which each variable in formula (I) is selected from the preferred groups for each variable.

Specific preferred compounds of the invention are those listed in the Examples section below and the pharmaceutically acceptable salts and solvates thereof.

The compounds of formula (I), being VR1 antagonists, are potentially useful in the treatment of a range of disorders, particularly the treatment of acute cerebral ischemia, pain, chronic pain, acute pain, nociceptive pain, neuropathic pain, inflammatory pain, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, menstrual pain, bladder disease, such as incontinence, micturition disorder, renal colic and cystitis, inflammation, such as burns, rheumatoid arthritis and osteoarthritis, neurodegenerative disease, such as stroke, post stroke pain and multiple sclerosis, pulmonary disease, such as asthma, cough, chronic obstructive pulmonary disease (COPD) and broncho constriction, gastrointestinal disorders, such as gastroesophageal reflux disease (GERD), dysphagia, ulcer, irritable bowel syndrome (IBS), inflammatory bowel disease (IBD), colitis and Crohn's disease, ischemia, such as cerebrovascular ischemia, emesis, such as cancer chemotherapy-induced emesis, and obesity, or the like in mammals, especially humans. The treatment of pain, particularly neuropathic pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

The present invention provides a pharmaceutical composition including a compound of formula (I), or a pharmaceutically acceptable salt or solvate thereof, together with a pharmaceutically acceptable excipient. The composition is preferably useful for the treatment of the disease conditions defined above.

The present invention further provides a compound of formula (I), or a pharmaceutically acceptable salt or solvate thereof, for use as a medicament.

Further, the present invention provides a method for the treatment of the disease conditions defined above in a mammal, preferably a human, which includes administering to said mammal a therapeutically effective amount of a compound of formula (I), or a pharmaceutically acceptable salt or solvate thereof.

Yet further, the present invention provides the use of a compound of formula (I), or a pharmaceutically acceptable salt or solvate thereof, in the manufacture of a medicament for the treatment of the disease conditions defined above.

Yet further, the present invention provides a combination of a compound of the formula (I), or a pharmaceutically acceptable salt or solvate thereof, and another pharmacologically active agent.

In this specification, especially in "General Synthesis" and "Examples", the following abbreviations can be used:
BEP 2-bromo-1-ethylpyridinium tetrafluoroborate
BOP benzotriazol-1-yloxy-tris(dimethylamino)phosphonium hexafluorophosphate
CDI 2-chloro-1,3-dimethylimidazolinium chloride
DCC dicyclohexylcarbodiimide
DCM dichloromethane
DME 1,2-dimethoxyethane, dimethoxyethane
DMF N,N-dimethylformamide
DMSO dimethyl sulfoxide
EDC 1-ethyl-3-(3'-dimethylaminopropyl)carbodiimide hydrogen chloride
EtOAc ethyl acetate
EtOH ethanol
HOBt 1-hydroxybenzotriazole
MeOH methanol
NMP N-methyl-2-pyrroliidone
THF tetrahydrofuran
TFA trifluoroacetic acid
HBTU 2-(1H-benzenotriasol-1-yl)-1,1,3,3-tetramethyluronium hexafluorophosphate
General Synthesis The compounds of the present invention may be prepared by a variety of processes well known for the preparation of compounds of this type, for example as shown in the following reaction Schemes.

All starting materials in the following general syntheses may be commercially available or obtained by conventional methods known to those skilled in the art.

Scheme 1:

(II)    (III)

Step 1A

—continued (I)

This illustrates the preparation of compounds of formula (I).

Step 1A: In this Step, amide compounds of formula (I) can be prepared by the coupling reaction of an amine compound of formula (II) with the acid compound of formula (III) in the presence or absence of a coupling reagent in an inert solvent. Suitable coupling reagents are those typically used in peptide synthesis including, for example, diimides (e.g., DCC, EDC, 2-ethoxy-N-ethoxycarbonyl-1,2-dihydroquinoline, BEP, CDI, BOP, diethyl azodicarboxylate-triphenylphosphine, diethylcyanophosphate, diethylphosphorylazide, 2-chloro-1-methylpyridinium iodide, N,N'-carbonyldiimidazole, benzotriazole-1-yl diethyl phosphate, ethyl chloroformate or isobutyl chloroformate. The reaction can be carried out in the presence of a base such as HOBt, N,N-diisopropylethylamine, N-methylmorpholine or triethylamine. The amide compound of formula (I) can be formed via an acylhalide, which can be obtained by the reaction with halogenating agents such as oxalylchloride, phosphorus oxychloride or thionyl chloride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone; nitromethane; DMF; NMP; sulfolane; DMSO; 2-butanone; acetonitrile; halogenated hydrocarbons such as DCM, dichloroethane or chloroform; and ethers such as THF or 1,4-dioxane. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., more preferably from about 0° C. to 60° C. The time required for the reaction can also vary widely, depending on many factors, notably the reaction temperature and the nature of the reagents and solvent employed. However, provided that the reaction is effected under the preferred conditions outlined above, a period of 5 minutes to 1 week, more preferably 30 minutes to 24 hours, will usually suffice.

Scheme 2:

(IV)    Step 2A

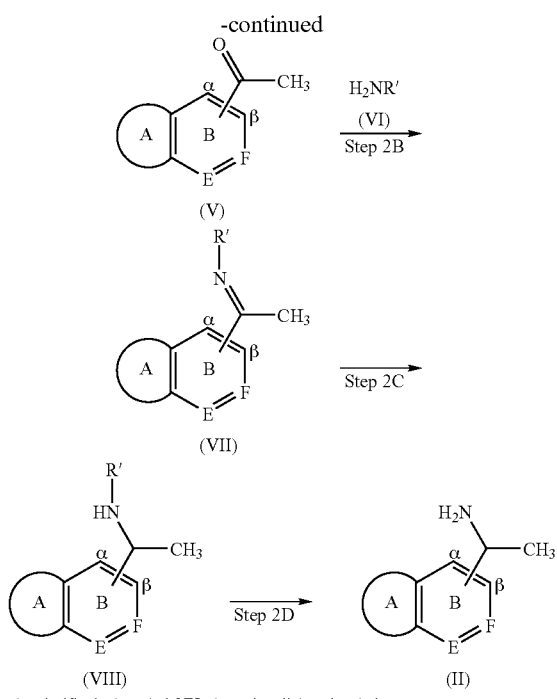

R': t-butylsulfinyl, phenethyl, NH₂, benzyl or diphenylmethyl

When $R^2$ is methyl, the compound of formula (II) may be prepared from a compound of formula (IV). This illustrates preparation of compounds of formula (II).

Step 2A: In the above formula, a compound formula (V) can bev prepared by coupling reaction of the compound of formula (IV) under a basic condition with a transition metal catalysts and additives in a solvent. Examples of suitable solvents include: protic solvents such as water, alcohols such as MeOH or EtOH and co-solvents of water or alcohols as protic solvents mixed with THF, 1,4-dioxane, DMF or acetonitrile. This reaction can be carried out in the presence of a suitable catalyst. There is likewise no particular restriction on the nature of the catalysts used, and any catalysts commonly used in reactions of this type can equally be used here. Examples of such catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bisacetonitriledichloropalladium(0), bis(dibenzylideneacetone)palladium(0), tris(dibenzylideneacetone)dipalladium(0) or [1,1'-bis(diphenylphosphino)ferrocene]palladium(II) dichloride. Preferable catalysts are tetrakis(triphenylphosphine)-palladium, bis(triphenylphosphine)palladium(II) chloride, palladium(II) acetate, palladium(II) chloride, bisacetonitriledichloropalladium(0), bis(dibenzylideneacetone)palladium(0), tris(dibenzylideneacetone)dipalladium(0) or [1,1'-bis(diphenylphosphino)ferrocene]palladium(II) dichloride. This reaction can be carried out in the presence of a suitable additive agent. Examples of such additive agents include: triphenylphosphine, tri-tert-butylphosphine, 1,2-bis(diphenylphosphino)ethane, 1,3-bis(diphenylphosphino)propane, 1,1'-bis(diphenylphosphino)ferrocene, tri-2-furylphosphine, tri-o-tolylphosphine, 2-(dichlorohexylphosphino)biphenyl or triphenylarsine. This reaction can be carried out in the presence of bases such as potassium carbonate, sodium carbonate or cesium carbonate. The reaction can be carried out at a temperature of from 0° C. to 200° C., more preferably from 20° C. to 120° C. Reaction time is, in general, from 5 minutes to 48 hours, more preferably 30 minutes to 24 hours, will usually suffice.

Step 2B: In this step, the compound of formula (VII) can be prepared by coupling reaction of the compound of formula (V) with the amine of formula (VI) under dehydrate reagent and/or acid and/or Lewis Acid. A preferred dehydrate reagent includes Lewis acids such as titanium(IV) chloride, titanium(IV) ethoxide, titanium(IV) isopropoxide; acids such as p-toluenesulfonic acid. Examples of suitable solvents include: THF; 1,4-dioxane; DMF; acetonitrile; alcohols such as MeOH or EtOH; halogenated hydrocarbons such as DCM, 1,2-dichloroethane, chloroform or carbon tetrachloride; or acetic acid. Reaction temperature is generally in the range of 0 to 200° C., preferably in the range of from 100° C. to 140° C. Reaction time is, in general, from 1 minute to a day, preferably from 5 minutes to 1 hour. If necessary, microwave condition is applied to the reaction.

Step 2C: In this step, a compound of formula (VIII) can be prepared by reduction of the compound of formula (VII) with a reducing agent. This reaction may be carried out in the presence of a suitable reducing agent such as diboran, boran-methyl sulfide complex, sodium borohydride, lithium borohydride, sodium borohydride, or lithium aluminum hydride in an inert solvent selected from THF and diethyl ether. Reaction temperature is generally in the range of −100 to 250° C., preferably in the range of 0° C. to the reflux temperature, but if necessary, lower or higher temperature can be employed. Reaction time is, in general, from 1 minute to a day, preferably from 20 minutes to 5 hours, however shorter or longer reaction times, if necessary, can be employed. The reduction may also be carried out under known hydrogenation conditions such as in the presence of a metal catalyst such as Raney nickel catalysts in the presence or absence of hydrazine, palladium catalysts or platinum catalysts under hydrogen atmosphere. This reaction may be carried out in an inert solvent such as MeOH, EtOH, and THF in the presence or absence of hydrogen chloride. If necessary, this reduction may be carried out under the adequate pressure in the range from about 0.5 to 10 kg/cm², preferably in the range from 1 to 6 kg/cm². Examples of suitable solvents are similar to those mentioned in Step 2B.

Reaction temperature is generally in the range of −100° C. to 250° C., preferably in the range of 0° C. to the reflux temperature, but if necessary, lower or higher temperature can be employed. Reaction time is, in general, from 1 minute to 2 days, preferably from 20 minutes to 24 hours.

Step 2D: In this Step, the compound of the formula (II) can be prepared by deprotection and/or salt formation of the compound of formula (VIII) under acidic condition in an inert solvent using a method of Journal of American Chemical Society, 1999, 121, 268-269 by By D. Cogan et. al. An acid includes, for example, but not limited to hydrogen chloride, hydrogen bromide, trifluoromethane sulfonic acid, acetic acid or p-toluenesulfonic acid. The reaction may be also carried out under known hydrogenation conditions such as in the presence of a metal catalyst such as palladium-carbon catalyst or platinum catalysts under hydrogen atmosphere. This reaction may be carried out in an inert solvent such as MeOH, EtOH, and THF in the presence or absence of hydrogen chloride. If necessary, this reduction may be carried out under the adequate pressure in the range from about 0.5 to 10 kg/cm², preferably in the range from 1 to 6 kg/cm². Reaction temperature is generally in the range of −100° C. to 250° C., preferably in the range of 0° C. to the reflux temperature, but if necessary, lower or higher temperature can be employed. Reaction time is, in general, from 1 minute to 2 days, preferably from 20 minutes to 24 hours.

Scheme 3:

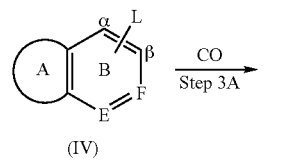

(IV)

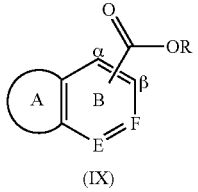

(IX)

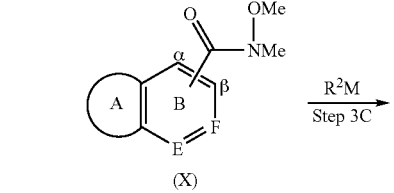

(X)

Route 1

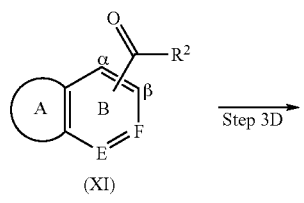

(XI)

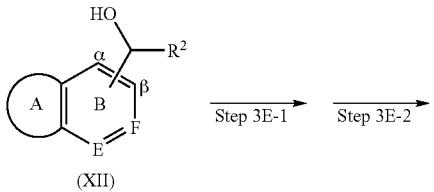

(XII)

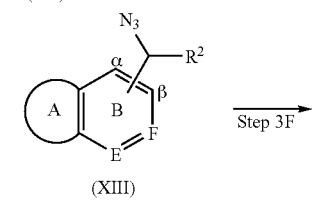

(XIII)

Route 2

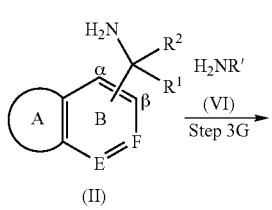

(II)

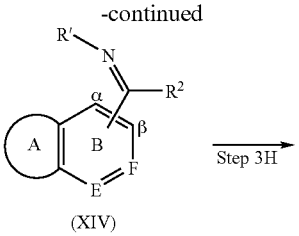

(XIV)

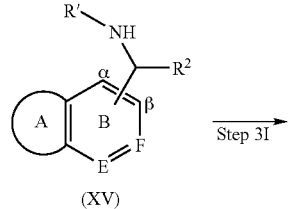

(XV)

Route 3

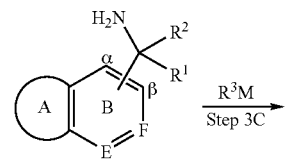

(II)

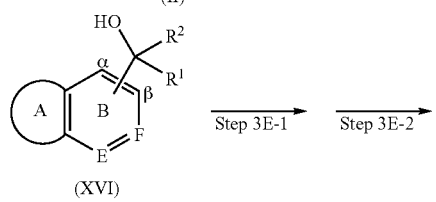

(XVI)

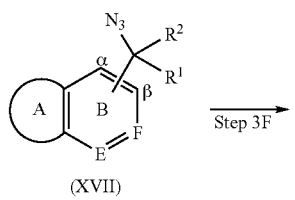

(XVII)

Route 4

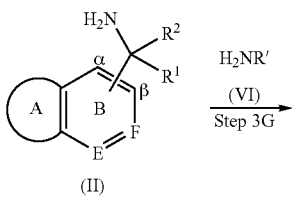

(II)

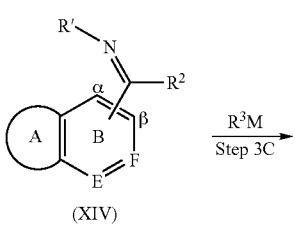

(XIV)

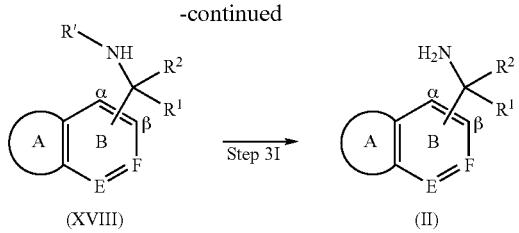

(XVIII) (II)

R': t-butylsulfinyl, phenethyl, NH$_2$, benzyl or diphenylmethyl
M: metal such as lithium or MgZ, Z: halogen When R$^2$ and R$^1$ are not H, the compound of formula (II) may be prepared from a compound of formula (IV).

Step 3A: In this Step, the compound of formula (IX) may be prepared by reacting the compound of formula (X) with carbon monoxide and alcohol (e.g. MeOH or EtOH) in the presence of a catalyst and/or base in an inert solvent. Examples of suitable catalysts include: palladium reagents, such as palladium acetate or palladium dibenzylacetone. Examples of suitable bases include: N,N-diisopropylethylamine, N-methylmorpholine or triethylamine. If desired, this reaction may be carried out in the presence or absence of an additive such as 1,1'-bis(diphenylphosphino)ferrocene, triphenylphosphine or 1,3-bis-(diphenylphosphino)propane (DPPP). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone; nitromethane; DMF; sulfolane; DMSO; NMP; 2-butanone; acetonitrile; halogenated hydrocarbons such as DCM, dichloroethane or chloroform; or ethers, such as THF or 1,4-dioxane. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from about 50° C. to 80° C. The time required for the reaction may also vary widely, depending on many factors, notably the reaction temperature and the nature of the reagents and solvent employed. However, provided that the reaction is effected under the preferred conditions outlined above, a period of 30 minutes to 24 hours, more preferably 1 hour to 10 hours, will usually suffice.

Step 3B-1: In this Step, an acid compound may be prepared by hydrolysis of the compound of formula (IX) in a solvent. The hydrolysis may be carried out by conventional procedures. In a typical procedure, the hydrolysis carried out under the basic condition in the presence of water, suitable bases include, for examples, sodium hydroxide, potassium hydroxide or lithium hydroxide. Suitable solvents include, for example, alcohols such as MeOH, EtOH, propanol, butanol, 2-methoxyethanol or ethylene gylcol; ethers such as THF, DME or 1,4-dioxane; amides such as DMF or hexamethylphosphorictriamide; or sulfoxides such as DMSO. This reaction may be carried out at a temperature in the range from −20 to 100° C., usually from 20° C. to 65° C. for 30 minutes to 24 hours, usually 60 minutes to 10 hours. The hydrolysis may also be carried out under an acid condition, e.g. in the presence of hydrogen halides, such as hydrogen chloride and hydrogen bromide; sulfonic acids, such as p-toluenesulfonic acid and benzenesulfonic acid; pyridium p-toluenesulfonate; and carboxylic acid, such as acetic acid and trifluoroacetic acid. Suitable solvents include, for example, alcohols such as MeOH, EtOH, propanol, butanol, 2-methoxyethanol, and ethylene gylcol; ethers such as THF, DME and 1,4-dioxane; amides such as DMF and hexamethylphosphorictriamide; and sulfoxides such as DMSO. This reaction may be carried out at a temperature in the range from −20 to 100° C., usually from 20° C. to 65° C. for 30 minutes to 24 hours, usually 60 minutes to 10 hours.

Step 3B-2: In this step, an amide compound of formula (X) can be prepared from the compound of 3B-1 by the same procedure as Step 1.

Step 3C: In this Step, the compound of formula (X$^1$) can be prepared by reaction of the compound of formula (X) with an organometallic reagent R$^2$M. R$^2$M can be prepared by reaction of a halide compound of R$^2$. For example, R$^2$M, in which M represents MgZ, can be generated with stirring Mg and R$^2$Z, dibromoethane and I$_2$ under warming condition from the range of between 30-80° C. This reaction may be carried out in the presence of an organometallic reagent or a metal. Examples of suitable organometallic reagents include alkyllithiums such as n-butyllithium, sec-butyllithium or tert-butyllithium; aryllithiums such as phenyllithium or lithium naphtilide. Examples of suitable metal include magnesium. Preferred inert solvents include, for example, hydrocarbons, such as hexane; ethers, such as diethyl ether, diisopropyl ether, DME, THF or 1,4-dioxane; or mixtures thereof. Reaction temperature is generally in the range of −100 to 50° C., preferably in the range of from −100° C. to room temperature. Reaction time is, in general, from 1 minute to a day, preferably from 1 hour to 10 hours.

Step 3D: In this Step, a compound of formula (XII) can be prepared by reduction of the compound of formula (XI). The reduction of the carbonyl group of compound (XI) may be carried out by conventional procedures. In a typical procedure, the reduction is carried out by treatment with lithium aluminum hydride, lithium borohydride or boran in a suitable inert solvent. Suitable solvents include, for example, ethers such as THF, DME or 1,4-dioxane. This reaction may be carried out at a temperature in the range from −20 to 100° C., usually from 20° C. to 65° C. for 30 minutes to 24 hours, usually 60 minutes to 10 hours. An alternative reduction procedure may be carried out by treatment with a reduction agent such as BH$_3$Me$_2$S complex having (R)-3,3-diphenyl-1-methylpyrrolidino[1,2,C]-1,3,2-oxazaborole as a ligand. Suitable inert solvents include THF. The reaction may be carried out at a temperature of −10° C., for 30 minutes to 24 hours, usually 60 minutes to 10 hours.

Step 3E-1: In this Step, a compound of formula (XII) may be converted to a compound with a leaving group under conditions known to those skilled in the art. For example, the hydroxy group of the compound of formula (XII) may be converted to the chloride using a chlorinating agent, e.g. thionyl chloride, oxalyl chloride in the presence or absence of an inert solvent, e.g. halogenated hydrocarbons such as methylene chloride, chloroform, carbon tetrachloride or 1,2-dichloroethane; or ethers such as diethyl ether, diisopropyl ether, THF or 1,4-dioxane; DMF or DMSO. For another example, the hydroxy group of the compound of formula (XII) may be converted to the sulfonate group using a sulfonating agent, e.g. para-toluenesulfonyl chloride, para-toluenesulfonic anhydride, methanesulfonyl chloride, methanesulfonic anhydride, trifluoromethanesulfonic anhydride in the presence of, or absence of a base, e.g. an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine or dimethylaminopyridine in the presence or absence of an inert solvent, e.g. aliphatic hydrocarbons, such as hexane, heptane or petroleum ether; aromatic hydrocarbons, such as benzene, toluene, o-dichlorobenzene, nitrobenzene, pyridine or xylene; halogenated hydrocarbons such as methylene chloride, chloroform, carbon tetrachloride or 1,2-dichloroethane; ethers such as diethyl ether, diisopropyl ether, THF or 1,4-dioxane; DMF or DMSO.

Step 3E-2: A compound of formula (XIII) may be prepared by azido introduction. The compound obtained in the Step 3E-1 may be treated with diphenylphosphoryl azide (DPPA), sodiumazide, or $HN_3$ in the presence of dialkyl azodicarboxylate such as diethyl azodicarboxylate (DEAD) and phosphine reagent such as triphenylphosphine. Preferably, this reaction may be carried out in an inert solvent. Preferred inert solvents include, but are not limited to, THF, diethyl ether, DMF, benzene, toluene, xylene, o-dichlorobenzene, nitrobenzene, DCM, 1,2-dichloroethane or DME; or mixtures thereof. The reduction may be carried out in the presence of a suitable reducing agent such as lithium aluminum hydride, sodium borohydride, triethyl phosphite, triphenylphosphine, zinc, dibutyl tinhydride or diboran in an inert solvent selected form, but not limited to, THF, diethyl ether, MeOH, and EtOH. If desired, the reaction may be carried out under acidic conditions in the presence of hydrochloric acid or acetic acid. Reaction tempreature is generally in the range of –100 to 250° C., preferably in the range of 0° C. to the reflux temperature, but if necessary, lower or higher temperature can be employed. Reaction time is, in general, from 1 minute to a day, preferably from 20 minutes to 5 hours, however shorter or longer reaction times, if necessary, can be employed.

Step 3F: In this Step, a compound of formula (II) can be prepared by reduction of the azide compound of formula (XIII) with a reducing agent. This reaction may be carried out in the presence of a suitable reducing agent such as diboran, boran-methyl sulfide complex, or lithium aluminum hydride in an inert solvent such as THF or diethyl ether. The reaction may also be carried out in similar conditions to those described in Step 2D above. Reaction temperature is generally in the range of –100 to 250° C., preferably in the range of 0° C. to the reflux temperature, but if necessary, lower or higher temperature can be employed. Reaction time is, in general, from 1 minute to a day, preferably from 20 minutes to 5 hours, however shorter or longer reaction times, if necessary, can be employed. The reduction may also be carried out under known hydrogenation conditions such as in the presence of a metal catalyst such as Raney nickel catalysts in the presence or absence of hydrazine, palladium catalysts or platinum catalysts under hydrogen atmosphere. This reaction may be carried out in an inert solvent such as MeOH, EtOH, or THF, in the presence or absence of hydrogen chloride. If necessary, this reduction may be carried out under the adequate pressure in the range from about 0.5 to 10 kg/cm², preferably in the range from 1 to 6 kg/cm². Reaction temperature is generally in the range of –100° C. to 250° C., preferably in the range of 0° C. to the reflux temperature, but if necessary, lower or higher temperature can be employed. Reaction time is, in general, from 1 minute to 2 days, preferably from 20 minutes to 24 hours.

Step 3G: In this step, the compound of formula (XIV) can be prepared by coupling reaction of the compound of formula (XI) with the amine of formula (VI) by the method described in Step 2B above.

Step 3H: In this Step, a compound of formula (XV) can be prepared from the compound of formula (XIV) by the method described in Step 2C above.

Step 3I: In this step, a compound of the formula (II) can be prepared from the compound of formula (XV) by the method described in Step 2D above.

Scheme 4:

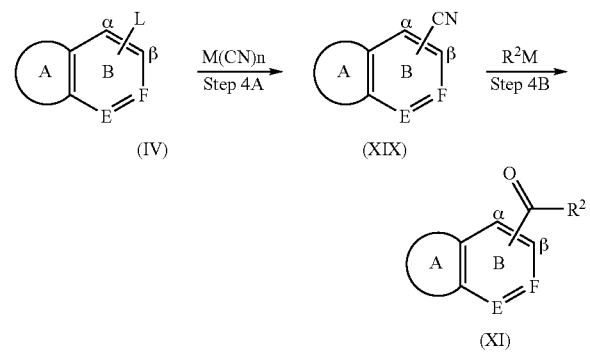

L: leaving group
M: MgZ, Z: halogen

When $R^2$ is not hydrogen and $R^1$ is hydrogen, a compound of formula (XI) can be prepared from a compound of formula (IV). This illustrates alternative preparation of compounds of formula (XI).

Step 4A: In this Step, a compound of formula (XIX) can be prepared by cyanating the compound of formula (IV) under a cyanating condition with a transition metal catalyst and metal cyanide reagent in an inert solvent. Examples of suitable solvents include: THF; 1,4-dioxane; DMF; acetonitrile; alcohols such as MeOH or EtOH; halogenated hydrocarbons such as DCM, 1,2-dichloroethane, chloroform or carbon tetrachloride; or DME. Suitable reagents include, for example, alkalimetal cyanide such as lithium cyanide, sodium cyanide, potassium cyanide, transition metal cyanide such as ferric(II) cyanide, cobalt(II) cyanide, copper(I) cyanide, copper(II) cyanide, zinc(II) cyanide ortrimethylsilyl cyanide. This reaction can be carried out in the presence of a suitable catalyst. There is likewise no particular restriction on the nature of the catalysts used, and any catalysts commonly used in reactions of this type can equally be used here. Examples of such catalysts include: tetrakis(triphenylphosphine)-palladium, bis(triphenylphosphine)palladium(II) chloride, copper(0), copper (I) acetate, copper(I) bromide, copper(I) chloride, copper (I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium(II) chloride, bisacetonitriledichloropalladium(0), bis(dibenzylideneacetone)palladium(0), tris (dibenzylideneacetone)dipalladium(0) or [1,1'-bis(diphenylphosphino)ferrocene]palladium(II) dichloride. Preferable catalysts are tetrakis(triphenylphosphine)-palladium, bis(triphenylphosphine)palladium(II) chloride, palladium(II) acetate, palladium(II) chloride, bisacetonitriledichloropalladium(0), bis(dibenzylideneacetone)palladium(0), tris(dibenzylideneacetone)dipalladium(0) or [1,1'-bis(diphenylphosphino)ferrocene]palladium(II) dichloride The reaction can be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl or triphenylarsine. The reaction can be carried out at a temperature of from 0° C. to 200° C., more preferably from 20° C. to 120° C. Reaction time is, in general, from 5 minutes to 48 hours, more preferably 30 minutes to 24 hours, will usually suffice. If necessary, microwave is applied to the reaction.

Step 4B: In this Step, a compound of formula (XI) can be prepared by reaction of the compound (XIX) with Grignard reagents, followed hydrolysis with aqueous solution of sodium bicarbonate or ammonium chloride. Examples of suitable Grignard reagents include; for examples, but not limited to, alkyl magnesium bromide such as methyl magnesium bromide, ethylmagnesium phenylmagnesium. Preferred inert solvents include, for example; ethers such as diethyl ether, diisopropyl ether, DME, THF or 1,4-dioxane; or mixtures thereof. Reaction temperature is generally in the range of −100 to 50° C., preferably in the range of from −100° C. to room temperature. Reaction time is, in general, from 1 minute to a day, preferably from 1 hour to 10 hours.

Scheme 5:

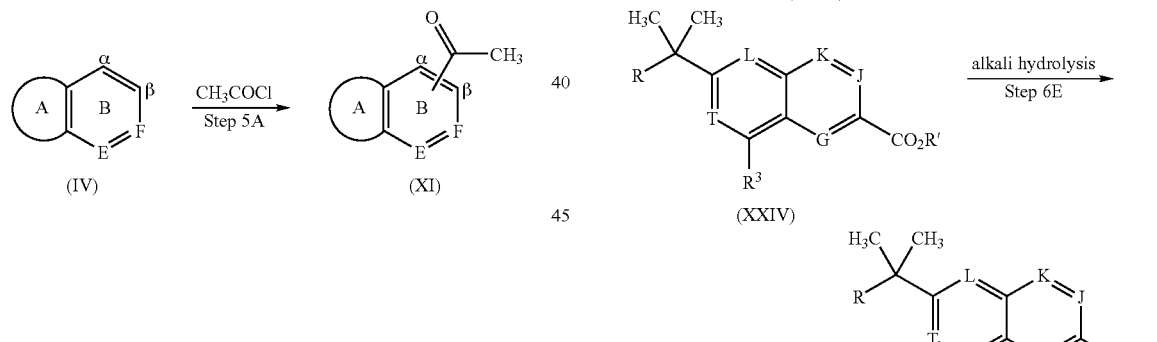

(IV)    (XI)

When $R^2$ is methyl, a compound of formula (XI) can be prepared from a compound of formula (IV). This illustrates alternative preparation of compounds of formula (XI).

Step 5A: In this Step, a compound of formula (XI) can be prepared by Friedel-Crafts reaction from the compound of formula (IV) under the acylation condition with Lewis acid catalyst and reagent in an inert solvent. Examples of suitable solvents include: halogenated hydrocarbons such as DCM, 1,2-dichloroethane, chloroform or carbon tetrachloride; or DME. Suitable reagent is acylchrolide. This reaction can be carried out in the presence of a suitable catalyst such as aluminium(III) chloride, titanium(IV)chloride or zirconium chloride. Reaction temperature is generally in the range of −100 to 90° C., preferably in the range of from room temperature to 70° C. Reaction time is, in general, from 1 minute to a day, preferably from 1 hour to 10 hours.

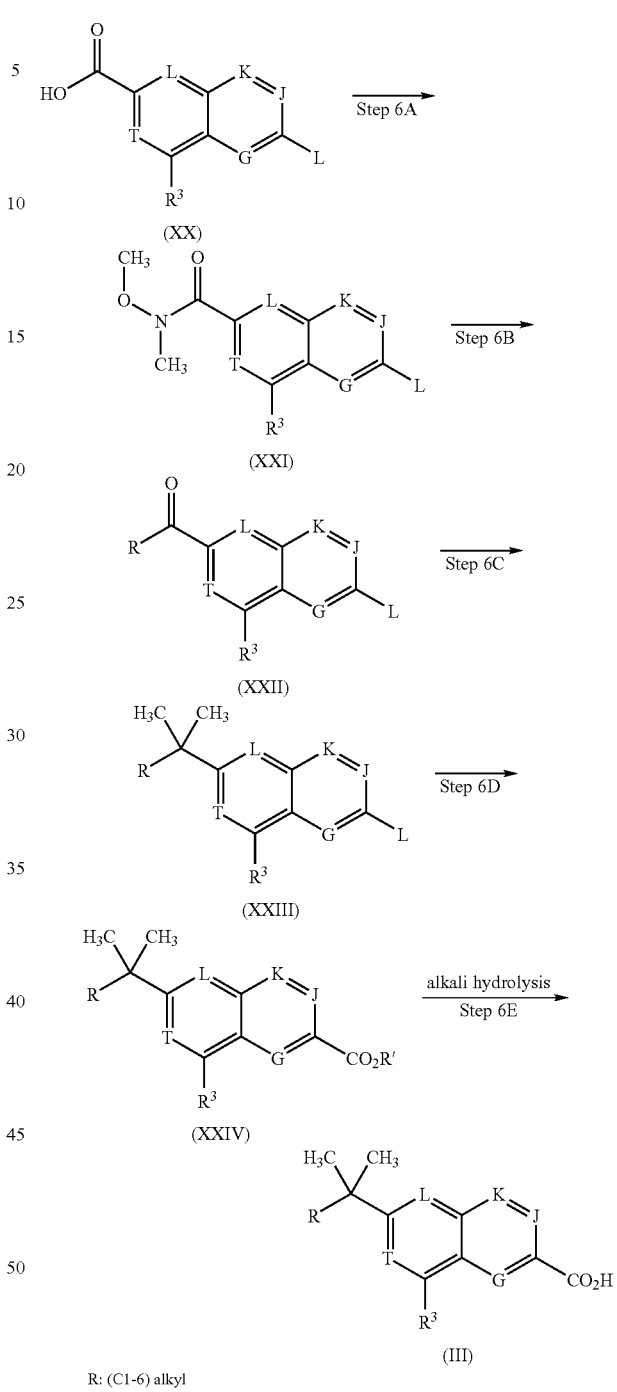

Step 6A: In this Step, an amide compound of formula (XXI) can be prepared from the compound of formula (XX) by the same procedure as Step 1.

Step 6B: In this Step, the ketone compound of formula (XXII) can also be prepared from the compound of formula (XXIII) by the same procedure as Step 3C.

Step 6C: In this Step, a compound of formula (XXIII) can also be prepared by an alkylation reaction of the compound of formula (XXII) with geminal-alkylating reagent in an inert solvent. Examples of preferred alkylating agents include trialkylmetals such as trimethylaluminum, triethylaluminum; alkylmagnesium halides such as methylmagnesium bromide in the presence of additive compound such as lithium bromide; dialkyltitanium halides such as dimethyltitanium dichloride prepared by dimethylzinc and titanium chloride; and are most preferably dimethyltitanium dichloride. Examples of preferred inert solvents for the reaction include halogenated hydrocarbons, such as DCM, 1,2-dichloroethane, chloroform or carbon tetrachloride; ethers, such as diethyl ether, diisopropyl ether, DME, THF and 1,4-dioxane; hydrocarbons, such as n-hexane, cyclohexane, benzene and toluene; or mixtures thereof. Reaction temperatures are generally in the range of from −100 to 200° C., preferably in the range of from −40° C. to 100° C. Reaction times are, in general, from 1 minute to a day, preferably from 1 hour to 10 hours.

Step 6D: In this Step, the compound of formula (XXIV) can also be prepared from the compound of formula (XXIV) by the same procedure as Step 3A.

Step 6E: In this Step, an acid compound of formula (III) can be prepared from the compound of formula (xxiv) by the same procedure as Step 3B-1 in a solvent.

Scheme 7:

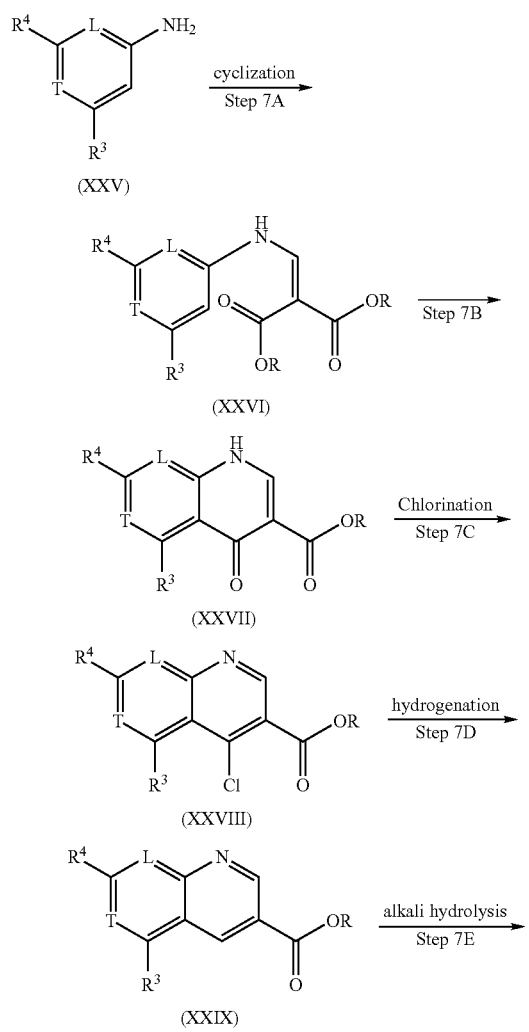

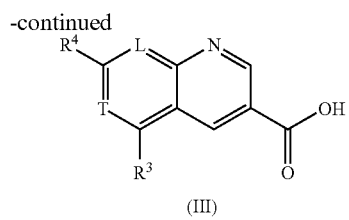

R: (C1-6)allyl

Step 7A: In this Step, a compound of formula (XXVI) can be prepared by N-substituted acrylation of the compound of formula (XXV) with dialkyl alkoxy methylenemalonate in a reaction inert solvent or without solvent. Examples of suitable solvents include alcohols such as MeOH, EtOH, propanol, butanol, 2-methoxyethanol, and ethylene glycol; ethers such as THF, DME, and 1,4-dioxane. As stated, this reaction may be performed without a solvent as well. The reaction can be carried out at a temperature in the range from 50° C. to 150° C. for 30 minutes to 24 hours, usually 60 minutes to 3 hours.

Step 7B: In this Step, a compound of formula (XXVII) can be prepared by thermal cyclization of the compound of formula (XXVI) in a reaction inert solvent. Examples of suitable solvents include ethers such as phenyl ether. This reaction can be carried out at a temperature in the range from 200 to 300° C. for 30 minutes to 24 hours, usually 250° C. for 30 minutes to 5 hours. (Journal of Medicinal chemistry, 1998, Vol 41, No 25.)

Step 7C: In this Step, a compound of formula (XXVIII) can be prepared by halogenation of the compound of formula (XXVII). The reaction is carried out under halogenation conditions with a halogenating reagent in a reaction inert solvent or without solvent. Examples of suitable solvents include THF, 1,4-dioxane, DMF, acetonitrile; halogenated hydrocarbons, such as DCM, 1,2-dichloroethane, chloroform or carbon tetrachloride and acetic acid. Examples of suitable halogenating reagents include phosphorus oxyhalide such as phosphorus oxychloride and phosphorus oxybromide. The reaction can be carried out at a temperature of from 0° C. to 200° C., more preferably from ambient temperature to 150° C. Reaction times are, in general, from 5 minutes to 48 hours, more preferably 30 minutes to 6 hours, will usually suffice.

Step 7D: In this Step, a dehalogenated compound of formula (XXIX) can be prepared by hydrogenation of the compound of formula (XXVIII) in a solvent. Hydrogenation reaction is carried out under, for example, known hydrogenolysis conditions in the presence of a metal catalyst under hydrogen atmosphere or in the presence of hydrogen sources such as formic acid or ammonium formate in a reaction inert solvent. If desired, the reaction is carried out under basic conditions, for example, in the presence of triethylamine. Preferable reagents is selected from, for example, nickel catalysts such as Raney nickel, palladium-carbon, palladiumhydroxide-carbon, platinumoxide, platinum-carbon, ruthenium-carbon, rhodium-aluminumoxide, tris[triphenyphosphine]rhodiumchloride. Examples of suitable reaction inert aqueous or non-aqueous organic solvents include alcohols, such as MeOH, EtOH; ethers, such as THF or 1,4-dioxane; acetone; dimethylformamide; halogenated hydrocarbons, such as DCM, dichloroethane or chloroform; and acetic acid or mixtures thereof. The reaction can be carried out at a temperature in the range from of 20° C. to 100° C., preferably in the range of 20° C.

to 60° C. Reaction times are, in general, from 10 minutes to 48 hours, preferably 30 minutes to 24 hours. This reaction can be carried out under hydrogen atmosphere at a pressure ranging from 1 to 100 atom, preferably from 1 to 10 atm. The preferable condition is the use of 5 or 10% palladium-carbon at ambient temperature for 1 to 24 hours under hydrogen atmosphere using a balloon.

Step 7E: In this Step, an acid compound of formula (III) can be prepared by hydrolysis of the compound of formula (XXIV) in a solvent by the method as described in Step 3B-1.

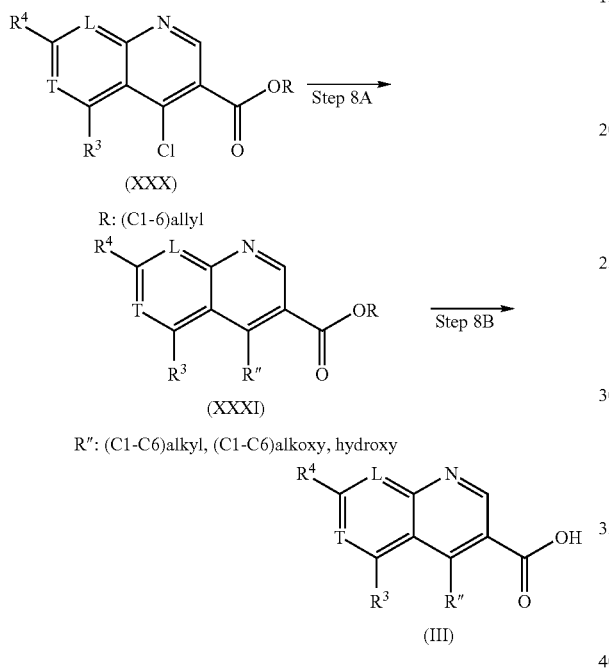

Step 8A: In this Step, a compound of formula (XXXI) can be prepared by coupling reaction of the compound of formula (XXX) with R—B(OH)$_2$ in a solvent. The coupling reaction may be carried out in the absence or presence of a base in a reaction inert solvent or without solvent. Examples of preferred base include an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, cesium carbonate or potassium carbonate, 2-tert-butylimino-2-diethylamino-1,3-dimethyl-perhydro-1,3,2-diazaphosphorine (BEMP), tert-butylimino-tri(pyrrolidino)phosphorane (BTPP), cesium fluoride (CsF), potassium fluoride, sodium hydride or potassium hydride, or an amine such as triethylamine, tributylamine, diisopropylethylamine, 2,6-lutidine, pyridine or dimethylaminopyridine. Examples of preferred reaction inert solvents include aromatic hydrocarbons, such as benzene, toluene, xylene, nitrobenzene and pyridine; halogenated hydrocarbons, such as methylene chloride, chloroform, carbon tetrachloride and dichloroethane; ethers, such as diethyl ether, diisopropyl ether, DME, TFA and 1,4-dioxane; EtOAc, acetonitrile, DMF, DMSO and water or mixtures thereof. Reaction temperatures are generally in the range of −100° C. to 250° C., more preferably in the range of 0° C. to reflux temperature. Reaction times are, in general, from 1 minute to a 10 day, more preferably from 20 minutes to 24 hours. This reaction may be carried out in the presence of a suitable catalyst. There is likewise no particular restriction on the nature of the catalyst used, and any catalyst commonly used in reactions of this type may equally be used here. Example of such catalysts include tetrakis(triphenylphosphine)palladium, bis(triphenylphosphine)palladium(0) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate palladium(II) acetate, palladium(II) chloride, bisacetonitriledichloropalladium(0), bis(dibenzylidenacetone)palladium(0), tris(dibenzylidenacetone)dipalladium(0) or [1,1'-bis(diphenylphosphino)ferrocene]palladium(II) dichloride. This reaction may be carried out in the presence of a suitable additive agent. Example of such additive agents include triphenylphosphine, tri-tert-butylphosphine, 1,1'-bis(diphenylphosphino)ferrocene, tri-2-furylphosphine, tri-o-tolylphosphine, 2-(dichlorohexylphosphino)biphenyl or triphenylarsine.

Step 8B: In this Step, an acid compound of formula (III) can be prepared by hydrolysis of the compound of formula (XXXI) in a solvent by the method described in Step 3B-1.

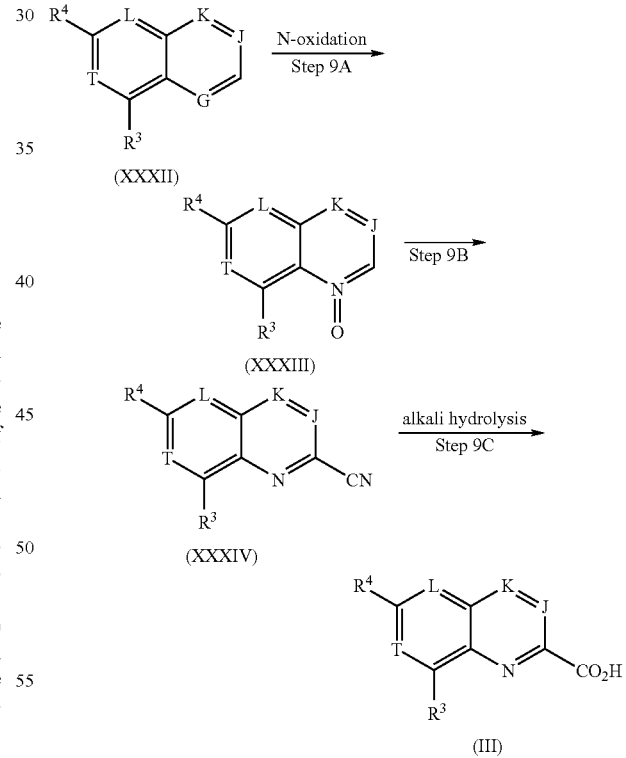

Step 9A: In this Step, a N-oxide compound of formula (XXXIII) can be prepared by oxidation of the compound of formula (XXXII) in a reaction inert solvent. The oxidation reaction may be carried out in the absence or presence of an additive agent in a reaction inert solvent. Examples of preferred oxidation reagents meta-chloroperbenzoic acid (mCPBA), hydrogen peroxide, peracetic acid. Examples of preferred reaction inert solvents include halogenated hydrocarbons, such as methylene chloride, chloroform, carbon tetrachloride and dichloroethane; ethers, such as diethyl ether, diisopropyl ether, DME, THF and 1,4-dioxane; acetonitrile, acetic acid and water or mixtures thereof. Reaction temperatures are generally in the range of 0° C. to 250° C., more preferably in the range of 0° C. to 100° C. Reaction times are, in general, from 1 minute to a 10 day, more preferably from 20 minutes to 6 hours. This reaction may be carried out in the presence of a suitable catalyst. There is likewise no particular restriction on the nature of the catalyst used, and any catalyst commonly used in reactions of this type may equally be used here. Examples of such catalysts include methyltrioxorhenium(VII), tungstic acid and sodium tungstate dehydrate.

Step 9B: In this Step, a cyano compound of formula (XXXIV) can be prepared by cyanation of the compound of formula (XXXIII) in a reaction inert solvent. Examples of preferred cyanation reagents include trimethylsilanecarbonitrile (TMSCN), the combimation of trimethylchlorosilane and sodium cyanide, the combination of acylating agents such as N,N-dimethylcarbamoyl chloride with trimethylsilanecarbonitrile (TMSCN). A preferred cyanation reagent is trimethylsilanecarbonitrile (TMSCN) in the presence of a base such triethylamine in a reaction inert solvent. Examples of preferred reaction inert solvents include halogenated hydrocarbons, such as methylene chloride, chloroform, carbon tetrachloride and dichloroethane; ethers, such as diethyl ether, DME, THF and 1,4-dioxane; acetonitrile, DMF, DMSO or mixtures thereof. Reaction temperatures are generally in the range of 0° C. to 250° C., more preferably in the range of 0° C. to 100° C. Reaction times are, in general, from 1 minute to 10 days, more preferably from 20 minutes to 24 hours.

Step 9C: In this Step, an acid compound of formula (III) can be prepared by hydrolysis of the cyano compound of formula (XXXIV) in a solvent. The hydrolysis can be carried out by conventional procedures. In a typical procedure, the hydrolysis may be carried out under basic conditions, e.g. in the presence of sodium hydroxide, potassium hydroxide or lithium hydroxide. Examples of suitable solvents include alcohols such as MeOH, EtOH, propanol, butanol, 2-methoxyethanol, and ethylene gylcol; ethers such as THF, DME, and 1,4-dioxane; amides such as DMF and hexamethylphospholictriamide; and sulfoxides such as DMSO. Preferable solvents are MeOH, EtOH, propanol, THF, DME, 1,4-dioxane, DMF and DMSO. This reaction can be carried out at a temperature in the range from –20 to 150° C., usually from 20° C. to 100° C. for 30 minutes to 24 hours, usually 60 minutes to 10 hours.

Scheme10:

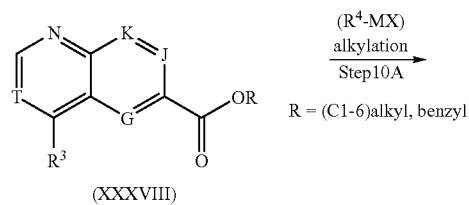

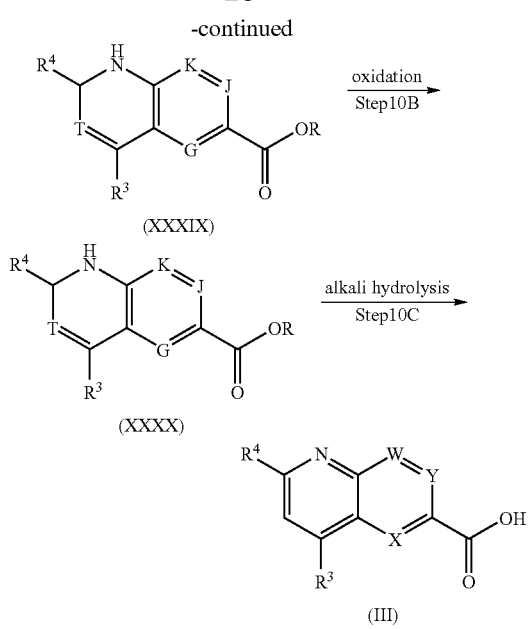

Step 10A: In this Step, a 1,2-dihydroquinoline compound of formula (XXXIX) can be prepared by alkylation of the compound of formula (XXXX) in a reaction inert solvent. The organometallic compound of formula R4-MX can be prepared by reaction of a halide compound of R, wherein R is alkyl. M represents metal such as lithium, or MgX, wherein X represents a hydrogen atom, a halogen atom such as, fluorine, chlorine, bromine or iodine. Examples of suitable organometallic reagents include alkyllithiums such as methyllithium, n-butyllithium, sec-butyllithium and tert-butyllithium; aryllithiums such as phenyllithium and lithium naphtilide; alkylmagnesium halide such as methylmagnesium halide, isopropylmagnesium halide, and t-butylmagnesium halide; arylmagnesium halide such as phenylmagnesium halide. Examples of preferred reaction inert solvents include hydrocarbons, such as hexane; ethers, such as diethyl ether, diisopropyl ether, IDME, THF and 1,4-dioxane; or mixtures thereof. Reaction temperatures are generally in the range of –100 to 100° C., preferably in the range of from –100° C. to room temperature. Reaction times are, in general, from 1 minute to a day, preferably from 1 hour to 24 hours.

Step 10B: In this Step, a compound of formula (XXXX) can be prepared by oxidation of the compound of formula (XXXIX) in a solvent. Examples of suitable oxidative agents include Cr-reagents, such as chromium trioxide ($CrO_3$), potassium chromate ($K_2CrO_4$), potassium dichromate ($K_2Cr_2O_7$); Mn-reagents, such as manganese dioxide ($MnO_2$), potassium permanganate ($KMnO_4$), quinine reagents, such as 2,3,5,6,-tetrachloro-1,4-benzoquinone (p-chloranil), 2,3-dichloro-5,6-dicyano-1,4-benzoquinone (DDQ), and air oxidation. Examples of suitable solvents include THF, 1,4-dioxane, acetone, DMF, acetonitrile, halogenated hydrocarbons (e.g., DCM, dichloroethane, chloroform), water; or mixtures thereof. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –78° C. to 100° C., more preferably from about –60° C. to 60° C. The time required for the reaction may also vary widely, depending on many factors, notably the reaction temperature and the nature of the reagents and solvent employed. However, provided that the reaction is effected under the preferred conditions outlined above, a period of 1 minute to 24 hours, more preferably 30 minutes to 12 hours, will usually suffice.

Step 10C: In this Step, an acid compound of formula (III) can be prepared by hydrolysis of the compound of formula (XXXX) in a solvent by the method as described in Step 3B-1.

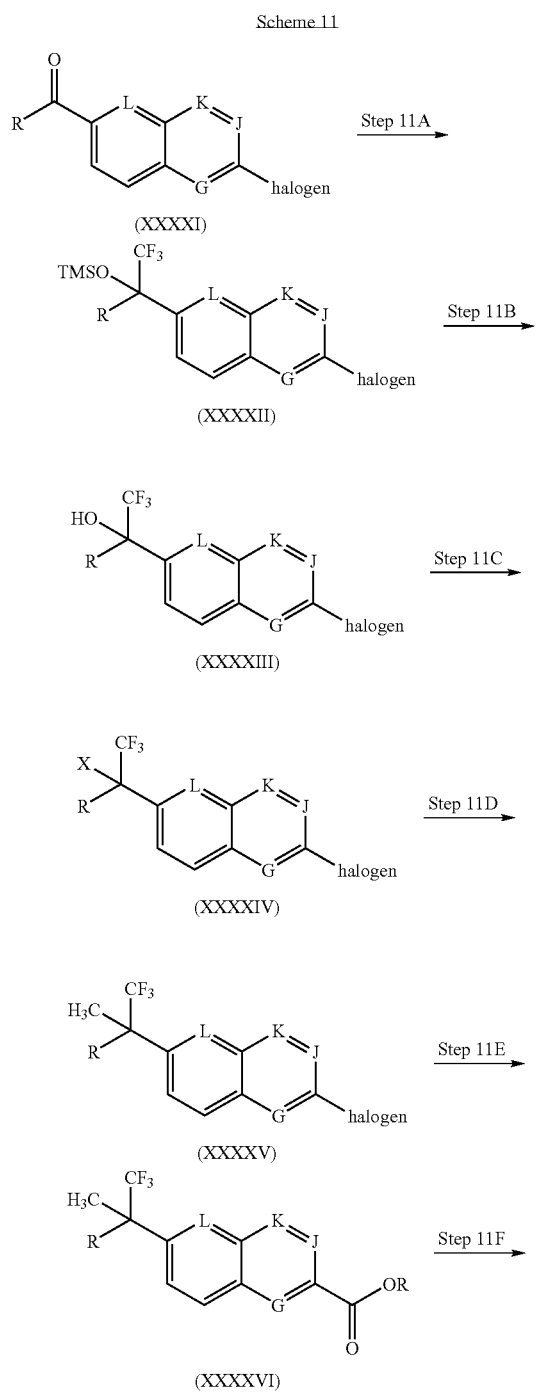

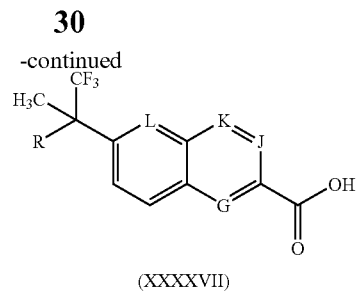

X: halogen, O-mesylate, O-tosylate, O-triflate
R = (C1-6)alkyl, benzyl

Step 11A: In this Step, a compound of formula (XXXXII) can be prepared by nucleophilic trifluoromethylation of formula (XXXXI) in a reaction inert solvent. Examples of preferred trifluoromethylation reagents include the combination of trifluoromethyltrimethylsilane (TMSCF$_3$) and initiator reagents. Examples of preferred catalytic initiator reagents include tetrabutylammonium fluoride (TBAF), cesium fluoride (CsF), lithium acetate (AcOLi), sodium acetate (AcONa), potassium acetate (AcOK), tetrabutylammonium acetate (AcO-nNBu$_4$), lithium pivalate (t-BuCO$_2$Li), lithium benzoate (PhCO$_2$Li), potassium t-butoxide (KO-tBu), and sodium t-butoxide (NaO-tBu). Examples of preferred reaction inert solvents include hydrocarbons, such as hexane, benzene, toluene; halogenated hydrocarbons, such as methylene chloride, chloroform, carbon tetrachloride and dichloroethane; ethers; such as diethyl ether, diisopropyl ether, 1,2-dimethoxyethane (DME), tetrahydrofuran and dioxane; acetonitrile, ethyl acetate, N,N-dimethylformamide (DMF), dimethylsulfoxide (DMSO) or mixtures thereof. Reaction temperatures are generally in the range of −78° C. to 200° C., more preferably in the range of −78° C. to 100° C. Reaction times are, in general, from 1 minute to 10 days, more preferably from 10 minutes to 24 hours.

Step 11B: In this Step, a hydroxyl compound of formula (XXXXIII) can be prepared by hydrolysis under acid condition of the O-trimethylsilyl compound of formula (XXXXII) in a solvent by the method as described in Step 3B-1.

Step 11C: In this Step, a compound of formula (XXXXIV) can be prepared by halogenation, O-mesylation, O-tosylation and O-triflate of the compound of formula (XXXXIII) in a reaction inert solvent or without solvent. The halogenation reaction can be carried out under halogenating reagent in an inert solvent or without solvent. Examples of suitable solvents include tetrahydrofuran, 1,4-dioxane, N,N-dimethylformamide, acetonitrile; halogenated hydrocarbons, such as dichloromethane, 1,2-dichloroethane, chloroform or carbon tetrachloride and acetic acid. Example of suitable halogenating reagents includes thionyl chloride, oxalyl chloride, phosphorus pentachloride, phosphorus tribromide; phosphorus oxyhalide such as phosphorus oxychloride and phosphorus oxybromide; lewis acids such as titanium chloride, tin chloride and aluminium chloride. The reaction can be carried out at a temperature of from −78° C. to 200° C., more preferably from −20° C. to 150° C. Reaction times are, in general, from 5 minute to 10 days, more preferably from 30 minutes to 24 hours. The O-mesylation, O-tosylation and O-triflate reactions can be carried out by the reaction of O-activating reagents with the compound of formula (XXXXIII) in the presence of a base in an inert solvent or without solvent. Examples of suitable O-activation reagents include methanesulfonyl chloride, p-toluenesulfonyl chloride, trifluoromethanesulfonyl chloride and trifluoromethanesulfonic acid anhydride. Examples of suitable base include alkyl lithium such as n-butyl lithium, sec-butyl lithium and tert-butyl lithium; potassium t-butoxide and sodium t-butoxide (NaO-tBu); triethylamine, diisopropylethylamine, 4-dimethylaminopyridine and pyridine. Examples of preferred reaction inert solvents include hydrocarbons, such as hexane, benzene, toluene; halogenated hydrocarbons, such as methylene chloride, chloroform, carbon tetrachloride and dichloroethane; ethers; such as diethyl ether, diisopropyl ether, 1,2-dimethoxyethane (DME), tetrahydrofuran and dioxane; acetonitrile, N,N-dimethylformamide (DMF), dimethylsulfoxide (DMSO) or mixtures thereof. The reaction can be carried out at a temperature of from −78° C. to 150° C., more preferably from −78° C. to 100° C. Reaction times are, in general, from 5 minute to 48 days, more preferably from 30 minutes to 24 hours.

Step 11D: In this Step, a compound of formula (XXXXV) can be prepared by an alkylation reaction of the compound of formula (XXXXVI) with alkylating reagent in an inert solvent. Examples of preferred alkylating agents include trialkylmetals such as trimethylaluminum, triethylaluminum; alkylmagnesium halides such as methylmagnesium bromide in the presence of additive compound such as lithium bromide; dialkyltitanium halides such as dimethyltitanium dichloride prepared by dimethylzinc and titanium chloride; and most preferably trimethylaluminum. Examples of preferred inert solvents for the reaction include halogenated hydrocarbons, such as dichloromethane (DCM), 1,2-dichloroethane, chloroform or carbon tetrachloride; ethers, such as diethyl ether, diisopropyl ether, 1,2-dimethoxyethane (DME), tetrahydrofuran (THF) and 1,4-dioxane; hydrocarbons, such as n-hexane, cyclohexane, benzene and toluene; or mixtures thereof. Reaction temperatures are generally in the range of from −100° C. to 200° C., preferably in the range of from −40° C. to 100° C. Reaction times are, in general, from 1 minute to 10 days, preferably from 1 hour to 24 hours.

Step 11E: In this Step, a compound of formula (XXXXVI) can be prepared by alkoxycarbonyl insertion reaction of the compound of formula (XXXXV) in a solvent by the method as described in Step 6E.

Step 11F: In this Step, an acid compound of formula (XXXXVII) can be prepared by hydrolysis of the compound of formula (XXXXVI) in a solvent by the method as described in Step 3B-1.

Alternatively carboxylic acids useful for the preparation of compounds of formula (I) can be prepared according to the following processes:

Scheme 12

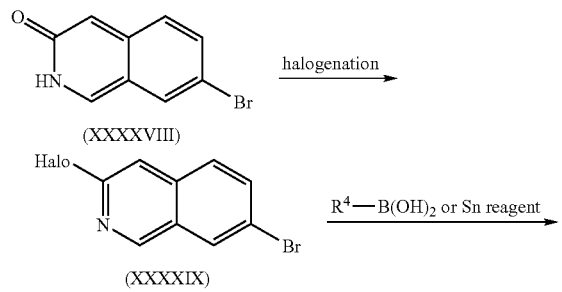

(XXXXVIII)

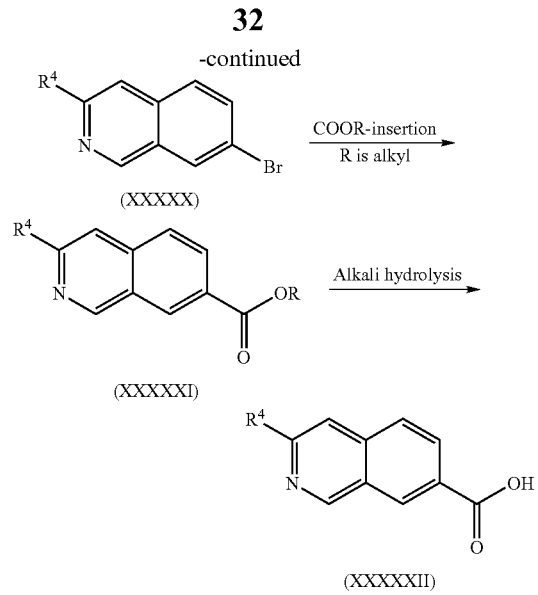

Other carboxylic acids useful for the preparation of compounds of formula (I) may be prepared according to methods well known to the skilled person, starting from commercially available material (see for example WO03/092695).

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

Method for Assessing Biological Activities

Human VR1 Antagonist Assay

VR1 antagonistic activity can be determined by the $Ca^{2+}$ imaging assay using human VR1 highly expressing cells. The cells that highly express human VR1 receptors are obtainable from several different conventional methods. The one standard method is cloning from human Dorsal Root Ganglion (DRG) or kidney according to the methods such as described in the journal article; Nature, 389, pp 816-824, 1997. Alternatively VR1 receptors highly expressing human keratinocytes are also known and published in the journal article (Biochemical and Biophysical Research Communications, 291, pp 124-129, 2002). In this article, human keratinocytes demonstrated VR1 mediated intracellular $Ca^{2+}$ increase by addition of capsaicin. Furthermore, the method to up regulate human VR1 gene, which is usually a silent gene or don't produce detectable level of VR1 receptors, is also available to obtain propriety cells. Such genetic modification method was described in detail; Nat. Biotechnol., 19, pp 440-445, 2001.

The cells that express human VR1 receptors were maintained in culture flask at 37° C. in an environment containing 5% $CO_2$ until use in the assay. The intracellular $Ca^{2+}$ imaging assay to determine VR1 antagonistic activities were done by following procedures.

The culture medium was removed from the flask and fura-2/AM fluorescent calcium indicator was added to the flask at a concentration of 5 μM in the medium. The flask was placed in $CO_2$ incubator and incubated for 1 hour. Then the cells expressing the human VR1 receptors were detached from the flask follow by washing with phosphate buffer saline, PBS(−) and re-suspended in assay buffer. The 80 μl of aliquot of cell suspension ($3.75 \times 10^5$ cells/ml) was added to the assay plate and the cells were spun down by centrifuge (950 rpm, 20° C., 3 minutes).

The compounds of the examples were tested in the Human VR1 antagonist assay described above. The $IC_{50}$ values are presented in the following table.

TABLE 1

| Example No. | $IC_{50}$ (nM) |
|---|---|
| A1 | 17.9 |
| A2 | 17 |
| A3 | 61.6 |
| A4 | 85.7 |
| A5 | 16.4 |
| A6 | 52 |
| A7 | 140 |
| A8 | 410 |
| A9 | 382 |
| B1 | 9.45 |
| B2 | 158 |
| B3 | 117 |
| B4 | 117 |
| B5 | 204 |
| B6 | 18.7 |
| B7 | 132 |
| C1 | 39.2 |
| C2 | 142 |
| C3 | 242 |
| C4 | 23 |
| C5 | 72 |
| C6 | — |
| C7 | 27 |
| C8 | 351 |
| C9 | 151 |
| C10 | 274 |
| C11 | 173 |
| C12 | 266 |
| C13 | 49.8 |
| C14 | 422 |
| C15 | 316 |
| C16 | 437 |
| C17 | 176 |
| C18 | 136 |
| C19 | — |
| C20 | 570 |
| D1 | 246 |
| capsazepine | 237-455 |

Gapsaicin Stimulation Assay

The capsaicin-induced changes in the intracellular calcium concentration were monitored using FDSS 6000 (Hamamatsu Photonics, Japan), a fluorometric imaging system. The cell suspension in Krebs-Ringer HEPES (KRH) buffer (115 mM NaCl, 5.4 mM KCl, 1 mM $MgSO_4$, 1.8 mM $CaCl_2$, 11 mM D-Glucose, 25 mM HEPES, 0.96 mM $Na_2HPO_4$, pH 7.3) were pre-incubated with varying concentrations of the test compounds or KRH buffer (buffer control) for 15 minutes at room temperature under the dark condition. Then capsaicin solution, which gives 300 nM in assay mixture, was automatically added to the assay plate by the FDSS 6000.

Acid Stimulation Assay

The Acid-induced changes in the intracellular calcium concentration were monitored using FDSS 6000 (Hamamatsu Photonics, Japan), a fluorometric imaging system. The cell suspension in resting buffer (HBSS supplemented with 10 mM HEPES, pH 7.4) were pre-incubated with varying concentrations of the test compounds or resting buffer (buffer control) for 15 minutes at room temperature under the dark condition. The cells were automatically added the stimulating solution (HBSS supplemented with MES, final assay buffer pH5.8) by the FDSS 6000. The $IC_{50}$ values of VR1 antagonists were determined from the half of the increase demonstrated by buffer control samples after acidic stimulation.

Determination of Antagonist Activity

The monitoring of the changes in the fluorescence signals ($\lambda ex=340$ nm/380 nm, $\lambda em=510$-520 nm) was initiated at 1 minute prior to the addition of capsaicin solution or acidic buffer and continued for 5 minute. The $IC_{50}$ values of VR1 antagonists were determined from the half of the increase demonstrated by buffer control samples after agonist stimulation.

Chronic Constriction Injury Model (CCI Model)

Male Sprague-Dawley rats (270-300 g; B. W., Charles River, Tsukuba, Japan) were used. The chronic constriction injury (CCI) operation was performed according to the method described by Bennett and Xie (Bennett, G. J. and Xie, Y. K. Pain, 33:87-107, 1988). Briefly, animals were anesthetized with sodium pentobarbital (64.8 mg/kg, i.p.) and the left common sciatic nerve was exposed at the level of the middle of the thigh by blunt dissection through biceps femoris. Proximal to the sciatic's trifurcation was freed of adhering tissue and 4 ligatures (4-0 silk) were tided loosely around it with about 1 mm space. Sham operation was performed as same as CCI surgery except for sciatic nerve ligation. Two weeks after surgery, mechanical allodynia was evaluated by application of von Frey hairs (VFHs) to the plantar surface of the hind paw. The lowest amount of force of VFH required to elicit a response was recorded as paw withdrawal threshold (PWT). VFH test was performed at 0.5, 1 and 2 hr post-dosing. Experimental data were analyzed using Kruskal-Wallis test followed by Dunn's test for multiple comparisons or Mann-Whitney U-test for paired comparison.

Parallel Artificial Membrane Permeation Assay (PAMPA)

Experiments were performed in 96-well acceptor and donor plates. Such 96-well system was described in *Journal of Medicinal Chemistry*, 1998, vol. 41, No. 7, 1007-1010. 4% phosphatidylcholine and 1% stearic acid in dodecane were used as artificial membrane material. The acceptor plate (96 well hydrophobic filter plate (MAIP N45, Millipore)) was prepared by adding 5 μL of artificial membrane material on the top of the filter and the plate was filled with 250 μL of 2-(N-morpholino)ethanesulfonic acid (MES) buffered Hank's balanced salt solution (HBSS) (pH 6.5). The donor plate (Transport Receiver plate (MATRNPS50, Millipore)) was filled with 300 μL of MES buffered HBSS (pH 6.5) containing 10 μM of the test compounds. The acceptor plate was placed onto the donor plate to form a "sandwich" and was incubated at 30° C. for 2.5 hours. After the incubation period, acceptor, donor and initial donor solution (reference) were analyzed via LC-MS/MS. Data were reported as the effective permeability value in $cm \times 10^6$/sec and the membrane retention value.

Human Dofetilide Binding

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells were homogenized using a Polytron homogenizer (at the maximum power for 20 seconds) and centrifuged at 48,000 g for 20 minutes at 4° C. The pellet was resuspended, homogenized and centrifuged once more in the same manner. The resultant supernatant was discarded and the final pellet was resuspended (10-fold volume of 50 mM Tris buffer) and homogenized at the maximum power for 20 seconds. The membrane homogenate was aliquoted and stored at −80° C. until use. An aliquot was used for protein concentration determination using a Protein Assay Rapid Kit and ARVO SX plate reader (Waflac). All the manipulation, stock solution and equipment were kept on ice at all time. For saturation assays, experiments were conducted in a total volume of 200 µl. Saturation was determined by incubating 20 µl of [$^3$H]-dofetilide and 160 µl of membrane homogenates (20-30 µg protein per well) for 60 min at room temperature in the absence or presence of 10 µM dofetilide at final concentrations (20 µl) for total or nonspecific binding, respectively. All incubations were terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity was quantified by liquid scintillation counting using Packard LS counter.

For the competition assay, compounds were diluted in 96 well polypropylene plates as 4-point dilutions in semi-log format. All dilutions were performed in DMSO first and then transferred into 50 mM Tris buffer (pH 7.5 at 25° C.) containing 1 mM MgCl$_2$, 10 mM KCl so that the final DMSO concentration became equal to 1%. Compounds were dispensed in triplicate in assay plates (4 µl). Total binding and nonspecific binding wells were set up in 6 wells as vehicle and 10 µM dofetilide at final concentration, respectively. The radioligand was prepared at 5.6× final concentration and this solution was added to each well (36 µl). The assay was initiated by addition of YSi poly-L-lysine Scintillation Proximity Assay (SPA) beads (50 µl, 1 mg/well) and membranes (110 µl, 20 µg/well). Incubation was continued for 60 min at room temperature. Plates were incubated for a further 3 hours at room temperature for beads to settle. Receptor-bound radioactivity was quantified by counting Wallac MicroBeta plate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical Journal, 74, pp 230-241). Before the day of experimentation, the cells were harvested from culture flasks and plated onto glass coverslips in a standard Minimum Essential Medium (MEM) medium with 10% Fetal Calf Serum (FCS). The plated cells were stored in an incubator at 37° C. maintained in an atmosphere of 95% O$_2$/5% CO$_2$. Cells were studied between 15-28 hrs after harvest.

HERG currents were studied using standard patch clamp techniques in the whole-cell mode. During the experiment the cells were superfused with a standard external solution of the following composition (mM); NaCl, 130; KCl, 4; CaCl$_2$, 2; MgCl$_2$, 1; Glucose, 10; HEPES, 5; pH 7.4 with NaOH. Whole-cell recordings was made using a patch clamp amplifier and patch pipettes which have a resistance of 1-3 MOhm when filled with the standard internal solution of the following composition (mM); KCl, 130; MgATP, 5; MgCl$_2$, 1.0; HEPES, 10; EGTA 5, pH 7.2 with KOH. Only those cells with access resistances below 15MΩ and seal resistances >1GΩ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol was applied to the cell to evoke membrane currents. The voltage protocol is as follows. The membrane was depolarized from a holding potential of −80 mV to +40 mV for 1000 ms. This was followed by a descending voltage ramp (rate 0.5 mV msec$^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10-20 min by a peristalic pump. Provided there were minimal changes in the amplitude of the evoked current response in the vehicle control condition, the test compound of either 0.3, 1, 3, 10 µM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There was a subsequent wash period of a 10-20 min to assess reversibility. Finally, the cells were exposed to high dose of dofetilide (5 µM), a specific IKr blocker, to evaluate the insensitive endogenous current.

All experiments were performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, was measured off line on the computer.

The arithmetic mean of the ten values of amplitude was calculated under vehicle control conditions and in the presence of drug. Percent decrease of $I_N$ in each experiment was obtained by the normalized current value using the following formula: $I_N=(1-I_D/I_C)\times 100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Drug-Drug Interaction Assay

This method essentially involves determining the percent inhibition of product formation from fluorescence probe at 3 µM of the each compound.

More specifically, the assay is carried out as follows. The compounds were pre-incubated with recombinant CYPs, 100 mM potassium phosphate buffer and fluorescence probe as substrate for 5 min. Reaction was started by adding a warmed NADPH generating system, which consist of 0.5 mM NADP (expect; for 2D6 0.03 mM), 10 mM MgCl$_2$, 6.2 mM DL-Isocitric acid and 0.5 U/ml Isocitric Dehydrogenase (ICD). The assay plate was incubated at 37° C. (expect; for 1A2 and 3A4 at 30° C.) and taking fluoresce reading every minutes over 20 to 30 min.

Data calculations were preceded as follows;
1. The slope (Time vs. Fluorescence units) was calculated at the linear region
2. The percentage of inhibition in compounds was calculated by the equation $$\{(v_o-v_i)/v_o\}\times 100 = \% \text{ inhibition}$$

Wherein
$v_o$=rate of control reaction (no inhibitor)
$v_i$=rate of reaction in the presence of compounds.

TABLE 2

Condition for drug-drug interaction assay.

| | 1A2 | 2C9 | 2C19 | 2D6 | 3A4 |
|---|---|---|---|---|---|
| Substrate | Vivid blue (Aurora) | MFC (Gentest) | Vivid blue (Aurora) | AMMC (Gentest) | Vivid red (Aurora) |
| Substrate (µM) | 10 | 30 | 10 | 1 | 2 |

TABLE 2-continued

Condition for drug-drug interaction assay.

|  | 1A2 | 2C9 | 2C19 | 2D6 | 3A4 |
|---|---|---|---|---|---|
| Enzyme (pmol) | 50 | 50 | 5 | 50 | 5 |
| EX./Em (λ) | 408/465 | 408/535 | 408/465 | 400/465 | 530/595 |

Intrinsic Clearance in HLM (Human Liver Microsomes)

Test compounds (1 μM) were incubated with 1 mM $MgCl_2$, 1 mM NADP+, 5 mM isocitric acid, 1 U/mL isocitric dehydrogenase and 0.8 mg/mL HLM (human liver microsomes) in 100 mM potassium phosphate buffer (pH 7.4) at 37° C. on a number of 384-well plates. At several time points, a plate was removed from the incubator and the reaction was terminated with two incubation volumes of acetonitrile. The compound concentration in supernatant was measured by LC/MS/MS system. The intrinsic clearance value ($CI_{int}$) was calculated using following equations:

$$CI_{int}(\mu l/min/mg\ protein) = (k \times incubation\ volume)/Protein\ concentration$$

$$k(min^{-1}) = -slope\ of\ ln(concentration\ vs.\ time)$$

Mono-Iodoacetate (MIA)-Induced OA Model

Male 6-weeks-old Sprague-Dawley (SD, Japan SLC or Charles River Japan) rats were anesthetized with pentobarbital. Injection site (knee) of MIA was shaved and cleaned with 70% EtOH. Twenty-five μl of MIA solution or saline was injected in the right knee joint using a 29G needle. The effect of joint damage on the weight distribution through the right (damaged) and left (untreated) knee was assessed using an incapacitance tester (Linton Instrumentation, Norfolk, UK). The force exerted by each hind limb was measured in grams. The weight-bearing (WB) deficit was determined by a difference of weight loaded on each paw. Rats were trained to measure the WB once a week until 20 days post MIA-injection. Analgesic effects of compounds were measured at 21 days after the MIA injection. Before the compound administration, the "pre value" of WB deficit was measured. After the administration of compounds, attenuation of WB deficits was determined as analgesic effects.

Complete Freund's Adjuvant (CFA) Induced Thermal and Mechanical Hyperalgesia in Rats Thermal Hyperalgesia Male 6-week-old SD rats were used. Complete Freund's adjuvant (CFA, 300 μg of *Mycobacterium Tuberculosis* H37RA (Difco, Mich.) in 100 μL of liquid paraffin (Wako, Osaka, Japan)) was injected into the plantar surface of hind paw of the rats. Two days after CFA-injection, thermal hyperalgesia was determined by method described previously (Hargreaves et al., 1988) using the plantar test apparatus (Ugo-Basil, Varese, Italy). Rats were adapted to the testing environment for at least 15 min prior to any stimulation. Radiant heat was applied to the plantar surface of hind paw and paw withdrawal latencies (PWL, seconds) were determined. The intensity of radiant heat was adjusted to produce the stable PWL of 10 to 15 seconds. The test compound was administered in a volume of 0.5 mL per 100 g body weight. PWL were measured after 1, 3 or 5 hours after drug administration.

Mechanical Hyperalgesia

Male 4-week-old SD rats were used. CFA (300 μg of *Mycobacterium Tuberculosis* H37RA (Difco, Mich.) in 100 μL of liquid paraffin (Wako, Osaka, Japan)) was injected into the plantar surface of hind paw of the rats. Two days after CFA-injection, mechanical hyperalgesia was tested by measuring paw withdrawal threshold (PWT, grams) to pressure using the analgesy-Meter (Ugo-Basil, Varese, Italy). The animals were gently restrained, and steadily increasing pressure was applied to the dorsal surface of a hind paw via a plastic tip. The pressure required to elicit paw withdrawal was determined. The test compound was administered in a volume of 0.5 mL per 100 g body weight. PWT were measured after 1, 3 or 5 hours after drug administration.

Drug Substance

Pharmaceutically acceptable salts of the compounds of formula (I) include the acid addition and base salts thereof.

Suitable acid addition salts are formed from acids which form non-toxic salts. Examples include acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, EtOH. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labeled compounds of formula (I). "Tautomers" or "tautomeric isomers" refer to compounds that are interchangeable forms of a particular compound structure, and that vary in the displacement of hydrogen atoms and electrons, which are illustrated as follows;

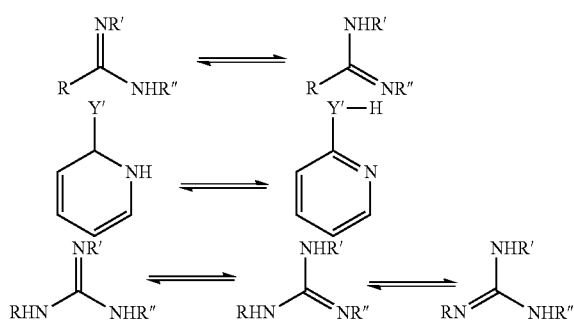

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:
(i) where the compound of formula (I) contains a carboxylic acid functionality (—COOH), an ester thereof, for example, replacement of the hydrogen with $(C_1\text{-}C_8)$alkyl;
(ii) where the compound of formula (I) contains an alcohol functionality (—OH), an ether thereof, for example, replacement of the hydrogen with $(C_1\text{-}C_6)$alkanoyloxymethyl; and
(iii) where the compound of formula (I) contains a primary or secondary amino functionality (—NH$_2$ or —NHR where R is not H), an amide thereof, for example, replacement of one or both hydrogens with $(C_1\text{-}C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, EtOH, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colorants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably. to a pH of from 3 to 9), but, for some applications, they may be more suitably formulated as a sterile non-aqueous solution or as powdered a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for use with needle-free injection administration comprise a compound of the invention in powdered form in conjunction with a suitable vehicle such as sterile, pyrogen-free water.

Formulations for parenteral administration may be formulated to be immediate and/or modified controlled release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified controlled release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, EtOH, aqueous EtOH, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, EtOH and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified controlled release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 10 mg of the compound of formula (I). The overall daily dose will typically be in the range 1 µg to 10 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified controlled release. Modified release formulations include delayed-, sustained-, pulsed-, controlled-, targeted and programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the compounds of the invention is typically in the range 0.1 mg to 3000 mg, preferably from 1 mg to 500 mg, depending, of course, on the mode of administration. For example, oral administration may require a total daily dose of from 0.1 mg to 3000 mg, preferably from 1 mg to 500 mg, while an intravenous dose may only require from 0.1 mg to 1000 mg, preferably from 0.1 mg to 300 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

A VR1 antagonist may be usefully combined with another pharmacologically active compound, or with two or more other pharmacologically active compounds, particularly in the treatment of pain. For example, a VR1 antagonist, particularly a compound of formula (I), or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolin one;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α, 3α, 5α)(3-a mino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid, (3R,4R,5R)-3-amino-4,5-dimethyl-octanoic acid, (2S)-2-Amino-4-ethyl-2-methylhexanoic acid and (2S)-2-aminomethyl-5-ethyl-heptanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, iitoxetine, dapoxetine, nefazodone, cericiamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R, 3S)-3-amino-4-hydroxy-1-(5-thiazolyl)butyl]thio]-4-chlorobenzonitrile, (2S, 4R)-2-amino-4-[[2-chlor o-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine;

a 5-HT3 antagonist, such as ondansetron;

and the pharmaceutically acceptable salts and solvates thereof.

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC) and reaction times were given for illustration only; melting points (mp) given were uncorrected (polymorphism may result in different melting points); the structure and purity of all isolated compounds were assured by at least one of the following techniques: TLC (Merck silica gel 60 $F_{254}$ precoated TLC plates), mass spectrometry, nuclear magnetic resonance spectra (NMR), infrared red absorption spectra (IR) or microanalysis. Yields were given for illustrative purposes only. Flash column chromatography was carried out using Merck silica gel 60 (230-400 mesh ASTM) or Fuji Silysia amino bounded silica (Chromatorex, 30-50 uM) or Biotage amino bounded silica (35-75 μm, KP—NH) or Biotage silica (32-63 μm, KP-Sil). The purification using HPLC was perfomed by the following apparatus and conditions. Apparatus: UV-trigger preparative HPLC system, Waters (Column: XTerra MS C18, 5 um, 19×50 mm or 30×50 mm), Detector: UV 254 nm Conditions: $CH_3CN$/0.05% HCOOH aqueous solution or $CH_3CN$/0.01% $NH_3$ aqueous solution; 20 ml/min (19×50 mm) or 40 ml/min (30×50 mm) at ambient temperature. Microwave apparatus used in the reaction was Emrys optimizer (Personal chemistry). Optical rotation was measured by P-1020 (Jasco). Low-resolution mass spectral data (EI) were obtained on a Integrity (Waters) mass spectrometer. Low-resolution mass spectral data (ESI) were obtained on a ZMD (Micromass) mass spectrometer. NMR data were determined at 270 MHz (JEOL JNMLA 270 spectrometer) or 300 MHz (JEOL JNMLA300 spectrometer) using deuterated chloroform (99.8% D) or DMSO (99.9% D) as solvent unless indicated otherwise, relative to tetramethylsilane (TMS) as internal standard in parts per million (ppm); conventional abbreviations used were: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; bp (boiling point), mp (melting point), L (liter(s)), ml (milliliter(s)), g (gram(s)), mg (milligram(s)), mol (moles), mmol (millimoles), eq. (equivalent(s)), quant. (quantitative yield), sat. (saturated), aq (aqua). In the following Examples, "Me" means methyl and "Et" means ethyl.

Preparation

Amines

Amines used in the following Examples were prepared by the methods below, as a free compound or a salt.

Amine 1:
(1R)-1-(1H-1,2,3-benzotriazol-6-yl)ethanamine, monohydrochloride

Step A1A: 1-(1H-1,2,3-benzotriazol-6-yl)ethanone

1A) A mixture of 1-(3,4-diaminophenyl)ethanone (Indian Journal of Chemistry, Section B: Organic Chemistry Including Medicinal Chemistry (1985), 24B(5), 574-7., 3.6 g, 24.0 mmol), acetic acid (5 ml, 48.0 mmol) and water (15 ml) was stirred for 10 minutes at 65° C. and the mixture was placed at 5° C. After quenching with water solution of sodium nitrile (1.90 g, 27.6 mmol), the mixture was stirred for 1 hour at 80° C. followed by being cooled to 5° C. with stirring for 3 hours. The formed precipitate was collected and dried to give 2.65 g (68%) of the title compound. $^1$H NMR (270 MHz, DMSO-$d_6$) δ ppm 2.71 (3H, s), 3.36 (1H, brs), 7.90-8.07 (2H, m), 8.69 (1H, s). MS (ESI) m/z 477 (M−H)$^−$, 479 (M+H)$^+$

Step A1B:
(1R)-1-(1H-1,2,3-benzotriazol-6-yl)ethanamine hydrochloride

1B) To a THF (25 ml) solution of 1-(1H-1,2,3-benzotriazol-6-yl)ethanone (1.85 g, 11.5 mmol), (R)-(+)-2-methyl-2-propanesulfinylamide (2.30 g, 18.9 mmol) and titanium(IV) ethoxide (25 ml) were added and the mixture was stirred for 24 hours at 70° C. Then, the mixture was cooled to 0° C. and sodium borohydride (1.5 mg, 40 mmol) was added. After stirring for 2 hours, water and EtOH were added to the mixture with stirring for 1 hour at room temperature. Filtration, evaporation gave N-[(1R)-1-(1H-1,2,3-benzotriazol-6-yl)ethyl]-2-methylpropane-2-sulfinamide (99% d.e.) (MS (ESI) m/z 265 (M−H)$^−$, 267 (M+H)$^+$) which was treated with hydrochloric acid-MeOH (2.0 M, 15.0 ml) and 1,4-dioxane (15.0 ml) for 1.5 hours at room temperature. Then, the reaction mixture was evaporated and diethyl ether was added to form a precipitate, which was collected, washed with diethyl ether to give 1.26 g (68%) of the title compound. MS (ESI) m/z 161 (M−H)−

Amine 2: (1R)-1-(1H-1,2,3-benzotriazol-6-yl)propan-1-amine, mono hydrochloride

A mixture of 1H-1,2,3-benzotriazole-6-carboxylic acid (Aldrich, 500 mg, 3.1 mmol), N,O-dimethylhydroroxylamine hydrochloride (Aldrich, 299 mg, 3.1 mmol), HBTU (1.5 g, 4.0 mmol) and trimethylamine (1.28 ml, 9.2 mmol) were added and the mixture was stirred for 18 hours at room temperature. Then, evaporation, purification through silica gel column chromatography eluting with DCM/MeOH (10:1) to give N-methoxy-N-methyl-1H-1,2,3-benzotriazole-6-carboxamide (LC-MS (MS (ESI) m/z 205 (M−H)−, 207 (M+H)+). To a THF (50 ml) solution of the product was added 0.96 M hexane solution of ethylmagnesium bromide (15 ml, 14.4 mmol) at 0° C., and the mixture was stirred for 16 hours at room temperature. Then the reaction was quenched with aqueous solution of ammonium chloride and the product was extracted with AcOEt, washed with brine, dried over magnesium sulfate. Then, evaporation in vacuo gave 1-(1H-1,2,3-benzotriazol-6-yl)propan-1-one (LC-MS (MS (ESI) m/z 174 (M−Hy, 176 (M+H)+).

To a THF (7 ml) solution of the compound of the product and (R)-(+)-2-methyl-2-propanesulfinylamide (521 mg, 4.3 mmol), titanium(IV) ethoxide (5 ml) was added and the mixture was reacted under microwave condition for 2 hours at 80° C. After the confirmation of imine generation utilizing with LC-MS (MS (ESI) m/z 277 (M−H)−, 279 (M+H)+), the mixture was cooled to 0° C. and sodium borohydride (413 mg, 10.9 mmol) was added to the reaction mixture and stirred for 1 hour at the temperature. The reaction was partitioned with water and EtOH, then stirred for 30 min at room temperature. The mixture was filtrated through Celite pad, and the filtrate was evaporated, concentrated in vacuo to give N-[(1R)-1-(1H-1,2,3-benzotriazol-5-yl)propyl]-2-methylpropane-2-sulfinamide(50% d.e.) (MS (ESI) m/z 279 (M−H)−, 281 (M+H)+). To the 1,4-dioxane solution of the compound was added hydrochloric acid-MeOH (2.0 M, 10.0 ml) and (10.0 ml), and the mixture was stirred for 2 hours at room temperature. Then the reaction mixture was evaporated in vacuo and diethyl ether was added to precipitate amine hydrochloride. The precipitate was then filtered and washed with diethyl ether to give the title compound (131 mg, 5 steps 20%) (MS (ESI) m/z 176 (M−H)−, 178 (M+H)+).

Amine 3: 1H-indazol-5-methanamine

1H-Indazol-5-methanamine was synthesized as described in WO 2004108133 as an HCl salt.

Amine 4: 5-(1-aminoethyl)-1,3-dihydro-2H-indol-2-one, mono hydrochloride

To a MeOH (30 ml) solution of 5-[(1E)-N-hydroxyethanimidoyl]-1,3-dihydro-2H-indol-2-one (0.5 g, 2.6 mmol; WO 2004108133), Raney Nickel and aqueous solution of ammonium hydroxide (10 ml) were added and the mixture was stirred for 9 hours under hydrogen (4.0 kgf/cm$^2$). Then, the reaction was filtered off and the filtrate was evaporated to give 5-(1-aminoethyl)-1,3-dihydro-2H-indol-2-one as a free form. Then, the amine was treated with MeOH solution of 10% of chloride and recrystallized from MeOH/diethyl ether to give the title compound as a white solid. MS (ESI) m/z 177 (M+H)+

Amine 5: 5-(1-aminoethyl)-1,3-dihydro-2H-benzimidazol-2-one, mono hydrochloride

Step A5A: N-[1-(4-Amino-3-nitrophenyl)ethyl]-2-methylpropane-2-sulfinamide

A mixture of 1-(4-amino-3-nitrophenyl)ethanone (500 mg, 2.78 mmol, J. Med. Chem. 1998, 41, 1777-1788), 2-methylpropane-2-sulfinamide (674 mg, 5.56 mmol) in THF (25 ml) was added titanium(IV) ethoxide (1.75 ml, 8.34 mmol) at room temperature. The mixture was stirred at 80° C. for 24 hours. After cooling to room temperature, sodium borohydrate (316 mg, 8.34 mmol) was added to the mixture at room temperature. The mixture was stirred at room temperature for 14 hours. The mixture was quenched with MeOH (6 ml), poured into saturated sodium hydrogencarbonate aqueous solution (20 ml), extracted with EtOAc (150 mL×2). The combined organic layer was washed with brine (50 ml), dried over sodium sulfate and concentrated. The residue was chromatographed on a column of silica gel with hexane-EtOAc (1:2) as eluent to afford 675 mg (85%) of the title compound as a yellow solid. $^1$H NMR (300 MHz, DMSO-d$_6$) δ ppm 1.11 (9H, s), 1.37 (3H, d, J=6.6 Hz), 4.33-4.24 (1H, m), 5.64 (1H, d, J=6.6 Hz), 6.99 (1H, d, J=8.8 Hz), 7.40 (2 H, s), 7.45 (1H, d, J=8.8 Hz), 7.97 (1H, s). MS (ESI) m/z 286 (M+H)+, 284 (M−H)−.

Step A5B: N-[1-(3,4-Diaminophenyl)ethyl]-2-methylpropane-2-sulfinamide

A mixture of N-[1-(4-amino-3-nitrophenyl)ethyl]-2-methylpropane-2-sulfinamide (670 mg, 2.35 mmol) and 10% palladium-carbon (70 mg) in EtOH (50 ml) was stirred under hydrogen (4 atm) at room temperature for 6 hours. The mixture was filtered through a pad of Celite. The filtrate was concentrated to give 598 mg of the title compound as a brown solid. $^1$H NMR (300 MHz, CDCl$_3$) δ ppm 1.22 (9H, s), 1.45 (3H, d, J=6.6 Hz), 3.50-3.32 (4H, m), 4.45-4.37 (1H, m), 6.71-6.65 (3H, m). A signal due to NH was not observed. MS (ESI) m/z 256 (M+H)+.

Step A5C: 2-Methyl-N-[1-(2-oxo-2,3-dihydro-1H-benzimidazol-5-yl)ethyl]propane-2-sulfinamide A mixture of N-[1-(3,4-diaminophenyl)ethyl]-2-methylpropane-2-sulfinamide and CDI (569 mg, 3.51 mmol) in THF-DCM (10 ml-10 ml) was refluxed for 6 hours. After cooling to the room tempertue, water (10 mL) was added to the mixture. The mixture was extracted with EtOAc (150 ml) and organic layer was washed with brine (30 ml), dried over sodium sulfate and concentrated. The residue was recrystallized from EtOAc to afford 430 mg (65%) of the title compound as a pale brown solid. $^1$H NMR (300 MHz, DMSO-d$_6$) δ ppm 1.11 (9H, s), 1.38 (3H, d, J=7.3 Hz), 4.37-4.28 (1H, m), 5.53 (1H, d, J=6.6 Hz), 6.84 (1H, d, J=7.3 Hz), 6.93 (1H, d, J=8.1 Hz), 6.99 (1H, s), 10.54 (1H, br.s), 10.60 (1H, br.s). MS (ESI) m/z 282 (M+H)+, 280 (M−H)−.

Step A5D: 5-(1-Aminoethyl)-1,3-dihydro-2H-benzimidazol-2-one hydrochloride

A mixture of 2-methyl-N-[1-(2-oxo-2,3-dihydro-1H-benzimidazol-5-yl)ethyl]propane-2-sulfinamide (430 mg, 1.53 mmol) and 10% hydrochloride in MeOH (10 ml) was stirred at room temperature for 4 hours. The mixture was concentrated, triturated with MeOH to give 265 mg (81%) of the title compound as a pale brown solid. $^1$H NMR (300 MHz, DMSO-$d_6$) δ ppm 1.50 (3H, d, J=6.6 Hz), 4.40-4.31 (1H, m), 6.94 (1H, d, J=7.3 Hz), 7.06 (1H, d, J=8.1 Hz), 7.10 (1H, s), 8.38 (2H, br.s), 10.74 (1H, br.s), 10.83 (1H, bs). MS (ESI) m/z 178 (M+H)$^+$, 176 (M−H)$^−$.

Amine 6: 1-quinolin-4-ylmethanamine

1-Quinolin-4-ylmethanamine can be prepared by the method described in Yakugaku Zasshi (1952), 72, P167-172.

Amine 7: 1-quinolin-4-ylethanamine, dihydrochloride

1-Quinolin-3-ylmethanamine can be prepared by the method described in Journal of the Chemical Society, Perkin Transactions 2, (1999), (11), 2415-2418.

Racemic 1-quinolin-4-ylethanamine (amine 7) was separated each single enantiomer by HPLC using chiral column (DAICEL CHIRALPAK AD-H, 250 mm×20.0 mm). Amine-7A showed former peak (retention time 10.7 min) as R-form. Amine-7B showed later peak (retention time 16.2 min) as S-form Amine 8: 1-isoquinolin-5-ylmethanamine 1-Isoquinolin-5-ylmethanamine was synthesized using the process disclosed in WO 2001070229 as an HCl salt.

Amine 9: 1-(1H-1,2,3-benzotriazol-5-yl)methanamine, mono hydrochloride 1-(1H-1,2,3-Benzotriazol-5-yl)methanamine was synthesized using the process disclosed in WO 2000026211 as an HCl salt.

Amine 10: 1-(2-methylquinolin-4-yl)methanamine 1-(2-methylquinolin-4-yl)methanamine was synthesized according to process described in Khimiko-Farmatsevticheskii Zhurnal (1981), 15(5), 70-5.

Amine 11: 1-(6-fluoroquinolin-4-yl)methanamine dihydrochloride

Step A11A: 6-fluoroquinoline-4-carbonitrile

A mixture of 4-chloro-6-fluoroquinoline (APOLLO) (1120 mg, 6.17 mmol), zinc cyanide (1450 mg, 12.3 mmol) and palladium (0) tetrakis(triphenylphosphine)(713 mg, 0.617 mmol) in dry DMF (15 ml) was treated with microwave (160° C., 30 min.). The mixture was diluted with ethyl acetate and filtered through a pad of celite. To the filtrate was added toluene (ca.20 ml) and the organic layer was washed with water (×2), brine, dried and concentrated in vacuo to give crude product. The crude product was purified by column chromatography on silica gel (ca. 250 g) with hexane-ethyl acetate (3:1) to give the title compound (880 mg, white solid). $^1$H NMR (270 MHz, CDCl$_3$) δ ppm 7.60-7.70 (1H, m), 7.75-7.79 (1H, m), 7.81-7.87 (1H, m), 8.20-8.28 (1H, m), 9.00-9.05 (1H, m).

Step A11B: 1-(6-fluoroquinolin-4-yl)methanamine dihydrochloride

A solution of 6-fluoroquinoline-4-carbonitrile (880 mg, 5.11 mmol) in 10% hydrochloric methanol (10 ml) and methanol (30 ml) was hydrogenated over 20% palladium hydroxide (150 mg) under balloon pressure (room temperature) for 6 hours. The mixture was diluted with methanol and the catalyst was filtered through a pad of celite pad (the filter cake was washed with methanol). The filtrate and washings were evaporated in vacuo to give crude product as white solid, which was recrystallized from methanol-diisopropyl ether to give the title compound (376 mg, slightly yellow solid). $^1$H NMR (270 MHz, DMSO-$d_6$) δ ppm 4.62-4.73 (2H, m), 7.86-7.967 (2H, m), 8.14-8.22 (1H, m), 8.30-8.39 (1H, m), 9.02 (2H, br.s), 9.12-9.17 (1H, m). MS (ESI) m/z 177 (M+H)$^+$ Amine 12: 1-(6,8-difluoroquinolin-4-yl)methanamine dihydrochloride Step A12A: 6,8-difluoroquinoline-4-carbonitrile A mixture of 4-chloro-6,8-difluoroquinoline (APOLLO) (1000 mg, 5.01 mmol), zinc cyanide (1180 mg, 10.0 mmol) and palladium (0) tetrakis(triphenylphosphine)(579 mg, 0.501 mmol) in dry DMF (15 ml) was treated at room temperature with stirring for 12 hours. Then, the reaction was quenched with saturated aqueous sodium bicarbonate solution and ethyl acetate. The organic layer was separated and the crude product was purified by column chromatography on silica gel (ca. 250 g) with hexane-ethyl acetate (3:1) to give the title compound (787 mg, yellow solid). $^1$H NMR (270 MHz, CDCl$_3$) 5 ppm 7.37-7.50 (1H, m), 7.65-7.75 (1H, m), 7.83-7.90 (1H, m), 9.05-9.10 (1H, m).

Step A12B: 1-(6,8-difluoroquinolin-4-yl)methanamine dihydrochloride

A solution of 6,8-difluoroquinoline-4-carbonitrile (787 mg, 4.14 mmol) in 10% hydrochloric methanol (10 ml) and methanol (30 ml) was treated in the same procedure described in Step A11B. The filtrate and washings were evaporated in vacuo to give crude product as white solid, which was recrystallized from methanol-diisopropyl ether to give the title compound (1030 mg, yellow solid). $^1$H NMR (270 MHz, CDCl$_3$) δ ppm 4.51-4.62 (m, 2H), 7.78-7.97 (3H, m), 8.85-9.05 (3H, m). MS (ESI) m/z 195 (M+H)$^+$.

Amine 13: 1-(1H-indazole-5-yl)ethanamine

Step A13A: 1-(1H-indazole-5-yl)-ethanone

To a solution of 5-iodo-1H-indazole (1.00 g, 4.10 mmol) in CH$_3$CN (20 ml) were added Boc$_2$O (984 mg, 4.51 mmol), DMAP (125 mg, 1.02 mmol) and Et$_3$N (0.64 ml, 4.6 mmol). The reaction mixture was stirred at room temperature for 5 hours, diluted with H$_2$O and extracted with AcOEt. The organic layers were dried over Na$_2$SO$_4$ and concentrated in vacuo to give the title compound. This compound (>1.5 g) was used in the next step without further purification. $^1$H NMR (300 MHz, CDCl$_3$) δ 1.72 (9H, s), 7.79 (1H, d, J=8.8 Hz), 7.98 (1H, d, J=8.8 Hz), 8.10 (2H, s). MS (ESI) m/z 345 (M+H)$^+$.

Then, to a cooled (0° C.), stirred solution of the compound (>1.5 g) in 1,4-dioxane (30 mL) were added n-butyl vinyl ether (2.7 ml, 20.9 mmol), t-butyl phosphine (0.30 ml, 1.2 mmol) and N-methyldicyclohexylamine (1.0 ml, 4.7 mmol). The mixture was degassed, purged with Ar and added Pd$_2$(dba)$_3$ (231 mg, 0.253 mmol). The reaction mixture was heated at 40° C. for 17.5 hours, cooled to room temperature and then diluted with AcOEt. This was washed with H$_2$O, saturated aqueous NH$_4$Cl and brine. The combined organic layer was dried over Na$_2$SO$_4$ and concentrated in vacuo. The residue was dissolved in THF-H$_2$O (2:1, 54 ml) and treated with HCl (6.0 ml) for 17 hours. Then the mixture was added HCl (6.0 mL). After stirring for 8 hours, the mixture was concentrated in vacuo. The residue was diluted with AcOEt, washed with H$_2$O and washed with saturated aqueous Na$_2$CO$_3$. The organic layer was dried over Na$_2$SO$_4$ and concentrated in vacuo. The crude product obtained was purified by column chromatography on silica gel (Yamazen, AcOEt:hexane=1:2) to give the title compound (344 mg, 52% from 5-iodo-1H-indazole) as a pale yellow solid. $^1$H NMR (300 MHz, DMSO-d$_6$) δ ppm 2.63 (3H, s), 7.61 (1H, d, J=8.8 Hz), 7.93 (1H, d, J=8.8 Hz), 8.27 (1H, s), 8.54 (1H, s), 13.40 (1H, s). MS (ESI) m/z 161 (M+H)$^+$, 159 (M−H)$^−$.

Step A13B: 1-(1H-indazole-5-yl)-ethanone oxime

To a suspension of 1-(1H-indazole-5-yl)-ethanone (334 mg, 2.09 mmol) in EtOH-H$_2$O (4:1, 10 ml) were added hydroxylamine hydrochloride (444 mg, 6.39 mmol) and sodium acetate (449 mg, 5.47 mmol). The reaction mixture was stirred at 80° C. for 15 hours and concentrated in vacuo. The residue was stirred with H$_2$O at room temperature for 10 min. The solid obtained was collected by filtration, and rinsed with H$_2$O. After drying, the title compound (260 mg, 71%) was obtained as a white solid. $^1$H NMR (270 MHz, DMSO-d$_6$) δ ppm 2.22 (3H, s), 7.52 (1H, d, J=8.6 Hz), 7.79 (1H, d, J=8.6 Hz), 7.98 (1H, s), 8.10 (1H, s), 11.05 (1H, s), 13.13 (br.s, 1H). MS (ESI) m/z 176 (M+H)$^+$, 174 (M−H)$^−$.

Step A13C: 1-(1H-indazole-5-yl)ethanamine

To a solution of corresponding oxime (122 mg, 0.694 mmol) in 1,2-dimethoxyethane (4.0 ml) was added dropwise to a stirred mixture of NaBH$_4$ (112 mg, 2.97 mmol) and TiCl$_4$ (0.28 mL, 1.5 mmol) in 1,2-dimethoxyethane (6.0 ml) at 0° C. The reaction mixture was stirred at room temperature for 2.5 hours and quenched with H$_2$O at 0° C. The mixture was basified with 2 M aqueous NaOH, and the aqueous layer was extracted with CH$_2$Cl$_2$. The combined organic layers were dried over Na$_2$SO$_4$ and concentrated in vacuo to give the title compound (120 mg, quant.). $^1$H NMR (300 MHz, DMSO-d$_6$) δ ppm 1.28 (3H, d, J=6.6 Hz), 4.09 (1H, q, J=6.6 Hz), 7.38 (1H, dd, J=1.5, 8.1 Hz), 7.45 (1H, d, J=8.1 Hz), 7.68 (1H, s), 7.98 (1H, s), 12.90 (1H, br.s).

Amine 14: 1-(6-methylquinolin-4-yl)methanamine dihydrochloride

A suspension of 6-methylquinoline-4-carbonitrile (158 mg, 0.94 mmol, Khimiko-Farmatsevticheskii Zhurnal, 1981, 15(5), 70) and 10% hydroxypalladium on carbon (20 mg) in 2% HCl-methanol (10 ml) was stirred at room temperature under hydrogen (1 atm) for 4 hours. The catalyst was removed by celite and washed with methanol and the filtrate was concentrated to furnish the title compound (213 mg, 93% yield) as a white solid. $^1$H NMR (270 MHz, DMSO-d$_5$) δ ppm 2.62 (3H, s), 4.76-4.79 (2H, m), 7.92-7.98 (2H, m), 8.22-8.29 (2H, m), 9.05 (2H, br.s), 9.21 (1H, d, J=5.3 Hz). MS (ESI): m/z 173 (M+H)$^+$.

Amine 15: 1-(8-methylquinolin-4-yl)methanamine dihydrochloride

This compound was synthesized from nitrile which is known compound according to the method of Amine 14. 1H NMR (300 MHz, DMSO-d$_6$) δppm 2.80 (3H, s), 4.66-4.75 (2H, m), 7.65-7.84 (3H, m), 8.12 (1H, d, J=8.8 Hz), 8.96 (2H, brs), 9.11 (1H, d, J=4.4 Hz). MS (ESI): m/z 173 (M+H)$^+$.

Amine 16: 1-quinolin-4-ylropan-1-amine

A Stirred mixture of 1-quinolin-4-ylmethanamine (166 mg, 1.05 mmol, CHEMBRIDGE) and benzophenone imine (190 mg, 1.05 mmol) was heated at 50° C. for 2 hours. The resultant product was dissolved in anhydrous THF (4 ml), cooled to −78° C. under nitrogen and tert-butyllithium (0.846 ml, 1.49M in hexane) was added via a syringe. The reaction mixture was allowed to stir for 15 minutes at −78° C. and 1-iodoethane (218 mg, 1.40 mmol) was added. After stirring the resultant solution at −78° C. for 30 minutes and at 0° C. for 2 hours, the reaction was quenched with methanol. Solvent was removed in vacuo, and the residue was dissolved in methanol (4 ml). Methoxylamine hydrochloride (150 mg, 1.80 mmol) was added and the solution was stirred at room temperature for 2 hours. The solvent was removed in vacuo and the residue was partitioned between ethyl acetate and 2N-HClaq. The aqueous solution was separated, basified to pH 11 with 2N-NaOHaq, and extracted with ethyl acetate. The combined organic layer was dried over Na$_2$SO$_4$, and concentrated to give the title compound (139 mg, brown oil). MS (ESI) m/z 187, (M+H)$^+$.

Amine 17: 2-amino-2-quinolin-4-ylethanol

Step 17A: 2-[(diphenylmethylene)amino]-2-quinolin-4-ylethyl Pivalate

A Stirred mixture of 1-quinolin-4-ylmethanamine (142 mg, 0.90 mmol, CHEMBRIDGE) and benzophenone imine (163 mg, 0.90 mmol) was heated at 50° C. for 2 hours. The resultant product was dissolved in dichloromethane (4 ml) and added to a solution of chloromethyl pivalate (136 mg, 0.90 mmol) and tetrabutylammonium bromide (150 mg, 0.465 mmol). 50% NaOHaq (0.9 ml) was added to the reaction mixture at 0° C. After the mixture was stirred at 0° C. for 1 hour, the reaction was diluted with dichloromethane (30 ml) and water (30 ml). The organic layer was separated, dried over Na$_2$SO$_4$, concentrated in vacuo and purified through silica gel column chromatography eluting with Hexane/EtOAc (3:1 to 2:1) to furnish the title compound (142 mg, 36% yield) as colorless oil. MS (ESI) m/z 437 (M+H)$^+$.

Step 17B: 2-amino-2-quinolin-4-ylethyl pivalate hydrochloride

A solution of 2-[(diphenylmethylene)amino]-3-2-quinolin-4-ylethyl pivalate (140 mg, 0.32 mmol) in methanol was added methoxylamine hydrochloride (27 mg, 0.32 mmol) and the mixture was stirred at room temperature for 3 hours. The solvent was removed in vacuo to furnish the mixture of the title compound and diphenylmethanone O-methyloxime. MS (ESI) m/z 273 (M+H)$^+$.

Carboxylic Acids

Carboxylic acids used in the following Examples were prepared by the methods below.

Carboxylic acid 1: 6-tert-butyl-2-naphthoic acid

Step CA1A: Methyl 6-tert-butyl-2-naphthoate

A mixture of 2-bromo-6-tert-butylnaphthalene (980 mg, 3.72 mmol), palladium acetate (84 mg, 0.37 mmol), 1,3-bis(diphenylphosphino)propane (153 mg, 0.37 mmol) and triethylamine (1.56 ml, 11.2 mmol) in MeOH (6 ml) and DMF (10 ml) was heated at 80° C. under carbon monooxide gas pressure using with balloon for 15 hours. After cooling to ambient temperature, the mixture was diluted with EtOAc-toluene (8:1)(160 ml) and filtered through a pad of celite. The filtrate and washings were washed with water, brine, dried over sodium sulfate and evaporated in vacuo to give the crude product which was purified through silica gel column chromatography eluting with hexane/EtOAc (10:1) to furnish the title compound as colorless oil (843 mg, 94%). $^1$H NMR (CDCl$_3$): 3 ppm 1.43 (9H, s), 3.97 (3H, s), 7.61-7.67 (1H, m), 7.79-7.93 (3H, m), 8.01-8.07 (1H, m), 8.57 (1H, br.s).

Step CA1B: 6-tert-Butyl-2-naphthoic acid

A mixture of methyl 6-tert-butyl-2-naphthoate (843 mg, 3.48 mmol) and 2M sodium hydroxide solution (6.96 mmol, 3.48 mmol) in MeOH (30 ml) was heated at 60° C. for 3 hours. After cooling to ambient temperature, the solvent was evaporated in vacuo and the residue was acidified to pH 2 with 2M hydrochloric aqueous solution. The aqueous layer was extracted with EtOAc and the combined solution was washed with brine, dried over sodium sulfate and evaporated in vacuo to give the crude product which was recrystallized from EtOAc and hexane to furnish the title compound as a white solid (614 mg, 77%). $^1$H NMR (DMSO-d$_6$): δ ppm 1.39 (9H, s), 7.70-7.76 (1H, m), 7.90-8.08 (4H, m), 8.55 (1H, br.s), 13.00 (1H, br.s).

Carboxylic acid 2: 6-tert-butylquinoline-2-carboxylic acid

Step CA2A: 6-tert-Butylquinoline 1-oxide

A mixture of 6-tert-butylquinoline (400 mg, 2.16 mmol, Journal of the Indian Chemical Society, 1998, 823) and mCPBA (639 mg, 2.59 mmol) in chloroform (10 ml) was stirred for 2 hours at room temperature. The mixture was concentrated and the crude residue was applied to a silica gel (NH silica) column chromatography and eluted with DCM/MeOH (20:1) to furnish the title compound (433 mg, quant.) as pale orange oil. $^1$H NMR (300 MHz, CDCl$_3$) δ ppm 1.43 (9H, s) 7.26-7.30 (1H, m), 7.73 (1H, d, J=8.1 Hz), 7.78 (1H, s), 7.85 (1H, dd, J=1.5, 8.8 Hz), 8.49 (1H, d, J=5.9 Hz), 8.67 (1H, d, J=8.8 Hz) MS (ES): m/z 202 (M+H)$^+$.

Step CA2B: 6-tert-Butylquinoline-2-carbonitrile

A mixture of 6-tert-butylquinoline 1-oxide (310 mg, 1.54 mmol), trimethylsilylcyanide (458 mg, 4.62 mmol), triethylamine (312 mg, 3.08 mmol) in acetonitrile (3 ml) was stirred for 15 minutes at 120° C. under microwave irradiation. The mixture was applied to a silica gel column chromatography and eluted with hexane/EtOAc (20:1) to furnish the title compound (295 mg, 91% yield) as a white solid. $^1$H NMR (300 MHz, CDCl$_3$) δ ppm 1.44 (9H, s), 7.68 (1H, d, J=8.8 Hz), 7.79 (1H, d, J=2.2 Hz), 7.94 (1H, d, J=2.2, 8.8 Hz), 8.11 (1H, d, J=8.8 Hz), 8.26 (1H, d, J=8.8 Hz) MS (ESI): m/z 211 (M+H)$^+$.

Step CA2C: 6-tert-Butylquinoline-2-carboxylic acid

A solution of 6-tert-butylquinoline-2-carbonitrile (295 mg, 1.40 mmol) and 2M-aqueous sodium hydroxide (3 ml) in EtOH (4.5 ml) was stirred for 4 hours at reflux. The mixture was diluted with water (10 ml), neutralized by 2M-aqueous hydrochloride and extracted with EtOAc (30 ml). The organic layer was dried over sodium sulfate, filtrated, and concentrated in vacuo to furnish the title compound (313 mg, quant.) as a white solid. $^1$H NMR (300 MHz, DMSO-d6) δ ppm 1.40 (9H, s), 7.93-7.97 (2H, m), 8.01-8.11 (2H, m), 8.41 (1H, d, J=8.1 Hz) MS (ESI): m/z 230 (M+H)$^+$.

Carboxylic acid 3: 2-tert-butylquinoline-6-carboxylic acid

Step CA3A: Methyl 2-tert-butylquinoline-6-carboxylate

To a THF (20 ml) solution of methyl quinoline-6-carboxylate (984 mg, 5.26 mmol, J. O. C., 2002, 67, 7890) was added t-butylmagnesium chloride in THF (15.8 ml, 1M solution) dropwise at −78° C. over 30 min. The mixture was stirred at −78° C. for 30 minutes and at −40° C. for 30 minutes, then at room temperature for 1 hour. The reaction was quenched with saturated ammonium chloride aqueous solution (100 ml) and extracted with EtOAc (100 ml×2) which was dried over sodium sulfate. Then, filtration, evaporation gave yellow oil, which was solved in THF (50 ml) and manganese dioxide (1.83 g 15.8 mmol) was added there. After the mixture was stirred at room temperature for 2.5 hours, the precipitate was removed through a pad of Celite and washed with EtOAc. The filtrate was concentrated and purified through silica gel column chromatography eluting with Hexane/EtOAc (20:1) to furnish the title compound (348 mg, 27% yield) as a white solid. $^1$H NMR (300 MHz, CDCl$_3$) δ ppm 1.48 (9H, s), 3.99 (3H, s), 7.59 (1H, d, J=8.8 Hz), 8.08 (1H, d, J=8.8 Hz), 8.17 (1H, d, J=8.8 Hz), 8.26 (1H, dd, J=2.2, 8.8 Hz), 8.55 (1H, d, J=2.2 Hz) MS (ESI): m/z 244 (M+H)$^+$.

Step CA3B: 2-tert-Butylquinoline-6-carboxylic acid

To a solution of methyl 2-tert-butylquinoline-6-carboxylate (347 mg, 1.43 mmol) in MeOH (4 ml) and THF (4 ml) was added 2M aqueous sodium hydroxide (2 ml) at room temperature. The mixture was stirred at room temperature for 1.5 hours. Then evaporated, diluted with water (5 ml), neutralized to pH 5~6 by 2M aqueous hydrochloride. The formed precipitate was collected, washed with water to furnish the title compound (282 mg, 86% yield) as a white solid. $^1$H NMR (300 MHz, CDCl$_3$) δ ppm 1.49 (9H, s), 7.62 (1H, d, J=8.8 Hz), 8.13 (1H, d, J=8.8 Hz), 8.20 (1H, d, J=8.8 Hz), 8.31-8.34 (1H, m), 8.64-8.66 (1H, m) MS (ESI): m/z 230 (M+H)$^+$.

Carboxylic acid 4: 6-(1,1,1,-trifluoro-2-hydroxypropan-2-yl)-2-naphthoic acid

Step CA4A: 2-(6-bromo-2-naphthyl)-1,1,1-trifluoropropan-2-ol

To a DMF (25 ml) solution of 1-(6-bromo-2-naphthyl)ethanone (1230 mg, 4.94 mmol), trimethylsilyl trifluoromethane (1050 mg, 7.41 mmol) and lithium acetate (16.3 mg, 0.247 mmol) were added and the mixture was stirred for 12 hours at room temperature. Then, the reaction was quenched with ethyl acetate and water, then the organic layer was separated and dried over sodium sulfate. The solvent was evaporated to give the residue which was treated with methanol-hydrogen chloride to give the product (1.25 g, 63%) as colorless oil. $^1$H NMR (300 MHz, CDCl$_3$) δ ppm 1.88 (3H, s), 7.57-7.60 (1H, m), 7.68-7.81 (3H, m), 8.02-8.05 (2H, m).

Step CA4B: Methyl 6-(2,2,2-trifluoro-1-hydroxy-1-methylethyl-2-naphthoate

To a DMF (25 ml) and methanol (10 ml) solution of methyl 6-acetyl-2-naphthoate (3.2 mmol, 1.25 g), palladium acetate (0.31 mmol, 70.4 mg), diphenylohosohino propane (129 mg, 0.31 mmol) and triethylamine (9.4 mmol, 951 mg) were added and the reaction mixture was stirred for 5 hours at room temperature. After the reaction was quenched with ethyl acetate and water, the organic layer was separated and dried over sodium sulfate. Then filtration and purification through silica gel column chromatography eluting with hexane:ethyl acetate (4:1) to give the title compound as a white solid (78%, 1.0 g). $^1$H NMR (300 MHz, CDCl$_3$) δ ppm 1.81 (3H, s), 3.93 (3H, s), 6.85 (1H, s), 7.83 (1H, d, J=9.2 Hz), 8.00-8.19 (3H, m), 8.26 (1H, s), 8.66 (1H, s). MS (ESI): m/z 299 (M+H)$^+$.

Step CA4C: 6-(1,1,1-trifluoro-2-hydroxypropan-2-yl)-2-naphthoic acid

To a methanol (15 ml) and 2N sodium hydroxide aqueous solution (5 ml), methyl 6-(2,2,2-trifluoro-1-hydroxy-1-methylethyl)-2-naphthoate (3.45 mmol, 1.0 g) was added and the mixture was stirred for 2 hours at 60° C. Then, the reaction mixture was acidified with 2M hydrogen chloride aqueous solution and partitioned with ethyl acetate (50 ml). The organic layer was dried over sodium sulfate and evaporated to give the title compound as a white solid (0.9 g, quant). $^1$H NMR (300 MHz, CDCl$_3$) δ ppm 1.81 (3H, s), 6.85 (1H, s), 7.70-8.75 (6H, m), 12.94 (1H, br.s).

Carboxylic acid 5:
2-(1-Methylcyclopropyl)quinoline-6-carboxylic acid

Step CA5A: 6-Bromo-2-isopropenylquinoline

To a stirred suspension of (methyl)triphenylphosphonium bromide (2000 mg, 5.60 mmol) in dry THF (15 ml) was added a solution of potassium t-butoxide (628 mg, 5.60 mmol) in dry THF (10 ml) at ice-cooling. After 2 hours at room temperature, to this was added a solution of 1-(6-bromoquinolin-2-yl)ethanone (700 mg, 2.80 mmol) in dry THF (15 ml) at ice-cooling. After 3 hours at ambient temperature, the mixture was quenched with water and extracted with ethyl acetate (×2). The combined solution was washed with brine, dried over sodium sulfate and concentrated in vacuo to give crude product, which was purified by column chromatography on silica gel (250 g) with hexane-ethyl acetate (10:1) to furnish the title compound (661 mg, 95%) as a tan solid. $^1$H NMR (270 MHz, CDCl$_3$) δ ppm 2.34 (3H, s), 5.50 (1H, s), 5.93 (1H, s), 7.65-7.78 (2H, m), 7.88-8.03 (3H, m). MS (ESI): m/z 248.11, 250.14 (M+H)$^+$.

Step CA5B)
Methyl-2-isopropenylquinoline-6-carboxylate

A mixture of 6-bromo-2-isopropenylquinoline (200 mg, 1.45 mmol), palladium acetate (18.1 mg, 0.081 mmol), 1,3-bis(diphenylphosphino)propane (33 mg, 0.081 mmol), triethylamine (245 mg, 2.42 mmol~0.337 ml) and methanol (1.03 g, 1.31 ml~32.2 mmol) in dry DMF (2.5 ml) was heated at 80° C. under carbon monooxide gas (balloon) for overnight (15 hours). The mixture was diluted with ethyl acetate-toluene (8:1) (159 ml) and the precipitate was filtered through a pad of celite. The organic layer was washed with water (×2), brine, dried over sodium sulfate and concentrated in vacuo to give the crude product. The crude product was purified by column chromatography on silica gel (150 g) with hexane-ethyl acetate (15:1) to furnish the title compound (150 mg, 82%) as dark yellow solid. $^1$H NMR (270 MHz, CDCl$_3$) δ ppm 2.36 (3H, s), 3.99 (3H, s), 5.53-5.57 (1H, m), 5.98 (1H, s), 7.73-7.78 (1H, m), 8.08-8.31 (3H, m), 8.54-8.56 (1H, m). MS (ESI): m/z 228.21 (M+H)$^+$.

Step CA5C) Methyl-2-(1-methylcyclopropyl)quinoline-6-carboxylate

To a stirred suspension of trimethylsulfoxonium iodide (435 mg, 2.06 mmol) in dimethylsulfoxide-THF (3 ml-2 ml) was added potassium t-butoxide (231 mg, 2.06 mmol) in one portion at ambient temperature. After 30 min. at same temperature, to this (colorless solution) was added a solution of methyl 2-isopropenylquinoline-6-carboxylate (312 mg, 1.37 mmol) in THF (3 ml) at room temperature. The mixture was stirred at room temperature for 40 min then 1 hour at 60° C. The mixture was quenched with water and diluted with ethyl acetate-toluene (8:1) (90 ml). The organic solution was separated and washed with water (×2), brine, dried over sodium sulfate and concentrated in vacuo to crude product. The crude product was purified by column chromatography on silica gel (250 g) with hexane-ethyl acetate (10:1) to furnish the title compound (225 mg, 68%) as a white solid. $^1$H NMR (270 MHz, CDCl$_3$) δ ppm 0.91-0.98 (2H, m), 1.38-1.45 (2H, m), 1.64 (3H, s), 3.98 (3H, s), 7.42-7.48 (1H, m), 7.97-8.27 (3H, m), 8.50-8.55 (1H, m). MS (ESI): m/z 242.15 (M+H)$^+$.

Step CA5D)
2-(1-Methylcyclopropyl)quinoline-6-carboxylic acid

A solution of methyl-2-(1-methylcyclopropyl)quinoline-6-carboxylate (225 mg, 0.93 mmol) and 2M sodium hydroxide solution (2 ml, 4 mmol) in methanol (10 ml) was heated at 60° C. for 2 hours. After the solvent was evaporated in vacuo, the residue was dissolved with water. The aqueous solution was neutralized with 2M hydrochloric acid solution (2 ml) and the precipitate white solid was extracted with ethyl acetate (×3). The combined solution was washed with brine, dried over sodium sulfate and concentrated in vacuo to give crude white solid, which was recrystallized from ethyl acetate and hexane to furnish the title compound (177 mg, 84%) as a white solid. MS (ESI): m/z 228.15 [M+H]$^+$, 226.13 [M−H]$^-$.

Carboxylic acid 6: 2,2-Trifluoro-1,1-dimethylethyl)quinoline-6-carboxylic acid

Step CA6A:
6-Bromo-quinolin-2-yl-1,1,1-trifluoropropan-2-ol

A DMF (5 ml) solution of the 6-bromoquinoline-ethanone (129 mg, 0.52 mmol), (trifluoromethyl)trimethylsilane (220 mg, 1.55 mmol) and tributylammonium fluoride (13.5 mg, 0.052 mmol) was stirred at 100° C. for 2 hours. Then the mixture was cooled to room temperature and added 1M-hydrochloride aqueous solution (2 ml). After 4 hours, the mixture was quenched with saturated sodium bicarbonate aqueous solution, and the product was extracted with ethyl acetate and dried over sodium sulfate. Then, filtration, evaporation, purification through silica gel column chromatography eluting with hexane/ethyl acetate (4:1) furnished the title compound (175 mg, quant.) as a white solid. $^1$H NMR (300 MHz, CDCl$_3$) δppm 1.81 (3H, s), 6.51 (1H, s), 7.64 (1H, d, J=8.1 Hz), 7.66-7.89 (1H, m), 8.00-8.12 (2H, m), 8.21 (1H, d, J=8.8 Hz). MS (ESI): m/z 320, 322 (M+H)$^+$.

Step CA6B:
6-bromoquinolin-2-yl-2,2,2-trifluoro-1-methylethyl methanesulfonate

To a solution of 6-Bromo-quinolin-2-yl-1,1,1-trifluoropropan-2-ol (5.06 g, 15.8 mmol) in THF (50 ml) was added sodium hydride (1.26 g, 31.6 mmol) portionwise at 0° C. and the mixture was stirred at room temperature for 2 hour. A solution of methanesulfonyl chloride (3.62 g, 31.6 mmol) in THF (10 ml) was added there at 0°. Then the reaction mixture was stirred at room temperature for 2 hours. The mixture was quenched with saturated sodium bicarbonate aqueous solution, and the product was extracted with ethyl acetate which was dried over sodium sulfate. Then, filtration, evaporation, purification through silica gel column chromatography eluting with hexane/ethyl acetate (15:1 to 5:1) furnished the title compound (6.29 g, 84% yield) as a white solid. $^1$H NMR (300 MHz, CDCl$_3$) δppm 2.45 (3H, s), 3.24 (3H, s), 7.81-7.86 (2H, m), 7.96-8.05 (2H, m), 8.17 (1H, d, J=8.8 Hz). MS (ESI): m/z 397, 399 (M+H)$^+$.

Step CA6C: 6-Bromo-2-(2,2,2-trifluoro-1,1-dimethylethyl)quinoline

A suspension of 6-bromoquinolin-2-yl-2,2,2-trifluoro-1-methylethyl methanesulfonate (11.97 g, 30 mmol) in cyclohexane (120 ml) was added trimethylaluminum (120 ml, 123 mmol, 1.03M in hexane solution) at room temperature, and the mixture was stirred at room temperature for 1 hour. The reaction was carefully quenched with saturated sodium bicarbonate aqueous solution (30 ml), brine (10 ml) and diluted with ethyl acetate and heptane (200 ml). After the mixture was stirred for 30 minutes, formed precipitate was removed by celite and washed with ethyl acetate. The filtrate was concentrated and purified through silica gel column chromatography eluting with hexane only to furnish the title compound (9.56 g, 80% yield) as colorless oil. $^1$H NMR (300 MHz, CDCl$_3$) δppm 1.72 (6H, s), 7.66 (1H, d, J=8.8 Hz), 7.75-7.80 (1H, m), 7.96-8.00 (2H, m), 8.06 (1H, d, J=8.8 Hz). MS (ESI): m/z 318, 320 (M+H)$^+$.

Step CA6D: Methyl 2-(2,2,2-trifluoro-1,1-dimethylethyl)quinoline-6-carboxylate

A mixture of the 6-bromo-2-(2,2,2-trifluoro-1,1-dimethylethyl)quinoline (950 mg, 3.0 mmol), triethylamine (1.25 ml, 9.0 mmol), 1,3-bis(diphenylphosphino)propane (123 mg, 0.3 mmol), palladium acetate (67 mg, 0.3 mmol) and methanol (4.8 ml) in DMF (10 ml) was stirred at reflux under carbon monoxide (1 atm) for 16 hours. Then the reaction was quenched with saturated sodium bicarbonate aqueous solution and the product was extracted with ethyl acetate and dried over sodium sulfate. Then, filtration, evaporation, purification through silica gel column chromatography eluting with hexane/ethyl acetate (25:1) furnished the title compound (777 mg, 88% yield) as a white solid. $^1$H NMR (300 MHz, CDCl$_3$) δppm 1.74 (6H, s), 4.00 (3H, s), 7.71 (1H, d, J=8.8 Hz), 8.14 (1H, d, J=8.8 Hz), 8.25 (1H, d, J=8.8 Hz), 8.28-8.32 (1H, m), 8.58-8.59 (1H, m). MS (ESI): m/z 298 (M+H)$^+$.

Step CA6E: 2,2-Trifluoro-1,1-dimethylethyl)quinoline-6-carboxylic acid

A methanol (6 ml) and THF (6 ml) solution of methyl 2-(2,2,2-trifluoro-1,1-dimethylethyl)quinoline-6-carboxylate (777 mg, 2.6 mmol) and 2M-sodium hydroxide aqueous solution (2.6 ml, 5.2 mmol) were treated according to the procedure described in carboxylic acid 1 to furnish the title compound (735 mg, 99% yield) as a white solid. $^1$H NMR (300 MHz, CDCl$_3$) δ ppm 1.75 (6H, s), 7.74 (1H, d, J=8.8 Hz), 8.19 (1H, d, J=8.8 Hz), 8.29 (1H, d, J=8.8 Hz), 8.35-8.40 (1H, m), 8.69-8.70 (1H, m). MS (ESI): m/z 284 (M+H)$^+$.

Carboxylic acid 7:
6-(1-methylcyclopropyl)-2-naphthoic acid

Step CA7A: Methyl 6-(prop-1-en-2-yl)-2-naphthoate

To a suspension of methyl triphenylphosphonium bromide (2.41 g, 6.74 mmol) in THF (20 ml) was added dropwise potassium tert-butoxide (756 mg, 6.74 mmol) in THF (20 ml) at 0° C., and the mixture was stirred at room temperature for 1.5 hours. Then, methyl 6-acetyl-2-naphthoate (*J. Org. Chem.*, 1990, 55, 319-324, 769 mg, 3.37 mmol) in THF (5 ml) was added at room temperature, and the resulting mixture was stirred at room temperature for 2 hours. The reaction was quenched with water (100 ml) and extracted with ethyl acetate-hexane (1:2). The organic layer was dried over sodium sulfate and concentrated in vacuo. The crude material was purified by silica gel column chromatography, eluting with ethyl acetate-hexane (0:100 to 1:20) to give 0.67 g (88% yield) of the title compound as white solid. $^1$H NMR (270 MHz, CDCl$_3$) δppm 2.28 (3H, s), 3.99 (3H, s), 5.26 (1H, s), 5.58 (1H, s), 7.74 (1H, d, J=8.6 Hz), 7.82-7.97 (3H, m), 8.05 (1H, d, J=8.6 Hz), 8.58 (1H, s). MS (ESI) m/z: not observed M+peak.

Step CA7B: Methyl 6-(1-methylcyclopropyl)-2-naphthoate

Diethylzinc (1.0 M in Hexane)(6.30 ml, 6.30 mmol) was added to a solution of methyl 6-(prop-1-en-2-yl)-2-naphthoate (0.57 g, 2.5 mmol) in dichloroethane at 0° C. Diiodomethane (1.01 ml, 12.6 mmol) was then added dropwise to the mixture solution and the resultant mixture was stirred at 60° C. for 20 h. The reaction mixture was cooled to room temperature, diluted with saturated aqueous ammonium chloride (30 mL), and the mixture was extracted with CH$_2$Cl$_2$ (30 ml×3). The combined organic layer was washed with saturated aqueous sodium bicarbonate (50 ml) and brine (50 ml), and the organic layer was dried over Na$_2$SO$_4$. Removal of the solvent gave a residue, which was chromatographed on a column of silica gel eluting with ethyl acetate-hexane (1:20) to give 0.91 g of the title compound as white solid. $^1$H NMR (270 MHz, CDCl$_3$) δppm 0.75-0.95 (2H, m), 0.95-1.13 (2H, m), 1.52 (3H, s), 3.97 (3H, s), 7.41 (1H, d, J=9.9 Hz), 7.74 (1H, s), 7.82 (1H, d, J=7.8 Hz), 7.86 (1H, d, J=8.6 Hz), 8.04 (1H, d, J=8.6 Hz), 8.56 (1H, s). MS (ESI) m/z: not observed M+ peak.

Step CA7C: 6-(1-Methylcyclopropyl)-2-naphthoic acid

A mixture of Methyl 6-(1-methylcyclopropyl)-2-naphthoate (crude 0.91 g, 2.5 mmol) and 2M sodium hydroxide solution (3.8 ml) in methanol (7.6 ml) was heated at 60° C. for 2 hours. After cooling to room temperature, the mixture was washed with diethyl ether (100 ml). The aqueous layer was acidified to pH<3 with 2M hydrochloric acid solution and the mixture was extracted with dichloromethane-methanol (10:1, 150 ml×3 times). The combined organic layers were dried over sodium sulfate and concentrated in vacuo to give 0.444 g (78% yield for 2 steps) of the title compound as white solid. $^1$H NMR (300 MHz, DMSO-$d_6$) δ ppm 0.77-0.92 (2H, m), 0.95-1.11 (2H, m), 1.49 (3H, s), 7.42 (1H, d, J=8.8 Hz), 7.84 (1H, s), 7.90-7.97 (2H, m), 8.01 (1H, d, J=8.8 Hz), 8.54 (1H, s). MS (ESI): m/z 225 (M−H)$^-$.

Carboxylic acid 8: 6-Cyclopropylnaphthalene-2-carboxylic acid

Step CA8A: 6-Cyclopropylnaphthalene-2-carboxylic acid methyl ester

A flask containing 6-bromo-naphthalene-2-carboxylic acid methyl ester (1.0 g, 3.7 mmol), cyclopropyl boronic acid (421 mg, 4.9 mmol), palladium acetate (42 mg, 0.02 mmol), tricyclohexylphosphine (106 mg, 0.04 mmol) and potassium phosphate (2.802 g, 13.2 mmol) in toluene (15 ml) and water (0.75 ml) was degassed with $N_2$ for 10 minutes. The reaction was heated at 100° C. for 1 hour. After cooling, the reaction mixture was poured into saturated NaHCO$_3$ solution (100 ml) and extracted with EtOAc (3×50 ml). The combined organics were washed with brine (3×50 ml), dried (MgSO$_4$), filtered and concentrated. Flash chromatography (0 to 10% EtOAc in hexane) gave the title compound (270 mg, 30%) as an off-white solid. $^1$H NMR (400 MHz, DMSO-$d_6$) δ ppm 0.83-0.87 (2H, m), 1.05-1.11 (2H, m), 2.09-2.16 (1H, m), 3.90 (3H, s), 7.33 (1H, dd, J=8.6 Hz, 1.8 Hz), 7.70 (1H, s), 7.89-7.95 (2H, m), 8.02 (1H, d, J=8.6 Hz), 8.56 (1H, s). LC/MS: m/z not observed; retention time=3.93 min Step CA8B: 6-Cyclolropylnaphthalene-2-carboxylic acid To a solution of 6-cyclopropylnaphthalene-2-carboxylic acid methyl ester (226 mg, 1 mmol) in tetrahydrofuran (9 ml) and ethanol (3 ml) was added a solution of lithium hydroxide (72 mg, 3 mmol) in, water (3 ml). The reaction was stirred at 50° C. for 2 hours, then poured into 2M HCl and extracted with EtOAc (3×50 ml). The combined organics were washed with brine (2×100 ml), dried (MgSO$_4$), filtered and concentrated. Trituration using DCM/hexanes gave the title compound (150 mg, 67%) as a white solid. $^1$H NMR (400 MHz, MeOH-$d_4$) δ ppm 0.85-0.89 (2H, m), 1.09-1.16 (2H, m), 2.11-2.16 (1H, m), 7.30 (1H, dd, J=8.6 Hz, 1.7 Hz), 7.64 (1H, s), 7.84 (1H, d, J=8.6 Hz), 7.89 (1H, d, J=8.6 Hz), 8.00 (1H, dd, J=8.6 Hz, 1.7 Hz), 8.55 (1H, s). LC/MS: m/z not observed; retention time=3.18 min Carboxylic acid 9: 7-tert-butylquinoline-3-carboxylic acid Step CA9A: Ethyl 7-tert-butyl-4-oxo-1,4-dihydro-quinoline-3-carboxylate A mixture of 3-tert-butylaniline (5.30 g, 35.5 mmol) and diethyl ethoxymethylenemalonate (10.2 g, 47.30 mmol) were heated at 60° C. for 15 min. then 1 hour at 120° C. After the generated ethanol was evaporated in vacuo, the crude oil was added dropwise to boiling diphenylether (150 ml) at 200~250° C. and the mixture was stirred at 250° C. for 90 min. After cooling to room temperature, the mixture was diluted with hexane (ca. 200 ml) and the precipitate solid was collected to give (4.55 g, 47%) of the title compound as a slightly yellow solid. The compound was used for the next step without the determination of NMR, MS for hard solids.

Step CA9B: Ethyl 7-tert-butyl-4-chloroquinoline-3-carboxylate

A mixture of Ethyl 7-tert-butyl-4-oxo-1,4-dihydroquinoline-3-carboxylate (4.54 g, 16.6 mmol) in POCl$_3$ (60 ml) was heated at 120° C. for 3 hours. After the solvent was evaporated in vacuo, the residue was diluted with CH$_2$Cl$_2$. The organic layer was poured into ammonia-water with ice-cooling. The aqueous layer was extracted with CH$_2$Cl$_2$ and the organic layer was washed with water, dried over sodium sulfate and concentrated in vacuo to give crude product. The crude product was purified by column chromatography on silica gel with hexane-ethyl acetate (8:1 to 6:1) to give the title compound (4.82 g) as colorless oil. $^1$H NMR (270 MHz, DMSO-$d_6$) δ ppm 1.35-1.44 (3H, m), 1.42 (9H, s), 4.38-4.49 (2H, m), 7.97-8.06 (2H, m), 8.30-8.36 (1H, m), 9.15 (1H, s).

Step CA9-C: Ethyl 7-tert-butylquinoline-3-carboxylate

A solution of ethyl 7-tert-butyl-4-chloroquinoline-3-carboxylate (2.06 g, 7.06 mmol) and triethylamine (1.97 ml, 21.2 mmol) in ethanol (70 ml) was hydrogenated over 5% palladium-carbon (300 mg) at balloon pressure for 1.5 hours. After the catalyst was filtered through a pad of celite, the filter cake was washed with CH$_2$Cl$_2$. The filtrate and washings were evaporated in vacuo to give crude product, which was purified by column chromatography on silica gel with hexane-ethyl acetate (8:1) to give the title compound (1.68 g, 92.5%) as yellow colored oil. $^1$H NMR (270 MHz, CDCl$_3$) δ ppm 1.43-1.51 (3H, m), 1.45 (9H, s), 4.48 (2H, q, J=7.0 Hz), 6.69-7.75 (1H, m), 7.85-7.91 (1H, m), 8.13 (1H, s), 6.79-8.82 (1H, m), 9.41-9.44 (1H, m).

Step CA9D: 7-Tert-Butylquinoline-3-carboxylic acid

A mixture of Ethyl 7-tert-butylquinoline-3-carboxylate (1.63 g, 6.33 mmol) in 2M sodium hydroxide aqueous solution (6.4 ml, 12.8 mmol) and ethanol (50 ml) was heated at 75° C. for 2 hours. After the solvent was evaporated in vacuo, the residue was diluted with water. The aqueous solution was acidified to pH3 with 2M hydrochloric acid aqueous solution with ice-cooling and extracted with ethyl acetate. The combined solution was washed with brine, dried over sodium sulfate and concentrated in vacuo to give crude product, which was recrystallized from ethyl acetate and hexane to give the title compound (1.27 g, 88%) as a white solid. MS (ESI) m/z 228 (M−H)$^-$, 230 (M+H)$^+$. LC-MS: 2.46 min (Neutral full range 4_96)

Carboxylic acid 10: 2-(2,2,2-trifluoro-1-hydroxy-1-methylethyl)quinoline-6-carboxylic acid Step CA10A) Methyl 2-(2,2,2-trifluoro-1-hydroxy-1-methylethyl)quinoline-6-carboxylate This compound was prepared from 6-Bromo-quinolin-2-yl-1,1,1-trifluoropropan-2-ol according to the same procedure described in Step CA6D. $^1$H NMR (300 MHz, CDCl$_3$) δ ppm 1.82 (3H, s), 4.02 (3H, s), 6.55 (1H, s), 7.69 (1H, d, J=8.1 Hz), 8.18 (1H, d, J=8.8 Hz), 8.37-8.41 (2H, m), 8.66-8.68 (1H, m). MS (ESI): m/z 300 (M+H)$^+$.

Step 10B) 2-(2,2,2-trifluoro-1-hydroxy-1-methylethyl)quinoline-6-carboxylic acid This compound was prepared from methyl 2-(2,2,2-trifluoro-1-hydroxy-1-methylethyl)quinoline-6-carboxylate according to the same procedure described in Step CA6E. $^1$H NMR (300 MHz, CDCl$_3$) δppm 1.84 (3H, s), 7.72 (1H, d, J=8.1 Hz), 8.23 (1H, d, J=8.8 Hz), 8.42-8.47 (2H, m), 8.77-8.78 (1H, m). MS (ESI): m/z 286 (M+H)$^+$.

Carboxylic acid 11: 6-(2,2,2-Trifluoro-1-methoxy-1-methylethyl)-2-naphthoic acid

Step CA11A) Methyl 6-(2,2,2-trifluoro-1-methoxy-1-methylethyl)-2-naphthoate

To a THF solution of the CA4A (0.45 g, 1.5 mmol), sodium hydride (80 mg, 2.2 mmol) was added and the mixture was stirred for 30 minutes at 0° C. Then, methyl iodide (642 mg, 4.5 mmo) was added to the mixture and additional stirring was allowed for 3 hours. Then, the product was extracted with ethyl acetate and dried over sodium sulfate. Then filtration, evaporation, purification through silica gel column chromatography eluting with hexane:ethyl acetate=4:1 to give the title compound as a white solid in 58% yield. $^1$H NMR (300 MHz, DMSO-d$_6$) δppm 1.91 (3H, s), 3.22 (3H, s), 3.94 (3H, s), 7.74 (1H, d, J=9.2 Hz), 8.04 (1H, d, J=8.6 Hz), 8.14-8.24 (3H, m), 8.68 (1H, s).

Step CA11B) 6-(2,2,2-Trifluoro-1-methoxy-1-methylethyl)-2-naphthoic acid

The title compound was prepared by the same procedure of Step CA4C using the compound of CA11A instead of the compound of CA4B to give the title compound in 98% yield as a white solid. $^1$H NMR (300 MHz, DMSO-d$_6$) δppm 1.91 (3H, s), 3.22 (3H, s), 7.71-7.74 (1H, m), 8.01-8.21 (4H, m), 8.64 (1H, s), 13.2 (1H, br.s).

Examples

Examples A1-A9

Example A1: To a DMF (7 ml) solution of Amine 1 (59 mg, 0.30 mmol), Carboxylic acid 1 (68 mg, 0.30 mmol), HBTU (146 mg, 0.39 mmol) and triethylamine (0.12 ml, 0.89 mmol) were added and the mixture was stirred for 3 hours at room temperature. The reaction was quenched with water and the product was extracted with EtOAc. Then, evaporation, purification through HPLC (the used column was MS C 30×50 mm, and the condition was acetonitrile/0.05% aqueous formic acid eluting with 32 to 68) gave the title compound (19 mg, 17%) as a white solid. The fraction time for the desired product was 3.70 min. The compounds of Examples A2 through A9 were prepared by a similar method to that of Example A1 using the following starting materials and the appropriate solvent as described in Scheme 1.

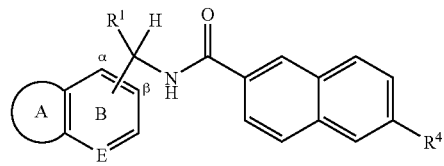

TABLE 3

| Ex. | Chemical Structure | Compound name/Physical data |
|---|---|---|
| A1 | 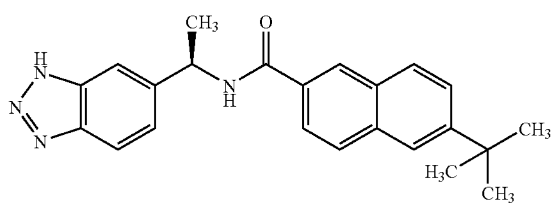 | N-[(1R)-1-(1H-1,2,3-benzotriazol-6-yl)ethyl]-6-tert-butyl-2-naphthamide: It was prepared using Amine 1 and Carboxylic acid 1. $^1$H NMR (300 MHz, DMSO-d$_6$) δ 1.38 (9H, s), 1.60 (3H, d, J = 7.3 Hz), 5.33-5.47 (1H, m), 7.55 (1H, d, J = 8.8 Hz), 7.71 (1H, dd, J = 8.4, 1.8 Mz), 7.84-8.01 (6H, m), 8.47 (1H, s), 9.08 (1H, d, J = 8.1 Mz), NH could not be observed. MS (ESI) m/z 371 (M − H)$^-$, 373 (M + H)$^+$ |
| A2 | 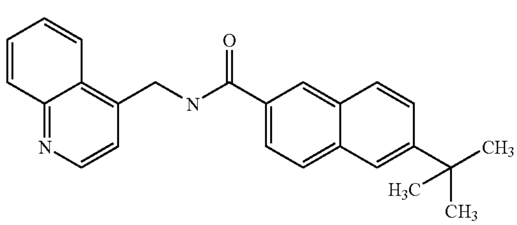 | 6-tert-butyl-N-(quinolin-4-ylmethyl-naphthamide: It was prepared using Amine 6 and Carboxylic acid 1. $^1$H NMR (300 MHz, DMSO-d$_6$) δ 1.39 (9H, s), 5.01-5.07 (2H, m), 7.47 (1H, d, J = 4.6 Hz), 7.65-8.09 (8H, m), 8.29 (1H, d, J = 7.9 Hz), 8.50 (1H, s), 8.66 (1H, d, J = 4.0 Hz), 9.30-9.36 (1H, m). MS (ESI): m/z 369 (M + H)$^+$. |
| A3 | 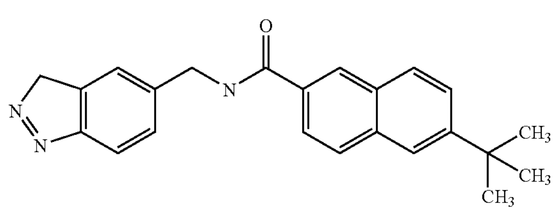 | 6-tert-butyl-N-(3H-indazol-5-ylmethyl)-2-naphthamide: It was prepared using Amine 3 and Carboxylic acid 1. $^1$H NMR (300 MHz, DMSO-d$_6$) δ 1.38 (9H, s), 4.62 (2H, d, J = 5.9 Hz), 7.35-7.42 (1H, m), 7.46-7.54 (1H, m), 7.67-7.74 (2H, m), 7.86-8.06 (5H, m), 8.46 (1H, s), 9.20 (1H, t, J = 5.9 Mz), 13.0 (1H, s). MS (ESI) m/z 358 (M + H)$^+$ |

TABLE 3-continued

| Ex. | Chemical Structure | Compound name/Physical data |
|---|---|---|
| A4 | 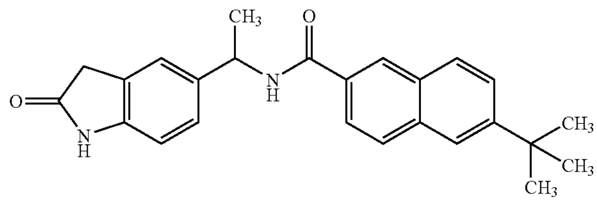 | 6-tert-butyl-N-[1-(2-oxo-2,3-dihydro-1H-indol-5-yl)ethyl]-2-naphthamide: It was prepared using Amine 4 and Carboxylic acid 1. $^1$H NMR (300 MHz, DMSO-$d_6$) δ 1.39 (9H, s), 1.49 (3H, d, J = 7.3 Hz), 3.46 (2H, s), 5.11-5.24 (1H, m), 6.77 (1H, d, J = 8.1 Mz), 7.19-7.38 (2H, m), 7.71 (1H, d, J = 6.6 Hz), 7.84-8.01 (4H, m), 8.43 (1H, s), 8.87 (1H, d, J = 8.1 Hz), 10.33 (1H, s). MS (ESI) m/z 387 (M − H)$^-$, 385 (M + H)$^+$ |
| A5 | 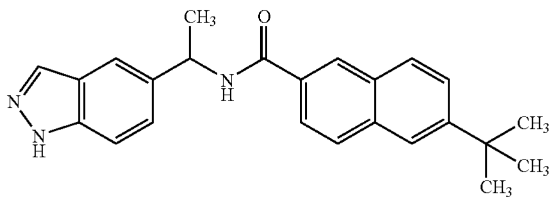 | 6-tert-butyl-N-[1-1H-indazole-5-ylethyl]-2-naphthamide: It was prepared using Amine 13 and Carboxylic acid 1. $^1$H NMR (300 MHz, DMSO-$d_6$) δ 1.39 (9H, s), 1.58 (3H, d, J = 6.6 Hz), 5.23-5.41 (1H, m), 6.51-6.57 (1H, m), 7.43-7.54 (2H, m), 7.66-7.79 (2H, m), 7.84-8.07 (3H, m), 7.95 (1H, s), 8.41-8.48 (1H, m), 8.92-9.01 (1H, m), 12.92-13.10 (1H, br.s). MS (ESI) m/z 370 (M − H)$^-$, 372 (M + H)$^+$ |
| A6 | 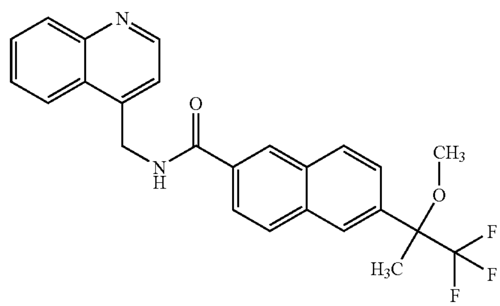 | N-(quinolin-4-ylmethyl)-6-(1,1,1-trifluoro-2-methoxypropan-2-yl)-2-naphthamide: It was prepared using Amine 6 and Carboxylic acid 11. $^1$H NMR (300 MHz, CDCl$_3$) δ 1.90 (3H, s), 3.29 (3H, s), 5.34 (2H, s), 7.72-8.02 (7H, m), 8.26-8.29 (2H, m), 8.35-8.47 (3H, m), 8.78 (1H, s). MS (ESI) m/z 437 (M − H)$^-$, 439 (M + H)$^+$ |
| A7 | 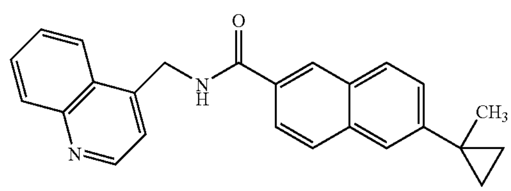 | 6-(1-methylcyclopropyl)-N-(quinolin-4-ylmethyl)-2-naphthamide: It was prepared using Amine 6 and Carboxylic acid 7. $^1$H NMR (270 MHz, DMSO-$d_6$) δ ppm 0.83-0.92 (2H, m), 0.97-1.05 (2H, m), 1.50 (3H, s), 5.05 (2H, d, J = 5.9 Hz), 7.42 (1H, dd, J = 2.0 Hz, 8.6 Hz), 7.48 (1H, d, J = 4.6 Hz), 7.68 (1H, t, J = 7.9 Hz), 7.75-7.88 (2H, m), 7.91-8.02 (3H, m), 8.08 (1H, d, J = 7.9 Hz), 8.30 (1H, d, J = 7.9 Hz), 8.50 (1H, s), 8.87 (1H, d, J = 4.0 Hz), 9.33 (1H, br t, J = 5.9 Hz). MS (ESI) m/z 365 (M − H)$^-$, 367 (M + H)$^+$. |
| A8 | 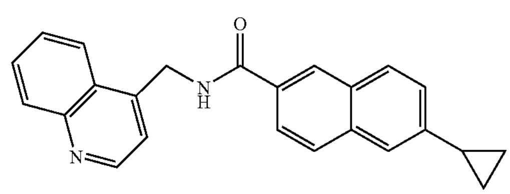 | 6-cyclopropyl-N-(quinolin-4-ylmethyl)-2-naphthamide It was prepared using Amine 6 and Carboxylic acid 8. $^1$H NMR (270 MHz, DMSO-$d_6$) δ ppm 0.78-0.91 (2H, m), 1.00-1.13 (2H, m), 2.05-2.20 (1H, m), 5.05 (2H, d, J = 5.3 Hz), 7.32 (1H, d, J = 7.9 Hz), 7.48 (1H, d, J = 4.0 Hz), 7.62-7.75 (2H, m), 7.80 (1H, t, J = 7.9 Hz), 7.87-8.02 (3H, m), 8.08 (1H, d, J = 7.9 Hz), 8.30 (1H, d, J = 8.6 Hz), 8.49 (1H, s), 8.87 (1H, d, J = 4.6 Hz), 9.32 (1H, br t, J = 5.3 Hz). MS (ESI) m/z 351 (M − H)$^-$, 353 (M + H)$^+$. |
| A9 | 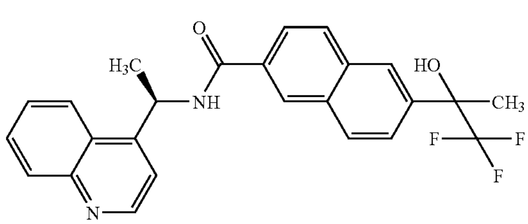 | N-[(1R)-1-quinolin-4-ylethyl]-6-(2,2,2-trifluoro-1-hydroxy-1-methylethyl)-2-naphthamide: It was prepared using Amine 7 and Carboxylic acid 4. $^1$H NMR (300 MHz, acetone-$d_6$) δ 1.74 (3H, d, J = 7.3 Hz), 1.87 (3H, s), 5.77 (1H, s), 6.08-6.20 (1H, m), 7.60-7.66 (2H, m), 7.69-7.78 (1H, m), 7.82 (1H, d, J = 8.1 Hz), 7.95-8.03 (3H, m), 8.05 (1H, d, J = 7.3 Hz), 8.24 (1H, s), 8.34 (1H, d, J = 8.1 Hz), 8.43-8.54 (2H, m), 8.84 (1H, d, J = 5.1 Hz). MS (ESI) m/z 437 (M − H)$^-$, (M + H)$^+$ |

Examples B1-B7

The compounds of Examples B1 through B7 were prepared by a similar method to that of Example A1 using the following starting materials and the appropriate solvent as described in Scheme 1.

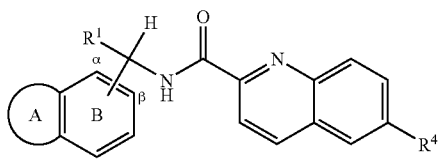

TABLE 4

| Ex. | Chemical Structure | Compound name/Physical data |
|---|---|---|
| B1 | 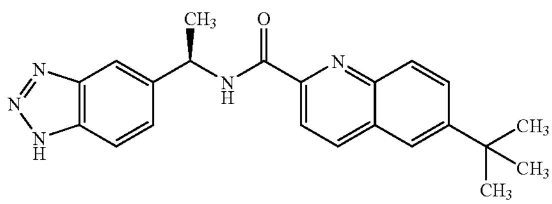 | N-[(1R)-1-(1H-1,2,3-benzotriazol-6-yl)ethyl]-6-tert-butylquinoline-2-carboxamide: It was prepared using Amine 1 and Carboxylic acid 2. $^1$H NMR (300 MHz, DMSO-$d_6$) δ 1.40 (9H, s), 1.66 (3H, d, J = 6.6 Hz), 5.33-5.48 (1H, m), 7.32-7.40 (1H, m), 7.58 (1H, d, J = 8.8 Mz), 7.83-8.18 (6H, m), 8.53 (1H, d, J = 8.8 Mz), 9.30 (1H, d, J = 8.1 Mz). MS (ESI) m/z 372 (M − H)$^-$, 374 (M + H)$^+$ |
| B2 | 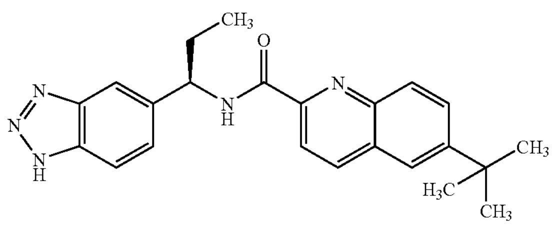 | N-[(1R)-1-(1H-1,2,3-benzotriazol-6-yl)propyl]-6-tert-butylquinoline-2-carboxamide: It was prepared using Amine 2 and Carboxylic acid 2. $^1$H NMR (300 MHz, DMSO-$d_6$) δ 0.86-0.97 (3H, m), 1.41 (9H, s), 1.93-2.21 (2H, m), 5.09-5.20 (1H, m), 7.37 (1H, s), 7.56 (1H, d, J = 8.8 Mz), 7.83-8.20 (6H, m), 8.52 (1H, d, J = 8.8 Mz), 9.24 (1H, d, J = 8.1 Mz). MS (ESI) m/z 386 (M − H)$^-$, 388 (M + H)$^+$ |
| B3 | 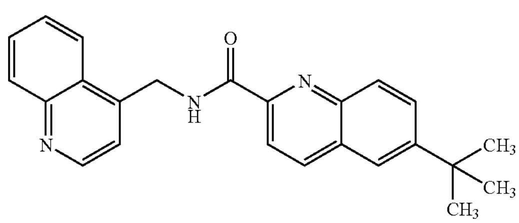 | 6-tert-butyl-N-(quinolin-4-ylmethyl)quinoline-2-carboxamide: It was prepared using Amine 6 and Carboxylic acid 2. $^1$H NMR (300 MHz, DMSO-$d_6$) δ 1.42 (9H, s), 5.09 (2H, d, J = 5.9 Hz), 7.45 (1H, d, J = 4.6 Hz), 7.69 (1H, t, J = 6.9 Hz), 7.80 (1H, t, J = 6.9 Hz), 8.19-8.00 (5H, m), 8.34 (1H, d, J = 8.6 Mz), 8.57 (1H, d, J = 8.6 Mz), 8.86 (1H, d, J = 4.6 Mz), 9.65 (1H, t, J = 6.3 Hz), MS (ESI) m/z 370 (M + H)$^+$. |
| B4 | 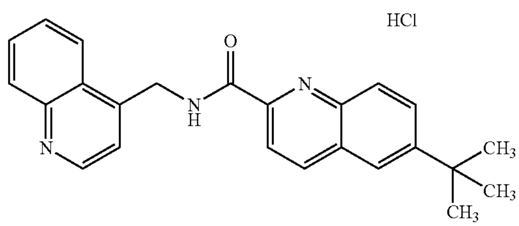 | 6-tert-butyl-N-(quinolin-4-ylmethyl)quinoline-2-carboxamide hydrochloride: The mixture of Example B3 (113 mg, 0.31 mmol) and 10% HCl—MeOH (5 ml) was stirred at room temperature for 2 hours. Then evaporated, crystallized from ethanol to furnish the title compound (103 mg, 91% yield) as a white solid. $^1$H-NMR (300 MHz, DMSO-$d_6$) δ 1.43 (9H, s), 5.27 (1H, d, J = 5.9 Hz), 7.86 (1H, d, J = 5.3 Hz), 8.18-7.95 (7H, m), 8.37 (1H, d, J = 8.6 Hz), 8.65-8.57 (2H, m), 9.16 (1H, d, J = 5.9 Hz), 9.85 (1H, t, J = 6.3 Hz). MS (ESI) m/z 370 (M + H)$^+$. |
| B5 | 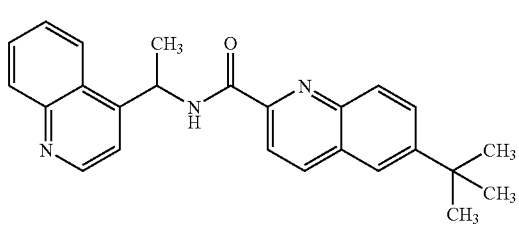 | 6-tert-butyl-N-(1-quinolin-4-ylethyl)quinoline-2-carboxamide hydrochloride: It was prepared using Amine 6 and Carboxylic acid 2. $^1$H-NMR (270 MHz, DMSO-$d_6$) δ 1.42 (9H, s), 1.78 (3H, d, J = 7.3 Hz), 6.22-6.12 (1H, m), 8.07-7.99 (4H, m), 8.21-8.14 (3H, m), 8.39 (1H, d, J = 8.6 Hz), 8.54 (1H, d, J = 8.6 Hz), 8.74 (1H, d, J = 8.6 Hz), 9.25 (1H, d, J = 5.3 Hz), 9.78 (1H, d, J = 7.3 Hz). MS (ESI) m/z 384 (M + H)$^+$. |

TABLE 4-continued

| Ex. | Chemical Structure | Compound name/Physical data |
|---|---|---|
| B6 | 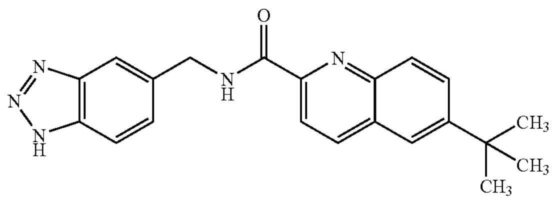 | N-(1H-1,2,3-benzotriazol-5-ylmethyl)-6-tert-butylquinoline-2-carboxamide: It was prepared using Amine 9 and Carboxylic acid 2. LC-MS: Retention time: 2.93 min. MS (ESI) m/z 360 (M + H)+. HPLC condition: Waters (Column: Xterra PrepMS C18, 3.5 um, 4.6 × 50 mm), Detector: photodiodearray (210-400 nm) Conditions: water/MeOH/0.1% aqueous formic acid; 2.0 ml/min at 40° C. |
| B7 | 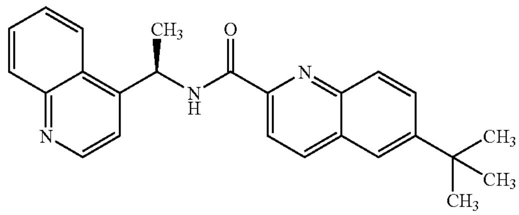 | 6-tert-butyl-N-(1-quinolin-4-ylethyl)quinoline-2-carboxamide: It was isolated as single enantiomer (former peak) from B5 in below HPLC condition. Apparatus: Shimadzu Preparative-HPLC system, Column: Chiralcel OD-H, 20 mm I.D. × 250 mm (No. ODH0CJ-EJ001), DAICEL, Mobile phase: n-Hexane/IPA/Diethylamine = 90/10/0.1 (v/v/v), Flow rate: 20 mL/min, Column temperature: 40° C., Detection: UV 240 nm, Sample concentration: 10mg/mL, Dissolving solvent: EtOH, Injection volume: 500 μL (Maximum), Retention time: 11.2 min and 23.6 min, Run time: 30 min |

Example C1-C17

The compounds of Examples C1 through C17 were prepared by a similar method to that of Example A1 using the following starting materials and the appropriate solvent as described in Scheme 1.

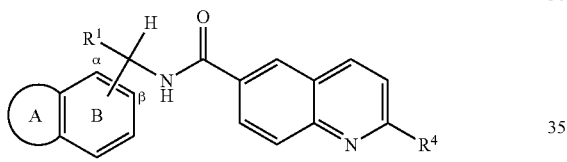

TABLE 5

| Ex. | Chemical Structure | Compound name/Physical data |
|---|---|---|
| C1 | 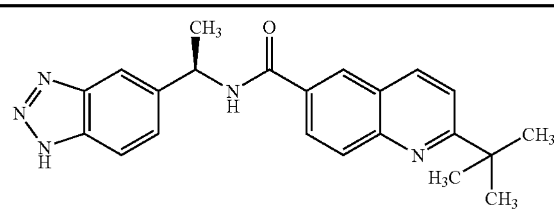 | N-[(1R)-1-(1H-1,2,3-benzotriazol-6-yl)ethyl]-2-tert-butylquinoline-6-carboxamide: It was prepared using Amine 2 and Carboxylic acid 3. $^1$H NMR (300 MHz, CD$_3$OD) δ 1.45 (9H, s), 1.68 (3H, d, J = 7.3 Hz), 5.42-5.49 (1H, m), 7.58-7.72 (2H, m), 7.84-7.97 (2H, m), 8.05-8.14 (2H, m), 8.26-8.40 (2H, m). MS (ESI): m/z 374 (M + H)+. |
| C2 | 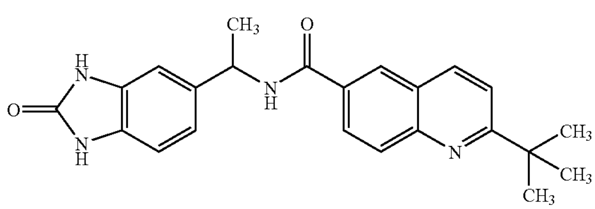 | 2-tert-butyl-N-[(1R)-1-(2-oxo-2,3-dihydro-1H-benzimidazol-6-yl)ethyl]quinoline-6-carboxamide: It was prepared using Amine 6 and Carboxylic acid 3. $^1$H NMR (300 MHz, DMSO-d$_6$) δ 1.42 (9H, s), 1.52 (3H, d, J = 7.4 Hz), 5.16-5.24 (1H, m), 6.87 (1H, d, J = 8.1 Hz), 7.01 (1H, d, J = 8.1 Hz), 7.47 (1H, d, J = 6.6 Hz), 7.77 (1H, d, J = 8.8 Hz), 8.00 (1H, d, J = 8.8 Hz), 8.18 (1H, d, J = 8.8 Hz), 8.39 (1 H, d, J = 8.1 Hz), 8.48 (1H, s), 8.99 (1H, d, J = 8.1 Hz), 10.53 (1H, s), 10.58 (1H, s). MS (ESI): m/z 389 (M + H)+. |
| C3 | 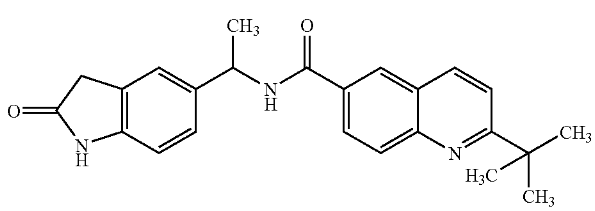 | 2-tert-butyl-N-[1-(2-oxo-2,3-dihydro-1H-indol-5-yl)ethyl]quinoline-6-carboxamide: It was prepared using Amine 5 and Carboxylic acid 3. $^1$H NMR (270 MHz, DMSO-d$_6$) δ 1.42 (9H, s), 1.49 (3H, d, J = 7.3 Hz), 3.47 (2H, s), 5.13-5.23 (1H, m), 6.77 (1H, d, J = 7.9 Hz), 7.23 (1H, d, J = 7.9 Hz), 7.30 (1H, s), 7.76 (1H, d, J = 8.6 Hz), 7.99 (1H, d, J = 8.6 Hz), 8.17 (1H, d, J = 8.6 Hz), 8.39 (1H, d, J = 7.9 Hz), 8.49 (1H, s), 8.96 (1H, d, J = 7.9 Hz), 10.33 (1H, s). MS (ESI): m/z 388 (M + H)+. |

TABLE 5-continued

| Ex. | Chemical Structure | Compound name/Physical data |
|---|---|---|
| C4 | 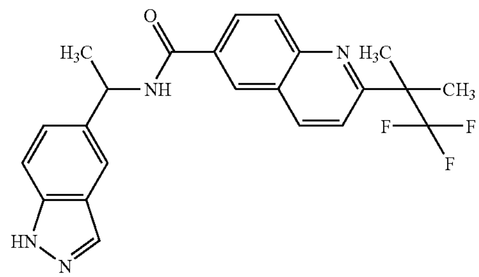 | N-[1-1H-indazole-5-ylethyl]-2-(2,2,2-trifluoro-1,1-dimethylethyl)quinoline-6-carboxamide: It was prepared using Amine 13 and Carboxylic acid 6. $^1$H NMR (300 MHz, DMSO-$d_6$) δ 1.59 (3H, d, J = 7.3 Hz), 1.71 (6H, s), 5.27-5.42 (1H, m), 7.43-7.54 (2H, m), 7.78 (1H, s), 7.88 (1H, d, J = 8.8 Hz), 8.05 (1H, s), 8.09 (1H, d, J = 8.8 Hz), 8.20-8.29 (1H, m), 8.49-8.60 (2H, m), 9.12 (1H, d, J = 8.1 Hz), 13.01 (1H, br-s). MS (ESI) m/z 425 (M − H)$^−$, 427 (M + H)$^+$. |
| C5 | 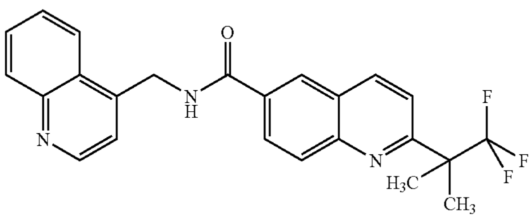 | N-(quinolin-4-ylmethyl)-2-(2,2,2-trifluoro-1,1-dimethylethyl)quinoline-6-carboxamide: It was prepared using Amine 6 and Carboxylic acid 6. $^1$H NMR (300 MHz, DMSO-$d_6$) δ 1.72 (6H, s), 5.07 (2H, d, J = 5.1 Hz), 7.50 (1H, d, J = 4.4 Hz), 7.69 (1H, d, J = 8.1 Hz), 7.80 (1H, t, J = 8.1 Hz), 7.90 (1H, t, J = 8.1 Hz), 8.08 (1H, d, J = 8.8 Hz), 8.13 (1H, d, J = 8.8 Hz), 8.30 (2H, d, J = 8.8 Hz), 8.56 (1H, d, J = 8.8 Hz), 8.64 (1H, s), 8.88 (1H, d, J = 4.4 Hz), 9.47-9.50 (1H, m). MS (ESI): m/z 424 (M + H)$^+$. |
| C6 | 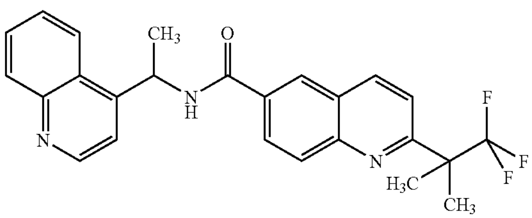 | N-(1-quinolin-4-ylethyl)-2-(2,2,2-trifluoro-1,1-dimethylethyl)quinoline-6-carboxamide: It was prepared using Amine 7 and Carboxylic acid 6. $^1$H NMR (270 MHz, CDCl$_3$) δ 1.73 (6H, s), 1.80 (3H, d, J = 6.6 Hz), 6.21-6.11 (1H, m), 6.67 (1H, d, J = 7.3 Hz), 7.47 (1H, d, J = 4.6 Hz), 7.77-7.59 (3H, m), 8.04 (1H, dd, J = 8.6, 2.0 Hz), 8.22-8.12 (4H, m), 8.28 (1H, d, J = 2.0 Hz), 8.91 (1 H, d, J = 4.6 Hz). MS (ESI) m/z 436 (M − H)$^−$, 438 (M + H)$^+$. |
| C7 | 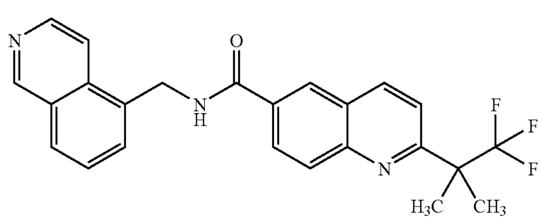 | N-(isoquinolin-5-ylmethyl)-2-(2,2,2-trifluoro-1,1-dimethylethyl)quinoline-6-carboxamide: It was prepared using Amine 8 and Carboxylic acid 6. $^1$H NMR (270 MHz, CDCl$_3$) δ 1.72 (6H, s), 5.17 (2H, 5.9 Hz), 6.55 (1H, br s), 7.66-7.60 (1H, m), 7.70 (1H, d, J = 9.2 Hz), 7.79 (1H, d, J = 6.6 Hz), 8.06-7.94 (3H, m), 8.14 (1H, d, J = 9.2 Hz), 8.20 (1H, d, J = 9.2 Hz), 8.30 (1H, d, J = 2.0 Hz), 8.62 (1H, d, J = 5.9 Hz), 9.32 (1H, s). MS (ESI): m/z 422 (M − H)$^−$, 424 (M + H)$^+$. |
| C8 | 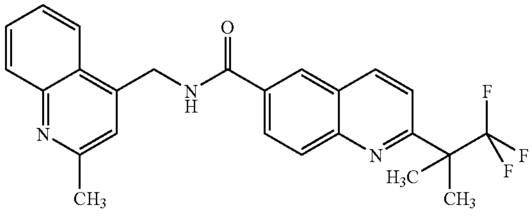 | N-[(2-methylquinolin-4-yl)methyl]-2-(2,2,2-trifluoro-1,1-dimethylethyl)quinoline-6-carboxamide: It was prepared using Amine 10 and Carboxylic acid 6. $^1$H NMR (300 MHz, DMSO-$d_6$) δ 1.71 (6H, s), 2.63 (3H, s), 5.02 (2H, d, J = 5.9 Hz), 7.37 (1H, s), 7.56 (1H, t, J = 8.1 Hz), 7.74 (1H, t, J = 8.1 Hz), 7.89 (1H, d, J = 8.8 Hz), 7.94 (1H, d, J = 8.1 Hz), 8.12 (1H, d, J = 8.8 Hz), 8.22 (1H, d, J = 8.1 Hz), 8.29 (1H, d, J = 7.3 Hz), 8.54 (1H, d, J = 8.1 Hz), 8.62 (1H, s), 9.41-9.44 (1H, m). MS (ESI): m/z 438 (M + H)$^+$. |
| C9 | 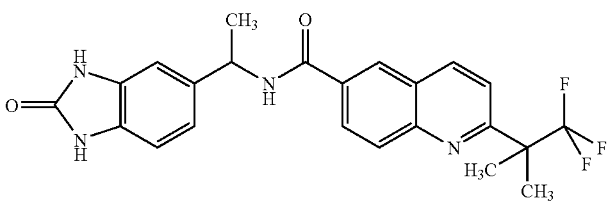 | N-[1-(2-oxo-2,3-dihydro-1H-benzimidazol-5-yl)ethyl]-2-(2,2,2-trifluoro-1,1-dimethylethyl)quinoline-6-carboxamide: It was prepared using Amine 5 and Carboxylic acid 6. $^1$H NMR (300 MHz, DMSO-$d_6$) δ 1.52 (3H, d, J = 7.3 Hz), 1.71 (6H, s), 5.17-5.26 (1H, m), 6.89 (1H, d, J = 8.1 Hz), 7.00-7.02 (2H, m), 7.59 (1H, d, J = 8.8 Hz), 8.09 (1H, d, J = 8.8 Hz), 8.24 (1H, d, J = 8.8 Hz), 8.52-8.57 (2H, m), 9.05 (1H, d, J = 8.1 Hz), 10.55 (1H, s), 10.59 (1H, s). MS (ESI): m/z 443 (M + H)$^+$. |

TABLE 5-continued

| Ex. | Chemical Structure | Compound name/Physical data |
|---|---|---|
| C10 | 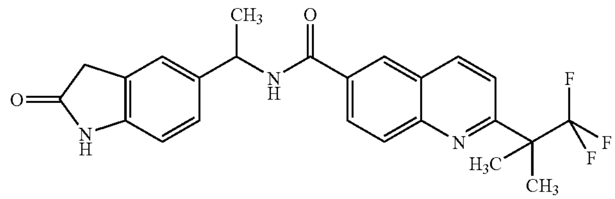 | N-[1-(2-oxo-2,3-dihydro-1H-indol-5-yl)ethyl]-2-(2,2,2-trifluoro-1,1-dimethylethyl)quinoline-6-carboxamide: It was prepared using Amine 4 and Carboxylic acid 6. $^1$H NMR (270 MHz, DMSO) δ 1.50 (3H, d, J = 7.3 Hz), 1.71 (6H, s), 3.30-3.50 (2H, m), 5.15-5.22 (1H, m), 6.77 (1H, d, J = 7.9 Hz), 7.24 (1H, d, J = 7.9 Hz), 7.30 (1H, s), 7.87 (1H, d, J = 9.2 Hz), 8.07 (1H, d, J = 8.6 Hz), 8.23 (1H, d, J = 7.3 Hz), 8.51-8.56 (2H, m), 9.01 (1H, d, J = 7.9 Hz), 10.31 (1H, s). MS (ESI): m/z 442 (M + H)$^+$. |
| C11 | 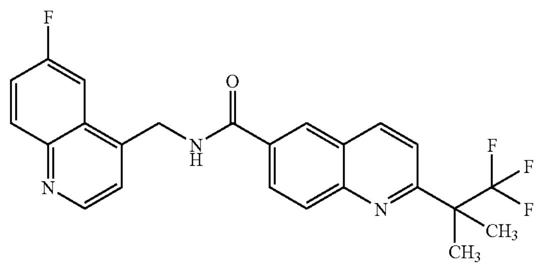 | N-[(6-fluoroquinolin-4-yl)methyl]-2-(2,2,2-trifluoro-1,1-dimethylethyl)quinoline-6-carboxamide: It was prepared using Amine 11 and Carboxylic acid 6. $^1$H NMR (270 MHz, DMSO-d$_6$) δ 1.73 (6H, s), 4.98-5.04 (2H, m), 7.52-7.57 (1H, m), 7.68-7.78 (1H, m), 7.87-7.93 (1H, m), 8.06-8.19 (3H, m), 8.25-8.32 (1H, m), 8.53-8.59 (1H, m), 8.63 (1H, br, s), 8.85-8.90 (1H, m), 9.46-9.54 (1H, m). MS (ESI) m/z 440 (M − H)$^−$, 442 (M + H)$^+$. |
| C12 | 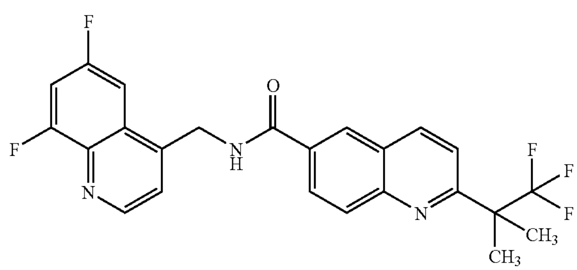 | N-[(6,8-difluoroquinolin-4-yl)methyl]-2-(2,2,2-trifluoro-1,1-dimethylethyl)quinoline-6-carboxamide: It was prepared using Amine 12 and Carboxylic acid 6. $^1$H NMR (270 MHz, DMSO-d$_6$) δ 1.73 (6H, s), 4.98-5.04 (2H, m), 7.62-7.67 (1H, m), 7.74-8.02 (3H, m), 8.12-8.18 (1H, m), 8.26-8.33 (1H, m), 8.54-8.60 (1H, m), 8.64 (1H, br, s), 8.90-8.94 (1H, m), 9.49-9.57 (1H, m). MS (ESI) m/z 458 (M − H)$^−$, 460 (M + H)$^+$. |
| C13 | 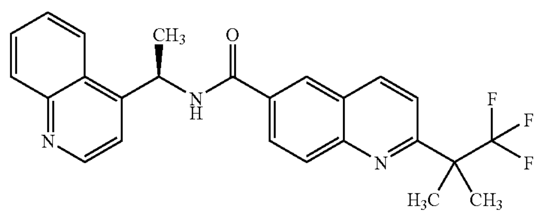 | N-[(1R)-1-quinolin-4-ylethyl]-2-(2,2,2-trifluoro-1,1-dimethylethyl)quinoline-6-carboxamide: Racemic compounds were prepared according to the process disclosed in example A1, using Amine 7 and Carboxylic acid 6. Then, it was isolated as single enantiomer (former peak: 8.8 min) in below HPLC conditions. $^1$H NMR (300 MHz, CDCl$_3$) δ 1.73 (6H, s), 1.80 (3H, d, J = 6.6 Hz), 6.21-6.11 (1H, m), 6.67 (1H, d, J = 7.3 Hz), 7.47 (1H, d, J = 4.6 Hz), 7.77-7.59 (3H, m), 8.04 (1H, dd, J = 8.6, 2.0 Hz), 8.22-8.12 (4H, m), 8.28 (1H, d, J = 2.0 Hz), 8.91 (1h, d, J = 4.6 Hz). MS (ESI): m/z 438 (M + H)$^+$, 436 (M − H)$^−$. HPLC conditions for the enantiomer separation are as follows; Apparatus: Shimadzu Preparative-HPLC system, Column: Chiralpak AD-H, 20 mm I.D. × 250 mm (No. ADH0CJ-DE003), DAICEL, Mobile phase: n-Hexane/EtOH/DEA = 80/20/0.1 (v/v/v/), Flow rate: 20 mL/min, Column temperature: 40° C., Detection: UV 230 nm, Sample concentration: 20 mg/mL, Dissolving solvent: EtOH, Injection volume: 1000 μL (Maximum), Retention time: 8.8 min and 13.5 min, Run time: 18 min. |
| C14 | 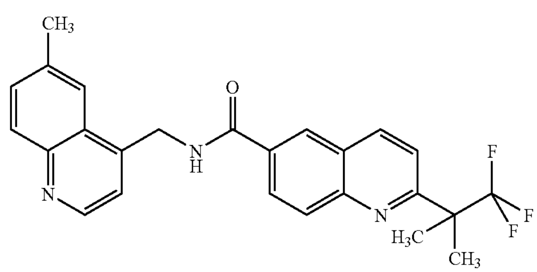 | N-[(6-methylquinolin-4-yl)methyl]-2-(2,2,2-trifluoro-1,1-dimethylethyl)quinoline-6-carboxamide: It was prepared using Amine 14 and Carboxylic acid 6. $^1$H NMR (270 MHz, DMSO) δ 1.72 (6H, s), 2.56 (3H, s), 5.03 (2H, d, J = 5.3 Hz), 7.44 (1H, d, J = 4.0 Hz), 7.63 (1H, d, J = 8.6 Hz), 7.89 (1H, d, J = 8.6 Hz), 7.96 (1H, d, J = 8.6 Hz), 8.07 (1H, s), 8.13 (1H, d, J = 8.6 Hz), 8.26-8.32 (1H, m), 8.56 (1H, d, J = 9.2 Hz), 8.64 (1H, s), 8.77-8.81 (1H, m), 9.44-9.51 (1H, m). MS (ESI): m/z 438 (M + H)$^+$. |

TABLE 5-continued

| Ex. | Chemical Structure | Compound name/Physical data |
| --- | --- | --- |
| C15 | 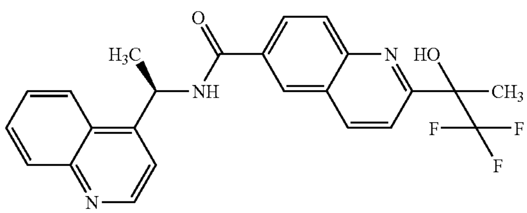 | N-[(1R)-1-quinolin-4-ylethyl]-2-(2,2,2-trifluoro-1-hydroxy-1-methylethyl)quinoline-6-carboxamide: It was prepared using Amine 7A and Carboxylic acid 10. $^1$H NMR (300 MHz, acetone-d$_6$) δ 1.74 (3H, d, J = 6.6 Hz), 1.82 (3H, s), 6.08-6.21 (1H, m), 6.39 (1H, s), 7.60-7.67 (2H, m), 7.70-7.77 (1H, m), 7.92 (1H, d, J = 8.1 Hz), 8.06 (1H, d, J = 9.5 Hz), 8.16 (1H, d, J = 8.8 Hz), 8.29-8.36 (2H, m), 8.52-8.64 (2H, m), 8.56 (1H, d, J = 8.8 Hz), 8.84 (1H, d, J = 4.4 Hz). MS (ESI) m/z 438 (M − H)$^-$, 440 (M + H)$^+$ |
| C16 | 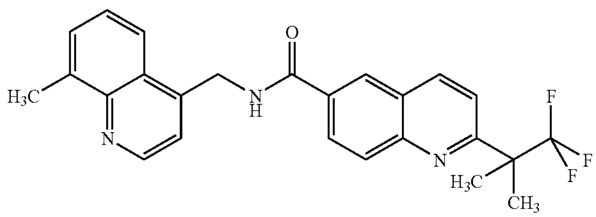 | N-[(8-methylquinolin-4-yl)methyl]-2-(2,2,2-trifluoro-1,1-dimethylethyl)quinoline-6-carboxamide: It was prepared using Amine 15 and Carboxylic acid 6. $^1$H NMR (270 MHz, DMSO) δ 1.73 (6H, s), 2.76 (3H, s), 5.03-5.09 (2H, m), 7.50-7.70 (3H, m), 7.90 (1H, d, J = 8.6 Hz), 8.13 (2H, d, J = 8.6 Hz), 8.29 (1H, d, J = 8.6 Hz), 8.53-8.60 (1H, m), 8.64 (1H, s), 8.89-8.93 (1H, m), 9.48 (1H, brs). MS (ESI): m/z 438 (M + H)$^+$. |
| C17 | 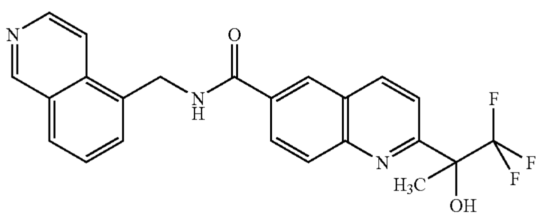 | N-(isoquinolin-5-ylmethyl)-2-(2,2,2-trifluoro-1-hydroxy-1-methylethyl)quinoline-6-carboxamide: It was prepared using Amine 8 and Carboxylic acid 10. $^1$H NMR (270 MHz, DMSO) δ 1.84 (3H, s), 5.01 (2H, d, J = 5.9 Hz), 7.00 (1H, s), 7.89 (1H, t, J = 7.6 Hz), 7.82 (1H, d, J = 7.3 Hz), 7.99 (1H, d, J = 9.2 Hz), 8.07-8.14 (3H, m), 8.25-8.30 (1H, m), 8.56-8.61 (3H, m), 9.35 (1H, s), 9.40 (1H, t, J = 5.9 Hz). MS (ESI): m/z 426 (M + H)$^+$. |
| C18 | 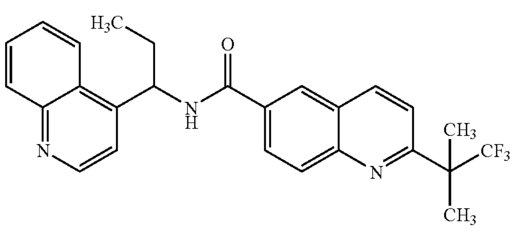 | N-(1-quinolin-4-ylpropyl)-2-(2,2,2-trifluoro-1,1-dimethylethyl)quinoline-6-carboxamide: It was prepared using Amine 16 and Carboxylic acid 6. $^1$H NMR (300 MHz, DMSO-d$_6$) δ 1.08 (3H, t, J = 7.3 Hz), 1.72 (6H, s), 1.96-2.07 (2H, m), 5.81-5.85 (1H, m), 7.64 (1H, d, J = 4.4 Hz), 7.67-7.82 (2H, m), 7.89 (1H, d, J = 8.8 Hz), 8.06-8.13 (2H, m), 8.26 (1H, d, J = 8.8 Hz), 8.39 (1H, d, J = 8.1 Hz), 8.56 (1H, d, J = 8.8 Hz), 8.61 (1H, s), 8.90 (1H, d, J = 5.1 Hz), 9.31 (1H, d, J = 7.3 Hz). MS (ESI) m/z 450 (M − H)$^-$, 452 (M + H)$^+$. |
| C19 | 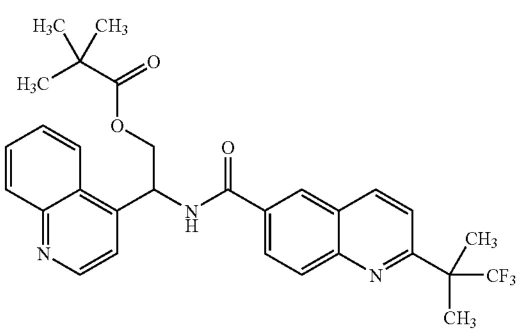 | 2-quinolin-4-yl-2-({[2-(2,2,2-trifluoro-1,1-dimethylethyl)quinolin-6-yl]carbonyl}amino)ethyl pivalate: It was prepared using Amine 17 and Carboxylic acid 6. NMR (300 MHz, DMSO-d$_6$) δ 1.04 (9H, s), 1.72 (6H, s), 4.40-4.50 (1H, m), 4.61-4.68 (1H, m), 6.30-6.38 (1H, m), 7.73-7.92 (4H, m), 8.09-8.18 (2H, m), 8.25 (1H, d, J = 8.1 Hz), 8.46 (1H, d, J = 8.1 Hz), 8.56-8.60 (2H, m), 8.96 (1H, d, J = 4.4 Hz), 9.55 (1H, d, J = 8.1 Hz). MS (ESI) m/z 536 (M − H)$^-$, 538 (M + H)$^+$. |

TABLE 5-continued

| Ex. | Chemical Structure | Compound name/Physical data |
|---|---|---|
| C20 | 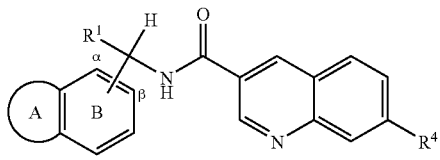 | N-(2-hydroxy-1-quinolin-4-ylethyl)-2-(2,2,2-trifluoro-1,1-dimethylethyl)quinoline-6-carboxamide: To a solution of 2-quinolin-4-yl-2-({[2-(2,2,2-trifluoro-1,1-dimethylethyl)quinolin-6-yl]carbonyl}amino)ethyl pivalate (132 mg, 0.25 mmol) in THF (2 ml) was added lithium aluminum hydride (15 mg, 0.40 mmol) at 0° C. The mixture was stirred at 0° C. for 1 hour and at room temperature for 2 hours. The reaction mixture was quenched with sat. NaCl aq. and diluted with ethyl acetate. The separated organic layer was dried over $Na_2SO_4$, concentrated and purified through silica gel column chromatography eluting with Hexane/EtOAc (1:1 to 1:2) to furnish the title compound (59 mg, 53% yield) as a white solid. NMR (300 MHz, DMSO-$d_6$) δ 1.72 (6H, s), 3.88-3.94 (2H, m), 5.23 (1H, t, J = 5.9 Hz), 5.96-6.02 (1H, m), 7.66 (1H, d, J = 4.4 Hz), 7.72 (1H, t, J = 8.1 Hz), 7.81 (1H, t, J = 8.1 Hz), 7.89 (1H, d, J = 8.1 Hz), 8.08 (1H, d, J = 8.1 Hz), 8.12 (1H, d, J = 8.8 Hz), 8.28 (1H, d, J = 8.8 Hz), 8.38 (1H, d, J = 8.1 Hz), 8.56 (1H, d, J = 8.8 Hz), 8.64 (1H, s), 8.90 (1H, d, J = 4.4 Hz), 9.30 (1H, d, J = 7.3 Hz). MS (ESI) m/z 452 (M − H)$^-$, 454 (M + H)$^+$. |

Example D1 wherein ring A is

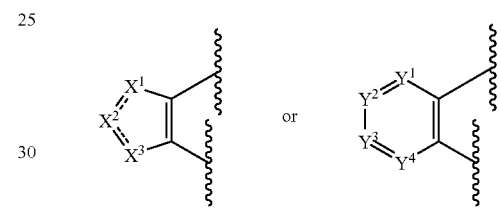

TABLE 6

| Ex. | Chemical Structure | Compound name/Physical data |
|---|---|---|
| D1 | 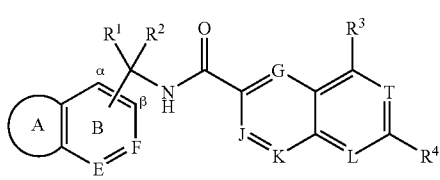 | 7-tert-butyl-N-(1-quinolin-4-ylethyl)quinoline-3-carboxamide: It was prepared using Amine 7 and Carboxylic acid 9. $^1$H-NMR (270 MHz, DMSO-$d_6$) δ 1.41 (9H, s), 1.67 (3H, d, J = 7.3 Hz), 6.07-5.97 (1H, m), 7.86-7.64 (5H, m), 8.10-7.99 (3H, m), 8.34 (1H, d, J = 7.9 Hz), 8.91-8.87 (2H, m), 9.30 (1H, d, J = 2.0 Hz), 9.43 (1H, d, J = 7.3 Hz). MS (ESI): m/z 382 (M − H)$^-$, 384 (M + H)$^+$. |

The invention claimed is:

1. A compound of the formula (I):

(I)

wherein
one of $X^1$ and $X^3$ is N, another of $X^1$ and $X^3$ is NH or S, and $X^2$ is N or $CR^5$,
one of $X^1$ and $X^3$ is $CH_2$, another of $X^1$ and $X^3$ is NH or N, and $X^2$ is C=O or N,
one of $X^1$ and $X^3$ is $CR^6$, another of $X^1$ and $X^3$ is NH, and $X^2$ is N or $CR^5$,
$X^1$ and $X^3$ are NH and $X^2$ is C=O, or
$Y^1$ is N or $CR^7$, $Y^2$ is N or $CR^8$, $Y^3$ is N or $CR^9$ and $Y^4$ is N or $CR^{10}$;
the substitution site of ring B is the alpha- or beta-position;
E is CH or N; G, J and K are each CH; F is CH or C—$CH_3$;
L is N and T is CH; $R^1$ and $R^2$ are each independently hydrogen, ($C_1$-$C_6$)alkyl, or hydroxy($C_1$-$C_6$)alkyl; $R^3$ is hydrogen; $R^4$ is ($C_1$-$C_6$)alkyl, hydroxy($C_1$-$C_6$)alkyl, ($C_3$-$C_6$)cycloalkyl, ($C_1$-$C_4$)alkyl($C_3$-$C_6$)cycloalkyl, ($C_1$-$C_4$)alkoxy($C_1$-$C_6$)alkyl optionally substituted with halo or halo($C_2$-$C_6$)alkyl optionally substituted with hydroxy, $R^5$ and $R^6$ are each independently hydrogen, ($C_1$-$C_6$)alkyl, hydroxy($C_1$-$C_6$)alkyl or hydroxy($C_1$-$C_6$)

alkoxy-$(C_1-C_6)$alkyl; $R^7$, $R^8$, $R^9$ and $R^{10}$ are each independently hydrogen, halo, $(C_1-C_6)$alkyl, hydroxy$(C_1-C_6)$alkyl or hydroxy$(C_1-C_6)$alkoxy-$(C_1-C_6)$alkyl; and each dotted bond is a single or a double bond; or a pharmaceutically acceptable salt thereof.

2. A compound according to claim 1, wherein
one of $X^1$ and $X^3$ is N, another of $X^1$ and $X^3$ is NH, and $X^2$ is N or $CR^5$,
one of $X^1$ and $X^3$ is $CH_2$, another of $X^1$ and $X^3$ is NH or N, and $X^2$ is C=O or N,
one of $X^1$ and $X^3$ is $CR^6$, another of $X^1$ and $X^3$ is NH, and $X^2$ is N, or
$X^1$ and $X^3$ are NH and $X^2$ is C=O;
F is CH or C—$CH_3$; E is CH or N;
$R^1$ and $R^2$ are each independently hydrogen, $(C_1-C_6)$alkyl; $R^3$ is hydrogen; $R^4$ is $(C_1-C_6)$alkyl, $(C_3-C_6)$cycloalkyl, $(C_1-C_4)$alkyl$(C_3-C_6)$cycloalkyl, $(C_1-C_4)$alkoxy$(C_1-C_6)$alkyl optionally substituted with halo or halo$(C_2-C_6)$alkyl optionally substituted with hydroxyl; and $R^5$ and $R^6$ are hydrogen, or a pharmaceutically acceptable salt thereof.

3. A compound according to claim 2 wherein $X^1$ is N, $X^3$ is NH and $X^2$ is $CR^5$; $X^1$ is $CH_2$, $X^3$ is NH or N, and $X^2$ is C=O or N; $X^1$ is $CR^5$, $X^3$ is NH, and $X^2$ is N or $CR^5$; or $X^1$ is NH, $X^3$ is N, and $X^2$ is N; or $X^1$ and $X^3$ are NH and $X^2$ is C=O; or a pharmaceutically acceptable salt thereof.

4. A compound according to claim 3, wherein $X^1$ is NH, $X^3$ is N and $X^2$ is N; or $X^1$ is $CH_2$, $X^3$ is N, and $X^2$ is N; or a pharmaceutically acceptable salt thereof.

5. A compound according to claim 1, wherein $Y^1$, $Y^2$, $Y^3$ and $Y^4$ are $CR^7$, $CR^8$, $CR^9$ and $CR^{10}$, respectively, or $Y^2$ is N and $Y^1$, $Y^3$ and $Y^4$ are CH; F is CH or C—$CH_3$; E is CH or N; $R^1$ and $R^2$ are each independently hydrogen, $(C_1-C_6)$alkyl; $R^3$ is hydrogen; $R^4$ is $(C_1-C_6)$alkyl, $(C_3-C_6)$cycloalkyl, $(C_1-C_4)$alkyl$(C_3-C_6)$cycloalkyl, $(C_1-C_4)$alkoxy$(C_1-C_6)$alkyl optionally substituted with halo or halo$(C_2-C_6)$alkyl optionally substituted with hydroxy, and $R^7$, $R^8$, $R^9$ and $R^{10}$ are each independently hydrogen or $(C_1-C_6)$alkyl or a pharmaceutically acceptable salt thereof.

6. A compound according to claim 5, wherein E is N, and $Y^1$, $Y^2$, $Y^3$ and $Y^4$ are $CR^7$, $CR^8$, $CR^9$ and $CR^{10}$, respectively, in which $R^7$, $R^8$, $R^9$ and $R^{10}$ are each independently hydrogen or methyl, or a pharmaceutically acceptable salt thereof.

7. A compound according to claim 5, wherein E and F are CH and $Y^3$ is N and $Y^1$, $Y^2$ and $Y^4$ are CH, or a pharmaceutically acceptable salt thereof.

8. A compound according to claim 1, wherein $R^4$ is cyclopropyl, 1-methyl-cylopropyl, tert-butyl, 2,2,2-trifluoro-1-hydroxy-1-methylethyl, 2,2,2-trifluoro-1-methoxy-1-methylethyl or 2,2,2-trifluoro-1,1-dimethyl-ethyl, or a pharmaceutically acceptable salt thereof.

9. A compound according to 8 wherein said compound being of formula (Ia)

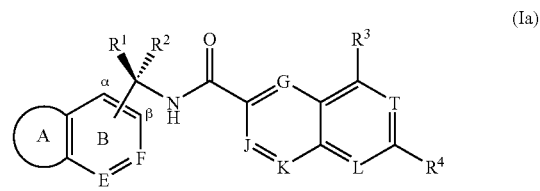

(Ia)

wherein $R^1$ is methyl and $R^2$ is H, or a pharmaceutically acceptable salt thereof.

10. A compound according to claim 1, wherein the compound is selected from the group consisting of:
N-[(1R)-1-(1H-1,2,3-benzotriazol-6-yl)ethyl]-2-tert-butylquinoline-6-carboxamide;
2-tert-butyl-N-[(1R)-1-(2-oxo-2,3-dihydro-1H-benzimidazol-6-yl)ethyl]quinoline-6-carboxamide;
N-[1-1H-indazole-5-ylethyl]-2-(2,2,2-trifluoro-1,1-dimethylethyl)quinoline-6-carboxamide;
N-(quinolin-4-ylmethyl)-2-(2,2,2-trifluoro-1,1-dimethylethyl)quinoline-6-carboxamide;
N-isoquinolin-5-ylmethyl )-2-(2,2,2-trifluoro-1,1-dimethylethyl)quinoline-6-carboxamide; and
N-[(1R)-1-quinolin-4-ylethyl]-2-(2,2,2-trifluoro-1,1-dimethylethyl)quinoline-6-carboxamide;
and pharmaceutically acceptable salts thereof.

11. A pharmaceutical composition including a compound of the formula (I) or a pharmaceutically acceptable salt thereof, as defined in claim 1, together with a pharmaceutically acceptable excipient.

12. A combination of a compound of the formula (I) or the pharmaceutical acceptable salt as defined in claim 1, and another pharmacologically active agent.

* * * * *